US010775305B2

(12) United States Patent
Rothberg et al.

(10) Patent No.: US 10,775,305 B2
(45) Date of Patent: Sep. 15, 2020

(54) INTEGRATED DEVICE FOR TEMPORAL BINNING OF RECEIVED PHOTONS

(71) Applicant: Quantum-Si Incorporated, Guilford, CT (US)

(72) Inventors: Jonathan M. Rothberg, Guilford, CT (US); Keith G. Fife, Palo Alto, CA (US); David Boisvert, San Jose, CA (US)

(73) Assignee: Quantum-Si Incorporated, Guilford, CT (US)

( * ) Notice: Subject to any disclaimer, the term of this patent is extended or adjusted under 35 U.S.C. 154(b) by 126 days.

(21) Appl. No.: 15/914,019

(22) Filed: Mar. 7, 2018

(65) Prior Publication Data
US 2018/0259456 A1    Sep. 13, 2018

Related U.S. Application Data

(63) Continuation of application No. 15/656,139, filed on Jul. 21, 2017, now Pat. No. 9,945,779, which is a
(Continued)

(51) Int. Cl.
*G01N 21/64* (2006.01)
*H01L 27/146* (2006.01)
(Continued)

(52) U.S. Cl.
CPC ....... *G01N 21/6428* (2013.01); *C12Q 1/6869* (2013.01); *G01N 21/645* (2013.01);
(Continued)

(58) Field of Classification Search
CPC .................................................. G01N 21/6408
See application file for complete search history.

(56) References Cited

U.S. PATENT DOCUMENTS

| 5,198,543 A | 3/1993 | Blanco et al. |
| 5,302,509 A | 4/1994 | Cheeseman |

(Continued)

FOREIGN PATENT DOCUMENTS

| CN | 2433618 Y | 6/2001 |
| CN | 1364940 A | 8/2002 |

(Continued)

OTHER PUBLICATIONS

Invitation to Pay Additional Fees for International Application No. PCT/US2014/066014 dated Jan. 28, 2015.
(Continued)

*Primary Examiner* — Thanh Luu
(74) *Attorney, Agent, or Firm* — Wolf, Greenfield & Sacks, P.C.

(57) ABSTRACT

An integrated circuit includes a photodetection region configured to receive incident photons. The photodetection region is configured to produce a plurality of charge carriers in response to the incident photons. The integrated circuit also includes at least one charge carrier storage region. The integrated circuit also includes a charge carrier segregation structure configured to selectively direct charge carriers of the plurality of charge carriers into the at least one charge carrier storage region based upon times at which the charge carriers are produced.

15 Claims, 63 Drawing Sheets

Related U.S. Application Data continuation of application No. 14/821,656, filed on Aug. 7, 2015, now Pat. No. 9,759,658.

(60) Provisional application No. 62/164,506, filed on May 20, 2015, provisional application No. 62/035,377, filed on Aug. 8, 2014.

(51) Int. Cl.
  *H01L 27/148* (2006.01)
  *G01S 7/4865* (2020.01)
  *C12Q 1/6869* (2018.01)
  *G01S 7/4863* (2020.01)

(52) U.S. Cl.
  CPC ..... *G01N 21/6408* (2013.01); *G01N 21/6458* (2013.01); *G01S 7/4865* (2013.01); *H01L 27/14603* (2013.01); *H01L 27/14687* (2013.01); *H01L 27/14812* (2013.01); *G01N 2021/6439* (2013.01); *G01N 2021/6441* (2013.01); *G01N 2201/0697* (2013.01); *G01N 2201/06113* (2013.01); *G01S 7/4863* (2013.01)

(56) References Cited

U.S. PATENT DOCUMENTS

| | | |
|---|---|---|
| 5,355,165 A | 10/1994 | Kosonocky et al. |
| 5,471,515 A | 11/1995 | Fossum et al. |
| 5,674,743 A | 10/1997 | Ulmer |
| 5,822,472 A | 10/1998 | Danielzik et al. |
| 5,912,155 A | 6/1999 | Chatterjee et al. |
| 6,137,117 A | 10/2000 | Feldstein et al. |
| 6,198,869 B1 | 3/2001 | Kraus et al. |
| 6,210,896 B1 | 4/2001 | Chan |
| 6,232,103 B1 | 5/2001 | Short |
| 6,255,083 B1 | 7/2001 | Williams |
| 6,261,797 B1 | 7/2001 | Sorge et al. |
| 6,265,193 B1 | 7/2001 | Brandis et al. |
| 6,280,939 B1 | 8/2001 | Allen |
| 6,327,410 B1 | 12/2001 | Walt et al. |
| 6,355,420 B1 | 3/2002 | Chan |
| 6,399,320 B1 | 6/2002 | Markau et al. |
| 6,399,335 B1 | 6/2002 | Kao et al. |
| 6,437,345 B1 | 8/2002 | Bruno-Raimondi et al. |
| 6,445,491 B2 | 9/2002 | Sucha et al. |
| 6,607,883 B1 | 8/2003 | Frey et al. |
| 6,686,582 B1 | 2/2004 | Volcker et al. |
| 6,716,394 B2 | 4/2004 | Jensen et al. |
| 6,825,921 B1 | 11/2004 | Modlin et al. |
| 6,936,702 B2 | 8/2005 | Williams et al. |
| 6,975,898 B2 | 12/2005 | Seibel |
| 7,033,762 B2 | 4/2006 | Nelson et al. |
| 7,052,847 B2 | 5/2006 | Korlach et al. |
| 7,057,026 B2 | 6/2006 | Barnes et al. |
| 7,153,672 B1 | 12/2006 | Eickbush et al. |
| 7,158,224 B2 | 1/2007 | Montagu |
| 7,170,050 B2 | 1/2007 | Turner et al. |
| 7,179,654 B2 | 2/2007 | Verdonk et al. |
| 7,270,951 B1 | 9/2007 | Stemple et al. |
| 7,345,764 B2 | 3/2008 | Bulovic et al. |
| 7,393,640 B2 | 7/2008 | Kumar et al. |
| 7,405,281 B2 | 7/2008 | Xu et al. |
| 7,462,452 B2 | 12/2008 | Williams et al. |
| 7,595,883 B1 | 9/2009 | El Gamal et al. |
| 7,630,073 B2 | 12/2009 | Lundquist et al. |
| 7,738,086 B2 | 6/2010 | Shepard et al. |
| 7,745,116 B2 | 6/2010 | Williams |
| 7,820,983 B2 | 10/2010 | Lundquist et al. |
| 7,871,777 B2 | 1/2011 | Schneider et al. |
| 7,873,085 B2 | 1/2011 | Babushkin et al. |
| 7,875,440 B2 | 1/2011 | Williams et al. |
| 7,968,702 B2 | 6/2011 | Wegener et al. |
| 7,973,146 B2 | 7/2011 | Shen et al. |
| 7,981,604 B2 | 7/2011 | Quake |
| 8,058,030 B2 | 11/2011 | Smith et al. |
| 8,133,672 B2 | 3/2012 | Bjornson et al. |
| 8,153,375 B2 | 4/2012 | Travers et al. |
| 8,174,696 B2 | 5/2012 | Ebbesen et al. |
| 8,238,993 B2 | 8/2012 | Maynard et al. |
| 8,274,034 B2 | 9/2012 | Vogel et al. |
| 8,274,040 B2 | 9/2012 | Zhong et al. |
| 8,278,728 B2 | 10/2012 | Murshid |
| 8,323,939 B2 | 12/2012 | Hanzel et al. |
| 8,343,746 B2 | 1/2013 | Rank et al. |
| 8,465,699 B2 | 6/2013 | Fehr et al. |
| 8,481,264 B2 | 7/2013 | Bjornson et al. |
| 8,501,406 B1 | 8/2013 | Gray et al. |
| 8,501,922 B2 | 8/2013 | Otto et al. |
| 8,502,169 B2 | 8/2013 | Rigneault et al. |
| 8,580,539 B2 | 11/2013 | Korlach |
| 8,865,077 B2 | 10/2014 | Chiou et al. |
| 8,921,086 B2 | 12/2014 | Hanzel et al. |
| 9,062,091 B2 | 6/2015 | Bjornson et al. |
| 9,127,259 B2 | 9/2015 | Bjornson et al. |
| 9,606,058 B2 | 3/2017 | Rothberg et al. |
| 9,696,258 B2 | 7/2017 | Rothberg et al. |
| 9,759,658 B2 | 9/2017 | Rothberg et al. |
| 9,945,779 B2 | 4/2018 | Rothberg et al. |
| 10,441,174 B2 | 10/2019 | Rothberg et al. |
| 2001/0009269 A1* | 7/2001 | Hayashi ......... A61B 1/00009 250/458.1 |
| 2001/0017727 A1 | 8/2001 | Sucha et al. |
| 2001/0055462 A1 | 12/2001 | Seibel |
| 2002/0031836 A1 | 3/2002 | Feldstein |
| 2004/0004194 A1 | 1/2004 | Amblard et al. |
| 2004/0144927 A1 | 7/2004 | Auner et al. |
| 2004/0169842 A1 | 9/2004 | Dosluoglu et al. |
| 2006/0249657 A1 | 11/2006 | O'Grady |
| 2007/0042500 A1 | 2/2007 | Meyer-Almes et al. |
| 2007/0250274 A1 | 10/2007 | Volkov et al. |
| 2007/0281288 A1 | 12/2007 | Belkin et al. |
| 2008/0050747 A1 | 2/2008 | Korlach et al. |
| 2008/0097174 A1 | 4/2008 | Maynard et al. |
| 2009/0014658 A1 | 1/2009 | Cottier et al. |
| 2010/0009872 A1 | 1/2010 | Eid et al. |
| 2010/0141927 A1 | 6/2010 | Hashimoto et al. |
| 2010/0173394 A1 | 7/2010 | Colston et al. |
| 2010/0255487 A1 | 10/2010 | Beechem et al. |
| 2010/0323406 A1 | 12/2010 | Vatta et al. |
| 2011/0136201 A1 | 6/2011 | Mao et al. |
| 2011/0165652 A1 | 7/2011 | Hardin et al. |
| 2011/0236983 A1 | 9/2011 | Beechem et al. |
| 2011/0298079 A1* | 12/2011 | Kawahito ......... H01L 27/14603 257/443 |
| 2012/0094332 A1 | 4/2012 | Lee et al. |
| 2012/0322692 A1 | 12/2012 | Pham et al. |
| 2013/0005047 A1 | 1/2013 | Mayer et al. |
| 2013/0023039 A1 | 1/2013 | Zaccarin et al. |
| 2013/0071849 A1 | 3/2013 | Kong et al. |
| 2013/0072768 A1 | 3/2013 | Crane et al. |
| 2013/0090537 A1 | 4/2013 | Schemmann et al. |
| 2013/0149734 A1 | 6/2013 | Ammar et al. |
| 2013/0183676 A1* | 7/2013 | Chen ................ G01N 21/6408 435/6.12 |
| 2013/0217007 A1 | 8/2013 | Kamtekar et al. |
| 2014/0217264 A1 | 8/2014 | Shepard et al. |
| 2015/0042954 A1 | 2/2015 | Hunter et al. |
| 2015/0141267 A1 | 5/2015 | Rothberg et al. |
| 2015/0141268 A1 | 5/2015 | Rothberg et al. |
| 2015/0172526 A1 | 6/2015 | Swihart et al. |
| 2015/0293021 A1* | 10/2015 | Finkelstein ....... G01N 21/6452 506/13 |
| 2016/0041095 A1 | 2/2016 | Rothberg et al. |
| 2016/0084761 A1 | 3/2016 | Rothberg et al. |
| 2016/0133668 A1 | 5/2016 | Rothberg et al. |
| 2016/0181298 A1 | 6/2016 | Wan et al. |
| 2016/0338631 A1 | 11/2016 | Li et al. |
| 2016/0356718 A1 | 12/2016 | Yoon et al. |
| 2016/0377543 A1 | 12/2016 | Rothberg et al. |
| 2016/0380025 A1 | 12/2016 | Rothberg et al. |
| 2017/0231500 A1 | 8/2017 | Rothberg et al. |
| 2017/0322153 A1 | 11/2017 | Rothberg et al. |

(56) References Cited

U.S. PATENT DOCUMENTS

| | | | |
|---|---|---|---|
| 2018/0180546 | A1 | 6/2018 | Rothberg et al. |
| 2019/0374107 | A1 | 12/2019 | Rothberg et al. |
| 2019/0391010 | A1 | 12/2019 | Thurston et al. |

FOREIGN PATENT DOCUMENTS

| | | | |
|---|---|---|---|
| CN | 1138862 C | | 2/2004 |
| CN | 1867822 A | | 11/2006 |
| CN | 102395874 A | | 3/2012 |
| CN | 103728446 A | | 4/2014 |
| EP | 1681356 A1 | | 7/2006 |
| EP | 2182523 A1 | | 5/2010 |
| EP | 2339632 A1 | | 6/2011 |
| EP | 2391639 | | 12/2011 |
| EP | 2134871 B1 | | 3/2012 |
| EP | 2487897 A1 | | 8/2012 |
| EP | 3194935 A2 | | 7/2017 |
| JP | 2000-165750 A | | 6/2000 |
| WO | WO 91/06678 A1 | | 5/1991 |
| WO | WO 2005/073407 A1 | | 8/2005 |
| WO | WO 2007/015168 A2 | | 2/2007 |
| WO | WO 2010/025331 A1 | | 3/2010 |
| WO | WO 2011/103497 A1 | | 8/2011 |
| WO | WO 2011/103507 A1 | | 8/2011 |
| WO | WO 2013/171197 A1 | | 11/2013 |
| WO | WO 2016/022998 A2 | | 2/2016 |
| WO | WO 2016/022998 A3 | | 2/2016 |
| WO | WO 2016/128198 A1 | | 8/2016 |
| WO | WO 2016/187580 A1 | | 11/2016 |
| WO | WO 2017/210413 A1 | | 12/2017 |

OTHER PUBLICATIONS

International Search Report and Written Opinion for International Application No. PCT/US2014/066014 dated Apr. 7, 2015.
International Preliminary Report on Patentability for International Application No. PCT/US2014/066014 dated May 26, 2016.
Invitation to Pay Additional Fees for International Application No. PCT/US2015/044360 dated Nov. 20, 2015.
International Search Report and Written Opinion for International Application No. PCT/US2015/044360 dated Feb. 3, 2016.
Invitation to Pay Additional Fees for International Application No. PCT/US2015/044378 dated Oct. 30, 2015.
International Search Report and Written Opinion for International Application No. PCT/US2015/044378 dated Jan. 15, 2016.
Invitation to Pay Additional Fees for International Application No. PCT/US2015/044379 dated Nov. 2, 2015.
International Search Report and Written Opinion for International Application No. PCT/US2015/044379 dated Jan. 15, 2016.
Invitation to Pay Additional Fees for International Application No. PCT/US2014/066013 dated Jan. 28, 2015.
International Search Report and Written Opinion for International Application No. PCT/US2014/066013 dated Apr. 7, 2015.
International Preliminary Report on Patentability for International Application No. PCT/US2014/066013 dated May 26, 2016.
Invitation to Pay Additional Fees for International Application No. PCT/US2014/066010 dated Jan. 28, 2015.
International Search Report and Written Opinion for International Application No. PCT/US2014/066010 dated Apr. 7, 2015.
International Preliminary Report on Patentability for International Application No. PCT/US2014/066010 dated May 26, 2016.
[No Author Listed] 5.2 Megapixels, 1-inch, 250fps, global-shutter CMOS image sensor, Anafocus, Oct. 2012, 4 pages, Sevilla, Spain.
[No Author Listed] Detect Cancer with our 4 Picos ICCD camera, Stanford Computer Optics, 2013, 2 pages, http://www.stanfordcomputeroptics.com/applications/life-science/time-resolved-flim.html [last accessed May 9, 2014].
[No Author Listed] ICCD camera applications in the field of Life Science, Stanford Computer Optics, 2013, 2 pages, http://www.stanfordcomputeroptics.com/applications/life-science.html [last accessed May 9, 2014].

Achermann, Exciton—Plasmon Interactions in Metal—Semiconductor Nanostructures, The Journal Physical Chemistry Letters, Sep. 13, 2010, 1(19):2837-43.
Akselrod et al, Twenty-fold enhancement of molecular fluorescence by coupling to a J-aggregate critically coupled resonator. ACS Nano. Jan. 24, 2012;6(1):467-71. doi: 10.1021/nn203789t. Epub Dec. 1, 2011.
Algar et al., Interfacial Chemistry and the Design of Solid-Phase Nucleic Acid Hybridization Assays Using Immobilized Quantum Dots as Donors in Fluorescence Resonance Energy Transfer, Sensors, Jun. 2011, 11(6):6214-36.
Aouani et al., Bright unidirectional fluorescence emission of molecules in a nanoaperture with plasmonic corrugations. Nano Lett. Feb. 9, 2011;11(2):637-44. doi: 10.1021/nl103738d. Epub Jan. 19, 2011.
Aouani et al., Plasmonic Antennas for Directional Sorting of Fluorescence Emission, Nano Letters, May 18, 2011, 11(6):2400-6.
Aouani et al., Saturated excitation of fluorescence to quantify excitation enhancement in aperture antennas, Optics Express, Jul. 30, 2012, 20(16):18085-90.
Aouani et al., Supporting Information for Bright unidirectional fluorescence emission of molecules in a nanoaperture with plasmonic corrugations. Nano Lett. Feb. 9, 2011;11(2):19 pages.
Aouani et al., Supporting Information for Plasmonic Antennas for Directional Sorting of Fluorescence Emission, Nano Letters, May 18, 2011, 11(6):9 pages.
Bergman et al., Surface Plasmon Amplification by Stimulated Emission of Radiation: Quantum Generation of Coherent Surface Plasmons in Nanosystems, Physical Review Letters, Jan. 17, 2013, 90(2):027402-1-4.
Bogaerts et al., High speed 36 Gbps 12Mpixel global pipelined shutter CMOS image sensor with CDS, 2011 International Image Sensor Workshop, Jun. 8-11, 2011, 4 pages, Hokkaido, Japan.
Carretero-Palacious et al., Mechanisms for extraordinary optical transmission through bull's eye structures, Optics Express, May 23, 2011, 19(11):10429-42.
Chanyawadee et al., Nonradiative exciton energy transfer in hybrid organic-inorganic heterostructures, Phys. Rev. B., May 14, 2008, 77(19): 193402-1-4.
Daldosso et al., Fabrication and optical characterization of thin two-dimensional Si3N4 waveguides, Materials Science in Semiconductor Processing, Oct. 18, 2004, 7(4-6): 453-8.
Davies et al., Plasmonic Nanogap Tilings: Light-Concentrating Surfaces for Low-Loss Photonic Integration, ACS Nano, Jul. 4, 2013, 7(8):7093-100, arXiv:1305.2839v2, http://arxiv.org/abs/1305.2839v2.
Deshpande et al., Electrically driven polarized single-photon emission from an InGaN quantum dot in a GaN nanowire, Nature Communcations, Apr. 9, 2013, 8 pages.
Deutsch et al., Luminescence upconversion in colloidal double quantum dots, Nature Nanotechnology Letter, Sep. 2013, 8(9):649-53.
Edel et al., Accurate Single Molecule FRET Efficiency Determination for Surface Immobilized DNA Using Maximum Likelihood Calculated Lifetimes, J. Phys. Chem, Mar. 22, 2007, 111(11):2986-90.
Eggeling et al., Monitoring conformational dynamics of a single molecule by selective fluorescence spectroscopy. Proc. Natl. Acad. Sci. 1998;95:1556-61.
Eid et al., Real-time DNA sequencing from single polymerase molecules. Science. Jan. 2, 2009;323(5910):133-8. doi:10.1126/science.1162986. Epub Nov. 20, 2008.
Eid et al., Supporting Online Material for Real-time DNA sequencing from single polymerase molecules. Science. Jan. 2, 2009;323(5910):21 pages.
Feldman et al., Wafer-Level Camera Technologies Shrink Camera Phone Handsets, Photonics.com, Aug. 1, 2007, 3 pages, http://www.photonics.com/Article.aspx?AID=30459 . [last accessed Dec. 17, 2013].
Fu et al., A microfabricated fluorescence-activated cell sorter. Nature Biotechnology. Nov. 1999; 17(11): 1109-1111.

(56) References Cited

OTHER PUBLICATIONS

Gorin et al., Fabrication of silicon nitride waveguides for visible-light using PECVD: a study of the effect of plasma frequency on optical properties, Optics Express, Sep. 1, 2008, 16(18):13509-16.
Gryczynski et al., Two-photon excitation by the evanescent wave from total internal reflection. Anal Biochem., Apr. 5, 1997;247(1):69-76.
Haase et al., Upconverting Nanoparticles, Angewandte Chemie International Edition, Jun. 20, 2011, 50(26):5808-29.
Hallman et al., 3 nJ, 100 ps laser pulses generated with an asymmetric waveguide laser diode for a single-photon avalanche diode time-of-flight (SPAD TOF) rangefinder application, Measurement Science and Technology, Jan. 5, 2012, 23(2): 8 pages.
Hansard et al., Time-of-Flight Cameras: Principles, Methods and Applications, Nov. 2012, 102 pages, Springer-Verlag, London, UK.
He et al., DNA Sequencing by Capillary Electrophoresis with Four-Decay Fluorescence Detection, Anal. Chem., Dec. 15, 2000, 72(24):5865-73.
Herold et al., OLED-on-CMOS Integration for Augmented-Reality Systems, IEEE 2008 International Students and Young Scientists Workshop Photonics and Microsystems, Jun. 20-22, 2008, 19-22, Wroclaw—Szlarska Poreba, Poland.
Heucke et al., Placing Individual Molecules in the Center of Nanoapertures, Nano Letters, Feb. 12, 2014, 14(2):391-5.
Inoue et al., CMOS active pixel image sensor with in-pixel CDS for high-speed cameras, Proc. SPIE, Sensors and Camera Systems for Scientific, Industrial, and Digital Photography Applications V, 250, Jun. 7, 2004, 5301(4):8 pages.
Ishii et al., Self-matched high-voltage rectangular wave pulse generator, Rev. Sci. Instrum, Nov. 1985, 56(11):2116-8.
Jun et al., Plasmonic beaming and active control over fluorescent emission, Nature Communications, Apr. 19, 2011, 6 pages.
Juodawlkis et al., High-Power, Low-Noise Slab-Coupled Optical Waveguide (SCOW) Amplifiers and Lasers, IEEE Optical Society of America Optical Fiber Communication Conference and Exposition and the National FiberOptic Engineers Conference, Mar. 6-10, 2011, 3 pages, Los Angeles, CA.
Juodawlkis et al., High-Power, Ultralow-Noise Semiconductor External Cavity Lasers Based on Low-Confinement Optical Waveguide Gain Media, Proc. of SPIE Novel In-Plane Semiconductor Lasers IX, Feb. 12, 2010, vol. 7616:76160X-1-9.
Kano et al., Two-photon-excited fluorescence enhanced by a surface plasmon. Opt Lett. Nov. 15, 1996;21(22):1848-50.
Karow, PacBio Aims to Boost Throughput of SMRT Technology with Microchip Co-development Deal, In Sequence and Clinical Sequencing News, Jul. 24, 2012, 3 pages, GenomeWeb.
Klein et al., Controlling plasmonic hot spots by interfering Airy beams, Optics Letters, Aug. 15, 2012, 37(16): 3402-4.
Korlach et al., Real-time DNA sequencing from single polymerase molecules. Methods Enzymol. May 2010;472:431-55. doi:10.1016/S0076-6879(10)72001-2.
Kreye et al, P-200: Evaluation of different OLED-Stacks for Active-Matrix OLED Microdisplays on CMOS-Substrates, SID 06 Digest, Jun. 2006, 37(1); 979-81.
Kumar et al., Terminal phosphate labeled nucleotides: synthesis, applications, and linker effect on incorporation by DNA polymerases. Nucleosides Nucleotides Nucleic Acids. Nov. 2005;24(5-7):401-8.
Lenne et al., Fluorescence fluctuations analysis in nanoapertures: physical concepts and biological applications, Histochem Cell Biol, Sep. 2008, 130:795-805.
Leslie et al., Convex Lens-Induced Confinement for Imaging Single Molecules, Anal. Chem., Jul. 15, 2010, 82(14):6224-9.
Levy et al., An 852x600 Pixel OLED-on-Silicon Color Microdisplay Using CMOS Subthreshold-Voltage-Scaling Current Drivers, IEEE Journal of Solid-State Circuits, Dec. 2002, 37(12): 1879-89.
Lezec et al., Beaming Light from a Subwavelength Aperture, Science, Aug. 2, 2002, 297(5582):820-2.
Li et al., Employing ~100% Excitons in OLEDs by Utilizing a Fluorescent Molecule with Hybridized Local and Charge-Transfer Excited State, Advanced Functional Materials, Mar. 19, 2014, 24(11):1609-14.
Lin et al., Cosine-Gauss Plasmon Beam: A Localized Long-Range Nondiffracting Surface Wave, Physical Review Letters, Aug. 31, 2012, 109(9):093904-1-5.
McGinty et al., Wide-field fluorescence lifetime imaging of cancer, Biomedical Optics Express, Sep. 1, 2010, 1(2): 627-40.
Misra et al., White organic LEDs and their recent advancements, Semiconductor Science and Technology, Apr. 25, 2006, 21(7):R35-47.
Mitchell et al., Nanosecond Fluorescence Lifetime Imaging with gated CCD detection and pulsed laser excitation, Photonic Research Systems Ltd., May 1, 2013, 13 pages, Newhaven East Sussex UK.
Murshid et al., Array of concentric CMOS photodiodes for detection and de-multiplexing of spatially modulated optical channels, Optics & Laser Technology, Sep. 2009, 41(6):764-9.
Murshid et al., CMOS Detectors: Concentric photodiode array enables spatial-domain multiplexing, Laser Focus World, Apr. 1, 2009, 10 pages, http://www.laserfocusworld.com/articles/print/volume-45/issue-4/features/cmos-detectors-concentric-photodiode-array-enables-spatial-domain-multiplexing.html, [last accessed Dec. 12, 2013].
Murshid et al., Concentric octagonal CMOS photodiodes for direct detection of spatially multiplexed optical fiber channels, Optical Society of America, Oct. 2008, 1 page.
Nozik, Multiple exciton generation in semiconductor quantum dots, Chemical Physics Letters, May 20, 2008, 457(1-3):3-11.
Park et al., A dual-modality optical coherence tomography and fluorescence lifetime imaging microscopy system for simultaneous morphological and biochemical tissue characterization, Biochemical Optics Express, Aug. 2, 2010, 1(1):186-200.
Pfeifer et al., Improved optical outcoupling of OLED microdisplays by nanostructured substrates, IEEE Semiconductor Conference Dresden, Sep. 27-18, 2011, 4 pages, Dresden, Germany.
Poddubny et al., Photonic quasicrystalline and aperiodic structures, Physica E: Low-dimensional Systems and Nanostructures, May 2010, 42(7): 1871-95.
Pons et al., Solution-phase single quantum dot fluorescence resonance energy transfer. J Am Chem Soc., Nov. 29, 2006;128(47):15324-31.
Pudavar, Fluorescence Lifetime Imaging (FILM), Leica Microsystems Inc., Oct. 25, 2009, 60 pages, Exton, PA.
Punj et al., Plasmonic antennas and zero-mode waveguides to enhance single molecule fluorescence detection and fluorescence correlation spectroscopy toward physiological concentrations. Wiley Interdiscip Rev Nanomed Nanobiotechnol. May-Jun. 2014;6(3):268-82. doi: 10.1002/wnan.1261. Epub Feb. 24, 2014.
Ramuz et al., Coupling light from an organic light emitting diode (OLED) into a single-mode waveguide: Toward monolithically integrated optical sensors, Journal of Applied Physics, Apr. 2009, 105(8):084508-1-7.
Ran et al., Design of a 16 gray scales 320 x 240 pixels OLED-on-silicon driving circuit, Journal of Semiconductors, Jan. 2009, 30(1):015010-1-4.
Reckziegel et al., Optical sensors based on monlithic integrated organic light-emitting diodes (OLEDs), Proceedings of SPIE Optical Sensors, Apr. 28, 2008, vol. 7003: 8 pages.
Richter et al., Bidirectional OLED microdisplay: Combining display and image sensor functionality into a monolithic CMOS chip, 2011 IEEE International Solid-State Circuits Conference Digest of Technical Papers (ISSCC), Feb. 20-24, 2011, 3 pages, San Francisco, CA.
Richter et al., OLED-on-CMOS based bidirectional microdisplay for near-to-eye and sensor applications, IEEE Semiconductor Conference Dresden, Sep. 27-28, 2011, 3 pages, Dresden, Germany.
Rigneault et al., Enhancement of Single-Molecule Fluorescence Detection in Subwavelength Apertures, Physical Review Letters, Sep. 9, 2005, 95(11): 117401-1-4.
Romero-Garcia et al., Silicon nitride back-end optics for biosensor applications, Proc. of SPIE Integrated Optics: Physics and Simulations, May 7, 2013, vol. 8781: 87810W-1-11.

(56) References Cited

OTHER PUBLICATIONS

Romero-Garcia et al., Visible wavelength silicon nitride focusing grating coupler with AlCu/TiN reflector. Optics Letters. Jul. 15, 2013, 38(14):2521-3.
Rui et al., Demonstration of beam steering via dipole-coupled plasmonic spiral antenna, Scientific Reports, Jul. 19, 2013, 7 pages.
Sakadzic et al., Multi-photon microscopy with a low-cost and highly efficient Cr:LiCAF laser, Optics Express, Dec. 8, 2008, 16(25):20848-63.
Salthouse et al., Development of a Time Domain Fluorimeter for Fluorescent Lifetime Multiplexing Analysis, IEEE Biomed Circuits Syst., Sep. 1, 2008, 2(3): 204-11.
Schalberger et al., 60.4: Distinguished Paper: A Fully Integrated 1 AMOLED Display Using Current Feedback Based on a Five Mask LTPS CMOS Process, SID 10 Digest, May 2010, 41(1): 905-8.
Schmidt, Direct Encapsulation of OLED on CMOS, Bio and Nano Packaging Techniques for Electron Devices, Jul. 17, 2012, Chapter 29, 581-99, Springer-Verlag Berling Heidelberg.
Siegfried et al., Gap Plasmons and Near-Field Enhancement in Closely Packed Sub-10 nm Gap Resonators, Nano Lett., Oct. 10, 2013, 13(11):5449-53.
Sorokina et al., Fluorescent Lifetime Trajectories of a Single Fluorophore Reveal Reaction Intermediates During Transcription Initiation, J. Am. Chem. Soc., Jul. 22, 2009, 131(28):9630-31.
Sorokina et al., Supporting Information for Fluorescent Lifetime Trajectories of a Single Fluorophore Reveal Reaction Intermediates During Transcription Initiation, J. Am. Chem. Soc., Jul. 22, 2009, 131(28):4 pages.
Sun et al., Fluorescence lifetime imaging microscopy (FLIM) for image guided surgery, Stanford Computer Optics, 2013, 2 pages, http://www.stanfordcomputeroptics.com/applications/life-science/flim-guided-surgery.html , [last accessed May 9, 2014].
Taitt et al., Evanescent wave fluorescence biosensors. Biosens Bioelectron. Jun. 2005;20(12):2470-87. Epub Dec. 8, 2004.
Takkellapati et al., Synthesis of aminomethyl- and bis-aminomethyl-fluorescein energy transfer terminators. Nucleosides Nucleotides Nucleic Acids. Dec. 2007;26(10-12):1467-70.
Toerker et al., Integration of Top-Emitting Organic Light Emitting Diodes on CMOS Substrates, Proc. of SPIE Organic Optoelectronics and Photonics III, Apr. 16, 2008, vol. 6999, 4 pages.
Toma et al., Compact surface plasmon-enhanced fluorescence biochip, Opt. Express Apr. 22, 2013, 21(8): 10121-10132.
Toma et al., Surface plasmon-coupled emission on plasmonic Bragg gratings, Optics Express, Jun. 18, 2012, 20(13):14042-53.
Uhring et al., 200 ps FWHM and 100 MHz Repetition Rate Ultrafast Gated Camera for Optical Medical Functional Imaging, Proc. of SPIE Optical Sensing and Detection II, May 9, 2012, vol. 8439, 10 pages.
Unfricht et al., Grating-coupled surface plasmon resonance: a cell and protein microarray platform. Proteomics. Nov. 2005;5(17):4432-42.
Vogel et al., OLED-on-CMOS Integration for Optoelectronic Sensor Applications, Proc. of SPIE Silicon Photonics II, Mar. 1, 2007, vol. 6477:8 pages.
Vogel et al., Optoelectronic Sensors based on OLED-on-CMOS, 2008 2nd European Conference & Exhibition on Integration Issues of Minaturized Systems—MOMS, MOEMS, ICS, and Electronic Components (SSI), Apr. 9-10, 2008, 3 pages, Barcelona, Spain.
Von Ketteler et al., Fluorescence Lifetime-Based Glucose Sensing using NADH, Proc. of SPIE Optical Diagnostics and Sensing XII: Toward Point-of-Care Diagnostics; and Design and Performance Validation of Phantoms Used in Conjunction with Optical Measurement of Tissue IV, Feb. 1, 2012, vol. 8229, 8 pages.
Walpole, Slab-coupled optical waveguide lasers: a review, Proc. SPIE Novel In-Plane Semiconductor Lasers III, May 11, 2004, vol. 5365, 124-32.
Wenger et al., Emission and excitation contributions to enhanced single molecule fluorescence by gold nanometric apertures, Optics Express, Mar. 3, 2008, 16(5):3008-20.
Wenger et al., Enhanced fluorescence from metal nanoapertures: physical characterizations and biophotonic applications, Proc. SPIE Plasmonics in Biology and Medicine VII, Feb. 16, 2010, 8 pages.
Wenger, Aperture optical antennas, Optical Antennas, Feb. 2013, 25pages, Cambridge University Press, Cambridge, UK.
Willoughby, Elastically Averaged Precision Alignment, Massachusetts Institute of Technology, Jun. 2005, 158 pages, Cambridge, MA.
Xiong et al., Aluminum nitrade as a new material for chip-scale optomechanics and nonlinear optics, New Journal of Physics, Sep. 17, 2012, 14: 21 pages.
Yan-Yan et al., OLED-on-silicon chip with new pixel circuit, J. Cent. South Univ., May 19, 2012(5):1276-82.
Yu et al., Light Propagation with Phase Discontinuities: Generalized Laws of Reflection and Refraction, Science, Oct. 21, 2011, 334 (6054):333-7.
Yuk et al. Analysis of immunoarrays using a gold grating-based dual mode surface plasmon-coupled emission (SPCE) sensor chip. Analyst. Jun. 7, 2012;137(11):2574-81. doi: 10.1039/c2an35143a. Epub Apr. 13, 2012.
Zhang et al., Continuous metal plasmonic frequency selective surfaces, Optics Express, Nov. 7, 2011, 19(23):23279-85.
Zhao et al., Plasmonic demultiplexer and guiding. ACS Nano. Nov. 23, 2010;4(11):6433-8. doi: 10.1021/nn101334a. Epub Oct. 6, 2010.
Zhu et al., Zero-Mode Waveguides for Single-Molecule Analysis, Annu. Rev. Biophys., Jun. 2012, 41:269-93.
Zong et al., Equivalent Circuit Model of Top-emitting OLED for the Designing of OLED-on-Silicon Microdisplay, Advanced Materials Research, Nov. 2011, 383-90:7037-42.
PCT/US2014/066014, Jan. 28, 2015, Invitation to Pay Additional Fees.
PCT/US2014/066014, Apr. 7, 2015, International Search Report and Written Opinion.
PCT/US2014/066014, May 26, 2016, International Preliminary Report on Patentability.
PCT/US2015/044360, Nov. 20, 2015, Invitation to Pay Additional Fees.
PCT/US2015/044360, Feb. 3, 2016, International Search Report and Written Opinion.
PCT/US2015/044378, Oct. 30, 2015, Invitation to Pay Additional Fees.
PCT/US2015/044378, Jan. 15, 2016, International Search Report and Written Opinion.
PCT/US2015/044379, Nov. 2, 2015, Invitation to Pay Additional Fees.
PCT/US2015/044379, Jan. 15, 2016, International Search Report and Written Opinion.
PCT/US2014/066013, Jan. 28, 2015, Invitation to Pay Additional Fees.
PCT/US2014/066013, Apr. 7, 2015, International Search Report and Written Opinion.
PCT/US2014/066013, May 26, 2016, International Preliminary Report on Patentability.
PCT/US2014/066010, Jan. 28, 2015, Invitation to Pay Additional Fees.
PCT/US2014/066010, Apr. 7, 2015, International Search Report and Written Opinion.
PCT/US2014/066010, May 26, 2016, International Preliminary Report on Patentability.
EP 15759983.8, Mar. 15, 2019, Extended European Search Report.
Extended European Search Report for European Application No. 18202357.2 dated Mar. 15, 2019.
Third Party Observations for European Application No. 15759983.8 dated Aug. 1, 2018.
International Search Report and Written Opinion for International Application No. PCT/US17/18278 dated Apr. 25, 2017.
U.S. Appl. No. 15/852,571, filed Dec. 22, 2017, Rothberg et al.
U.S. Appl. No. 16/446,708, filed Jun. 20, 2019, Thurston et al.
U.S. Appl. No. 16/550,841, filed Aug. 26, 2019, Rothberg et al.
U.S. Appl. No. 16/554,751, filed Aug. 29, 2019, Cipriany.
EP 17753881.6, Sep. 19, 2019, Extended European Search Report.
PCT/US2017/018278, Aug. 30, 2018, International Preliminary Report on Patentability.

(56) References Cited

OTHER PUBLICATIONS

PCT/US2017/068089, Mar. 27, 2018, International Search Report and Written Opinion.
PCT/US2019/038105, Sep. 16, 2019, Invitation to Pay Additional Fees.
International Search Report and Written Opinion for International Application No. PCT/US2019/038105 dated Nov. 26, 2019.
Invitation to Pay Additional Fees for International Application No. PCT/US2019/048824 dated Dec. 9, 2019.
Li et al., Time-Domain Fluorescence Lifetime Imaging Techniques Suitable for Solid-State Imaging Sensor Arrays. Sensors. 2012;12(12):5651-5653. DOI: 10.3390/s120505650.
PCT/US2019/038105, Nov. 26, 2019, International Search Report and Written Opinion.
PCT/US2019/048824, Dec. 9, 2019, Invitation to Pay Additional Fees.
Extended European Search Report for European Application No. 17753881.6 dated Sep. 19, 2019.
International Search Report and Written Opinion for International Application No. PCT/US2017/068089 dated Mar. 27, 2018.
International Preliminary Report on Patentability for International Application No. PCT/US2017/018278 dated Aug. 30, 2018.
Invitation to Pay Additional Fees for International Application No. PCT/US2019/038105 dated Sep. 16, 2019.
Sun et al., Fluorescence lifetime imaging microscopy for brain tumor image-guided surgery. Journal of Biomedical Optics. 2010;15(5):1-5.
Sun et al., Needle-compatible single fiber bundle image guide reflectance endoscope. JBO Letters. 2010;15(4):1-3.

\* cited by examiner

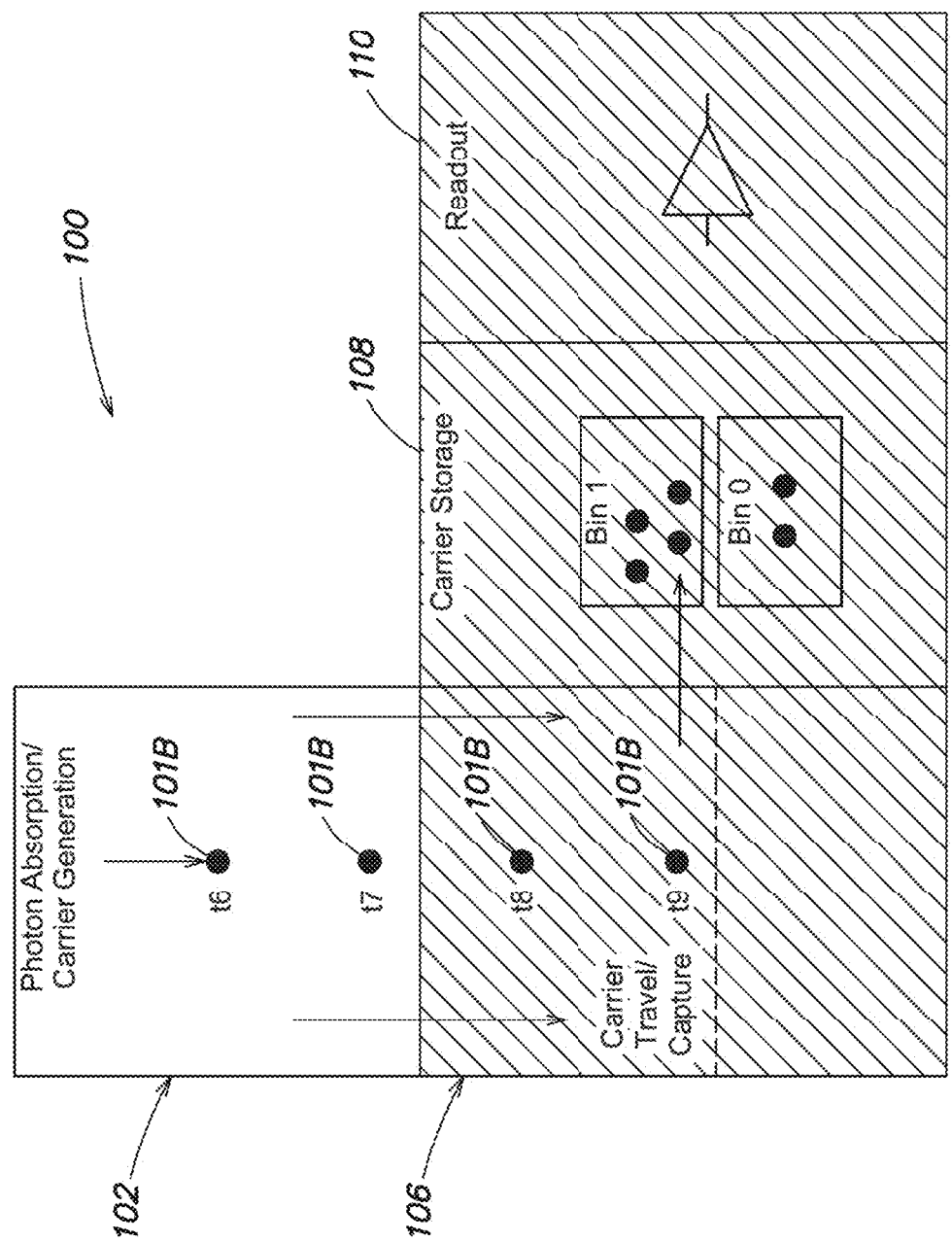

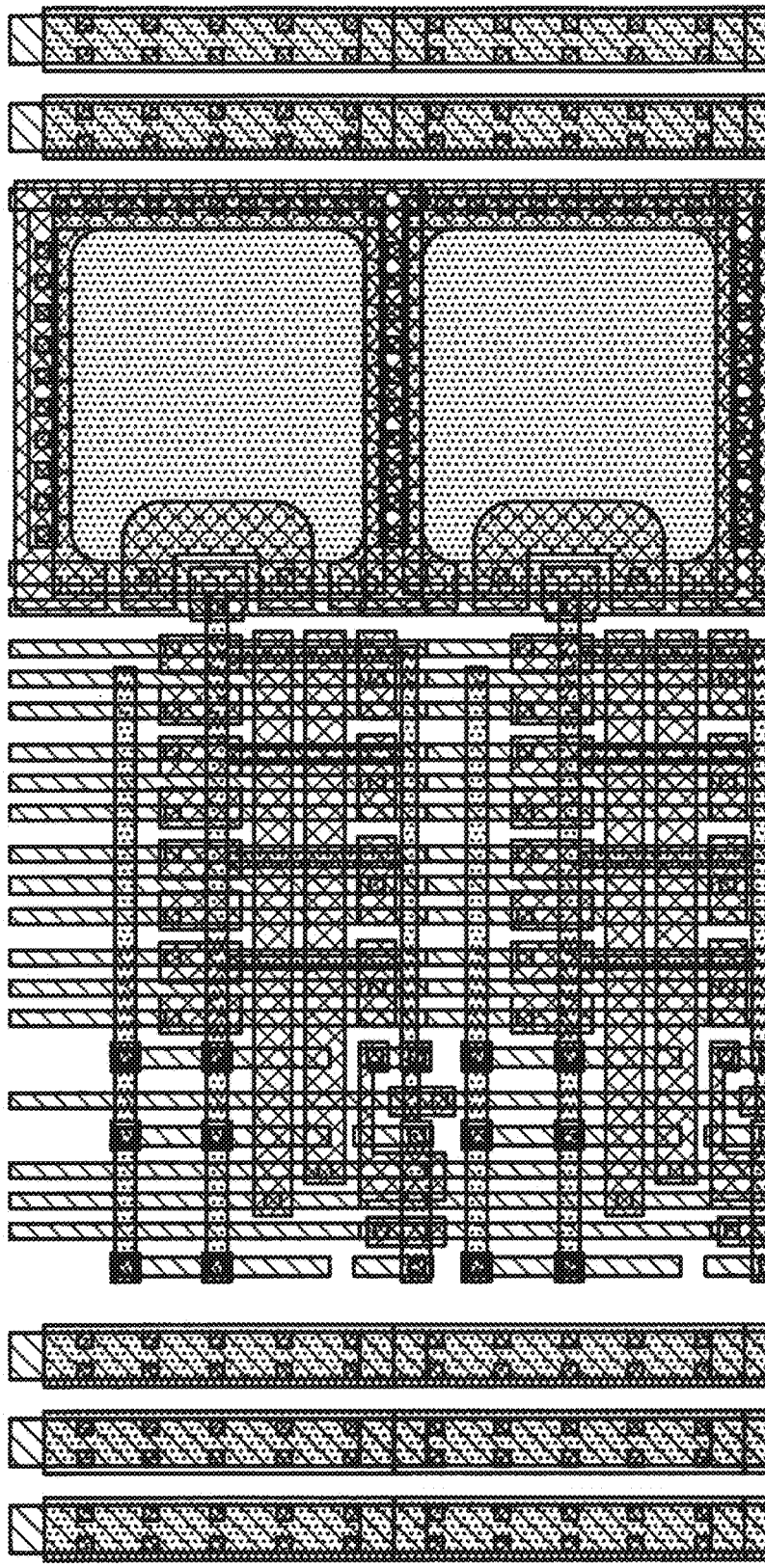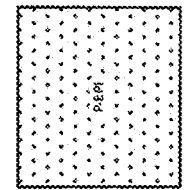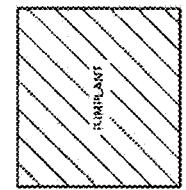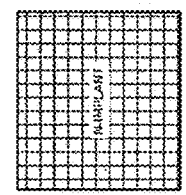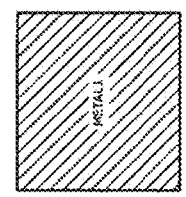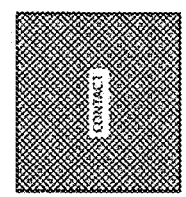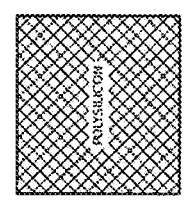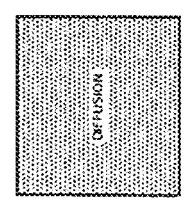
FIG. 3G

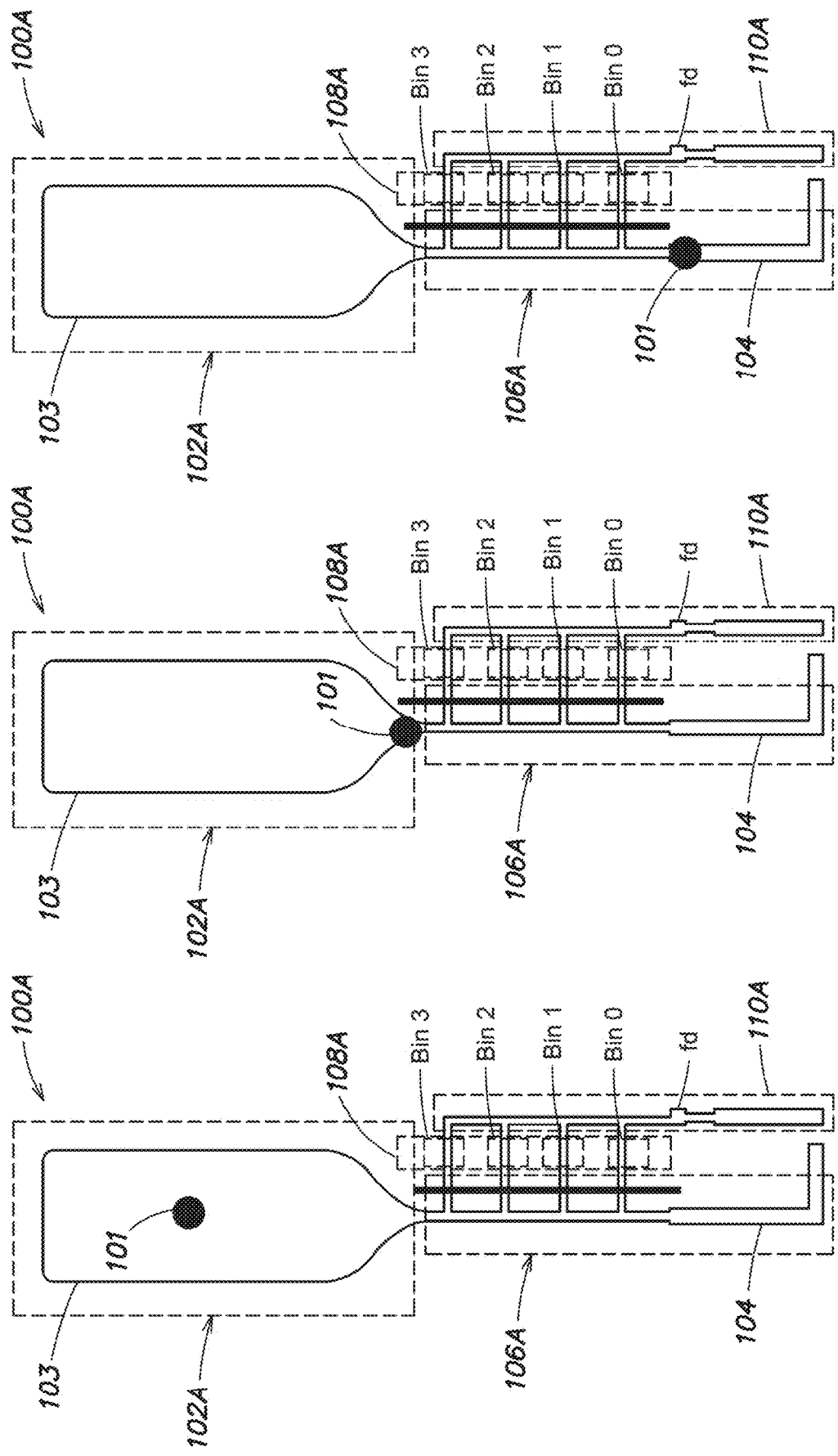

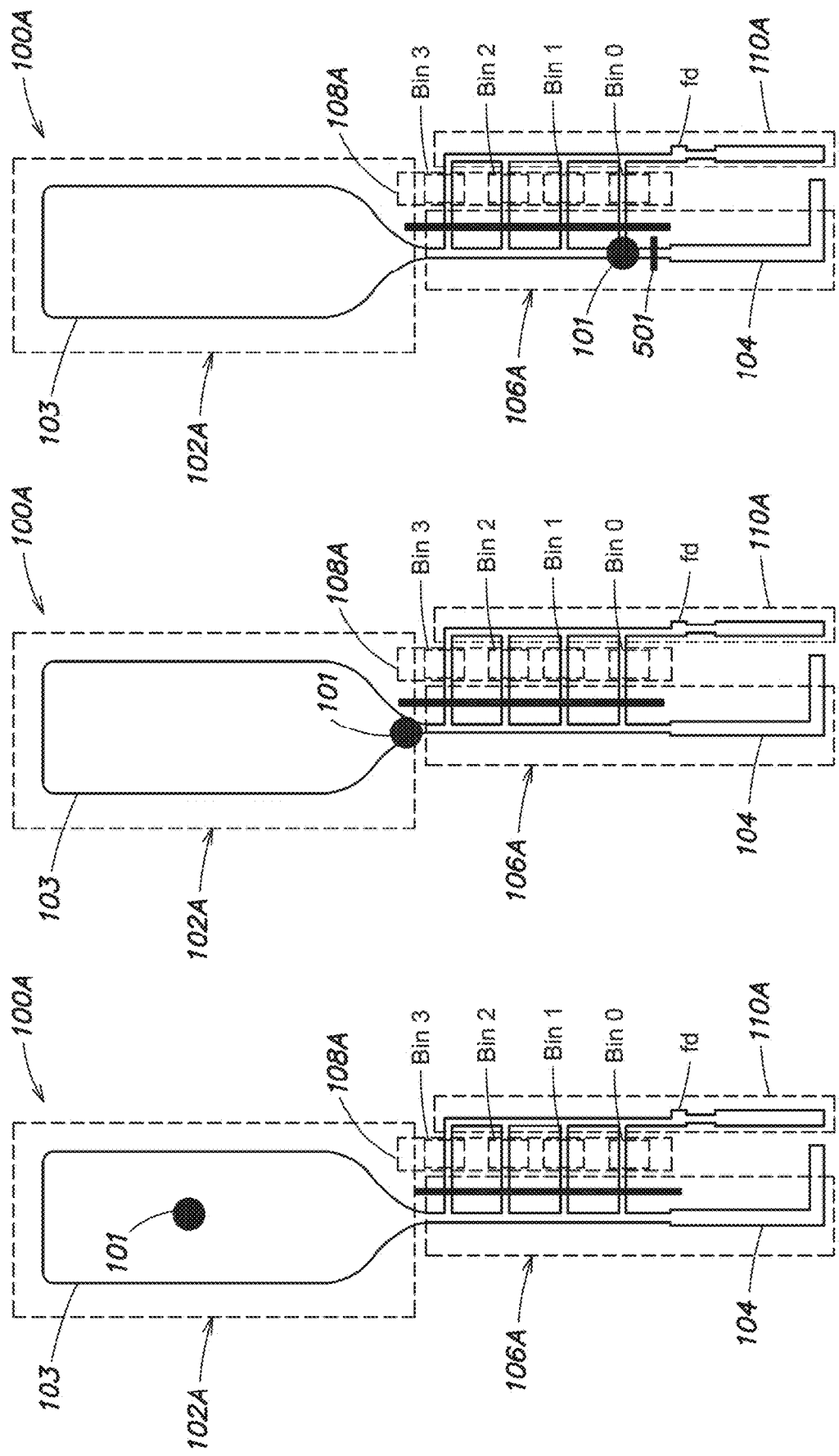

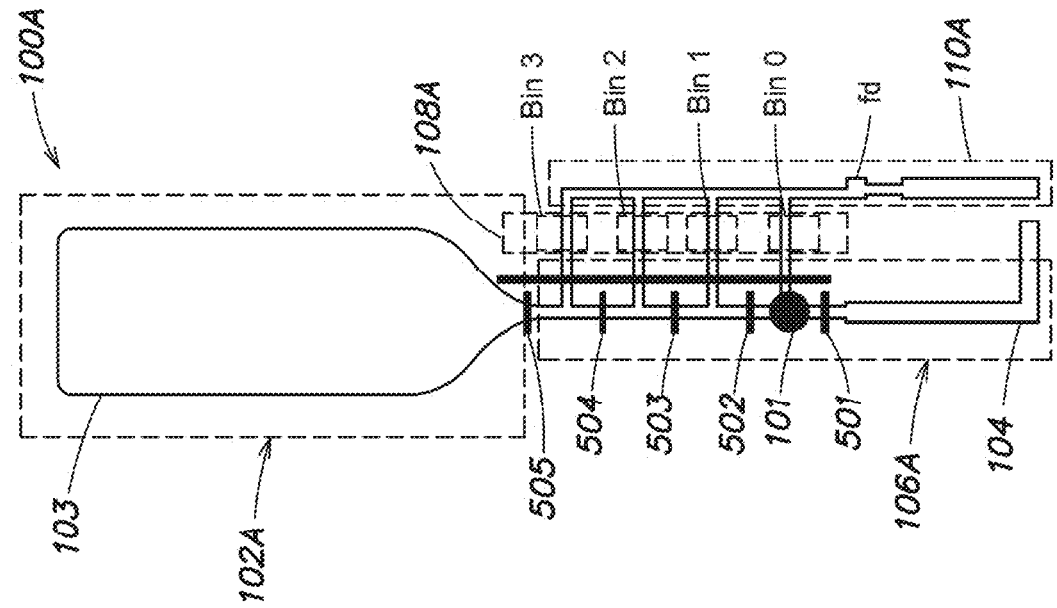
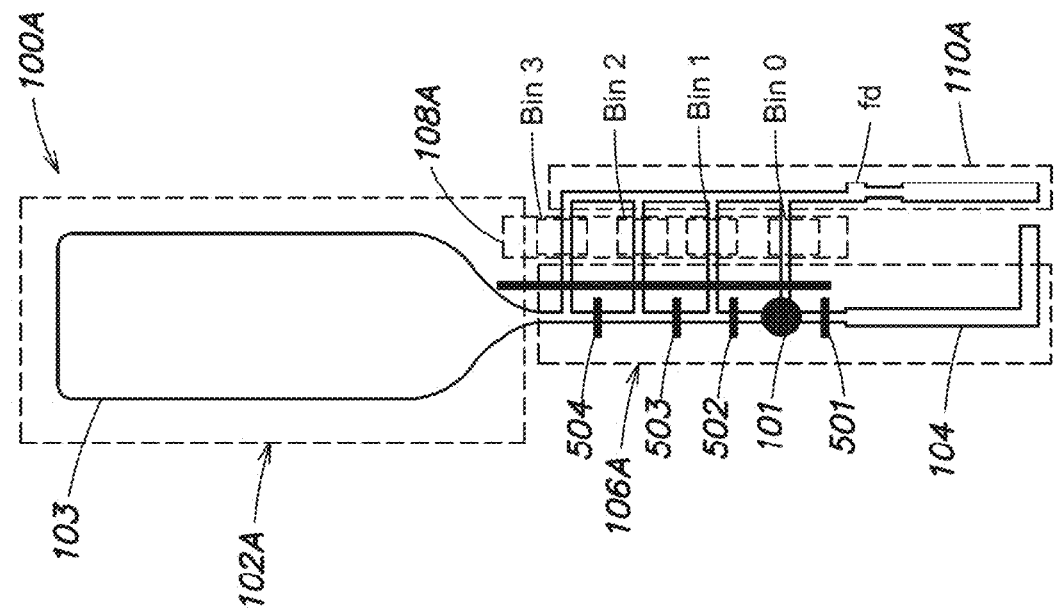

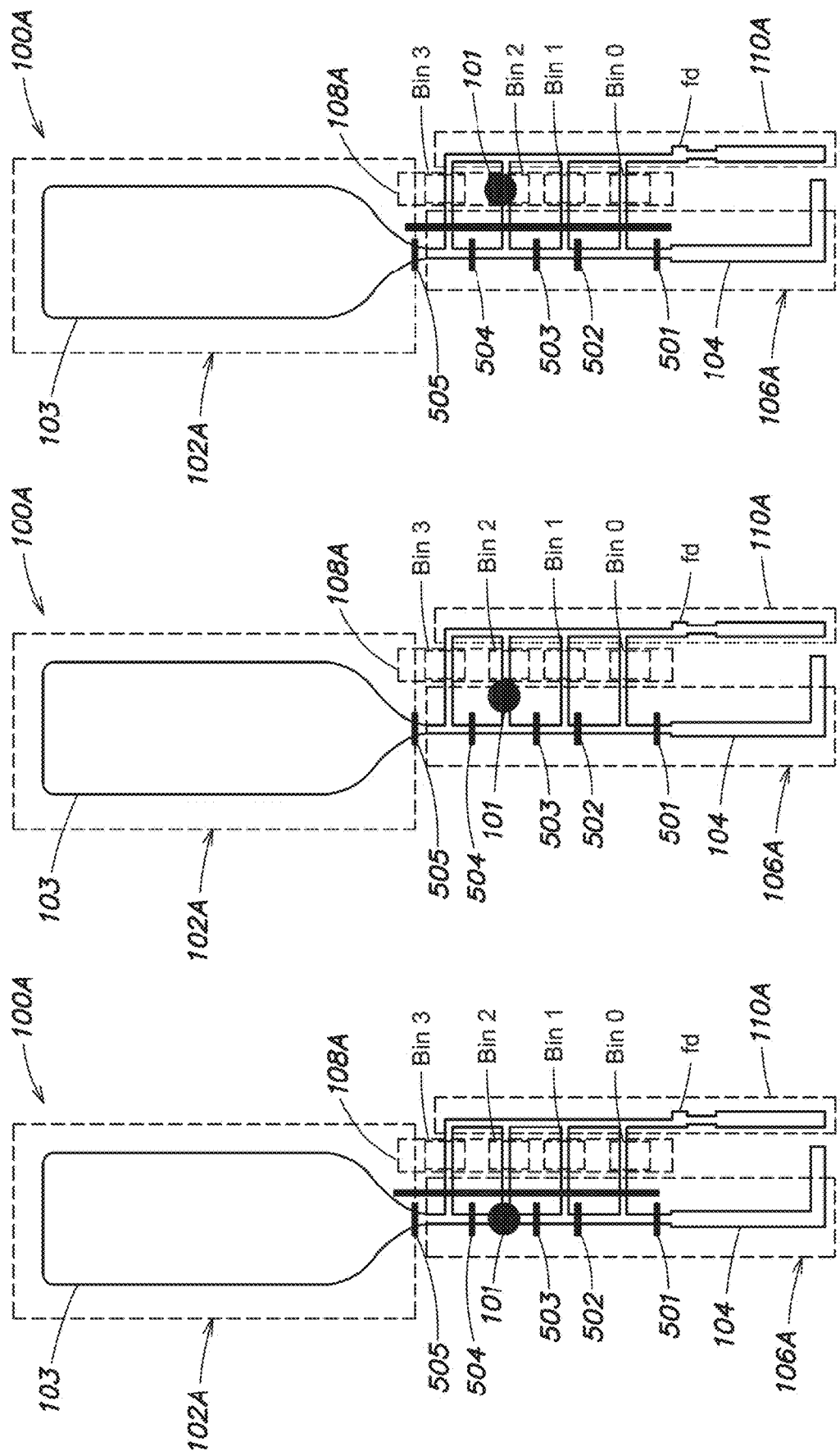

| Signal | V(Gradient Phase) | V(Binning Phase) | V(Transfer Phase) | V(Readout Phase) | Type |
|---|---|---|---|---|---|
| vb<0> | 0.0 | 0.0 | 0.0 | 0.0 | fixed |
| vb<11> | 3.1 | 3.1 | 3.1 | 3.1 | fixed |
| b<8> | 3.3 | 0.0 | 0.0 | 3.3 | 1:32 |
| b<7> | 3.5 | 3.5 | 0.0 | 3.5 | coarse |
| b<6> | 3.7 | 0.0 | 0.0 | 3.7 | 1:32 |
| b<5> | 3.9 | 3.9 | 0.0 | 3.9 | coarse |
| b<4> | 4.1 | 0.0 | 0.0 | 4.1 | 1:32 |
| b<3> | 4.3 | 4.3 | 0.0 | 4.3 | coarse |
| b<2> | 4.5 | 0.0 | 0.0 | 4.5 | 1:32 |
| b<1> | 4.7 | 4.7 | 0.0 | 4.7 | coarse |
| b<0> | 5.0 | 0.0 | 0.0 | 5.0 | 1:32 |
| st<0> | 0.0 | 0.0 | 5.0 | 0.0 | coarse |
| st<1> | 2.5 | 2.5 | 5.0 | 2.5 | coarse |
| tx<0> | 0.0 | 0.0 | 0.0 | 3.3 | FPGA |
| tx<1> | 0.0 | 0.0 | 0.0 | 3.3 | FPGA |
| tx<2> | 0.0 | 0.0 | 0.0 | 3.3 | FPGA |
| tx<3> | 0.0 | 0.0 | 0.0 | 3.3 | FPGA |
| rs | 0.0 | 0.0 | 0.0 | 3.3 | FPGA |
| rt | 0.0 | 0.0 | 0.0 | 3.3 | FPGA |
| PVDD | 3.3 | 3.3 | 3.3 | 3.3 | fixed |

FIG. 7H

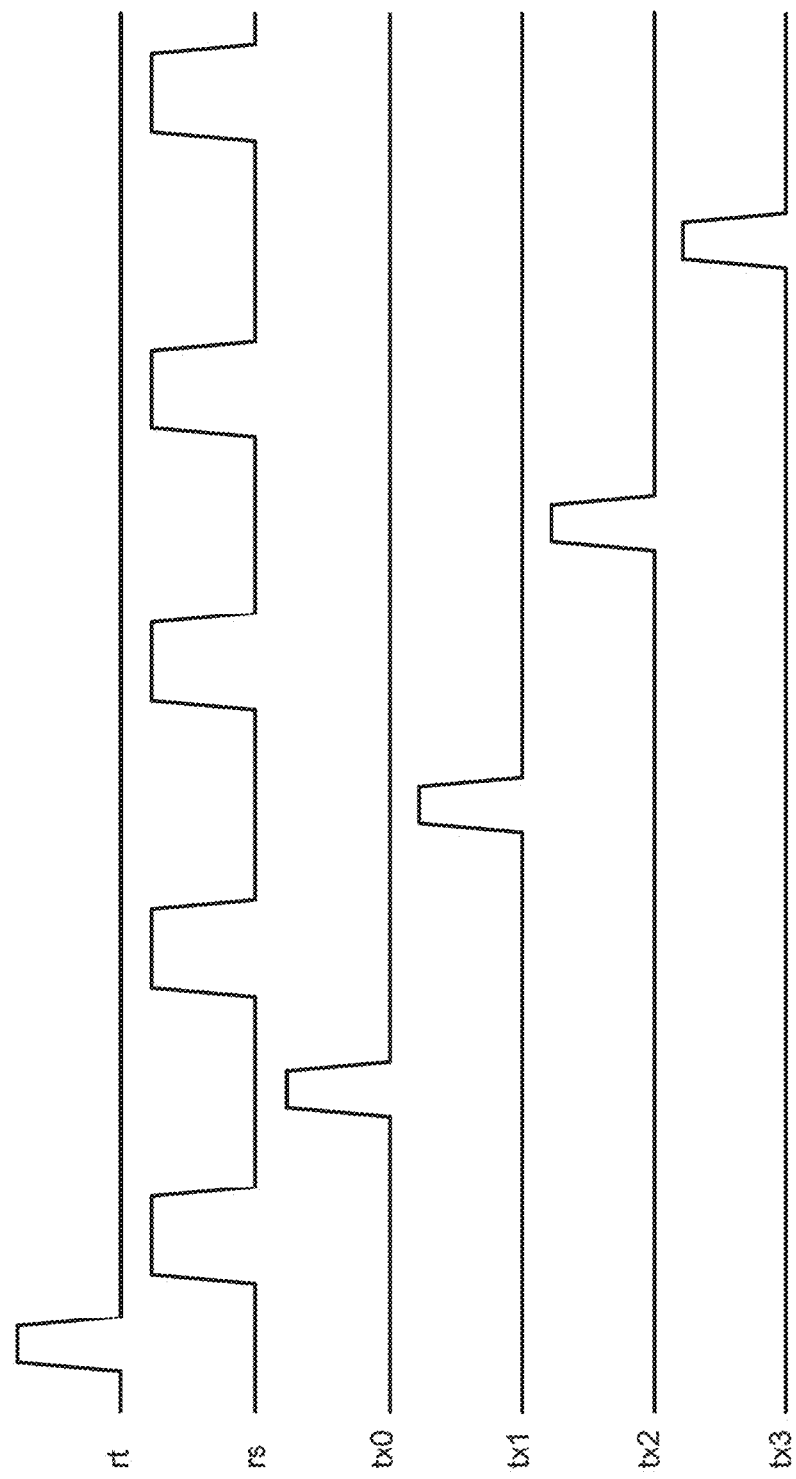

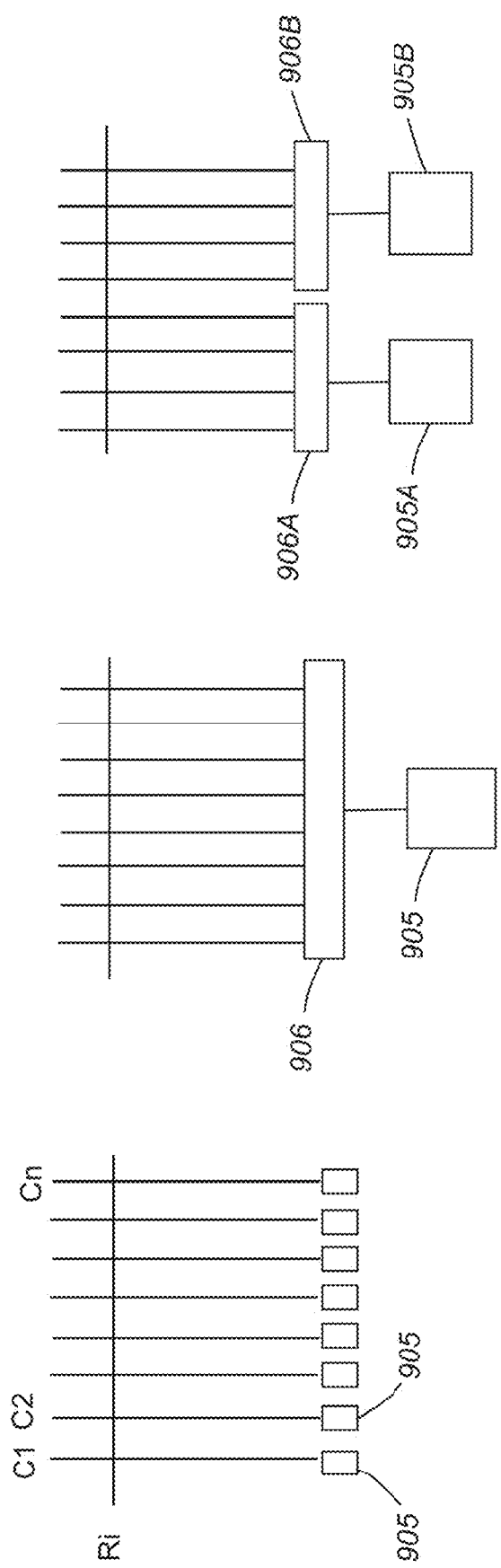

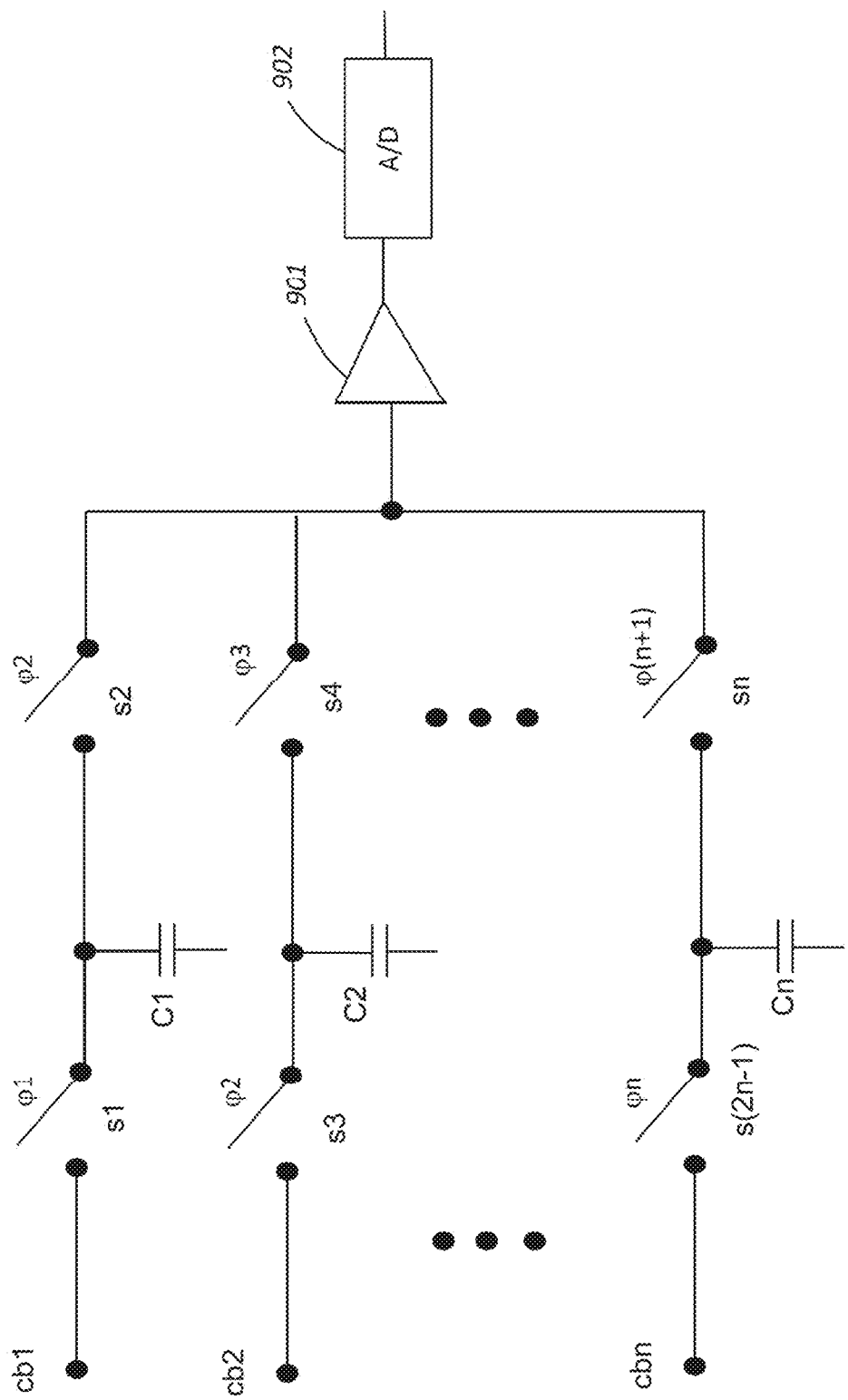

INTEGRATED DEVICE FOR TEMPORAL BINNING OF RECEIVED PHOTONS

CROSS-REFERENCE TO RELATED APPLICATIONS

This application is a continuation of U.S. patent application Ser. No. 15/656,139, filed Jul. 21, 2017, which is a continuation of U.S. patent application Ser. No. 14/821,656 (now U.S. Pat. No. 9,759,658), filed Aug. 7, 2015, which claims priority to U.S. Provisional Patent Application 62/164,506, filed May 20, 2015 and U.S. Provisional Patent 62/035,377, filed Aug. 8, 2014, each of which is hereby incorporated by reference in its entirety.

This application is related to the following U.S. applications:

U.S. Provisional Patent Application 62/035,258, entitled "INTEGRATED DEVICE WITH EXTERNAL LIGHT SOURCE FOR PROBING, DETECTING, AND ANALYZING MOLECULES," filed Aug. 8, 2014;

U.S. Provisional Patent Application 62/035,242, entitled "OPTICAL SYSTEM AND ASSAY CHIP FOR PROBING, DETECTING AND ANALYZING MOLECULES," filed Aug. 8, 2014

U.S. Provisional Patent Application 62/164,464, entitled "INTEGRATED DEVICE WITH EXTERNAL LIGHT SOURCE FOR PROBING, DETECTING, AND ANALYZING MOLECULES," filed May 20, 2015;

U.S. Provisional Patent Application 62/164,485, entitled "PULSED LASER", filed May 20, 2015;

U.S. Provisional Patent Application 62/164,482, entitled "METHODS FOR NUCLEIC ACID SEQUENCING", filed May 20, 2015;

U.S. Non-provisional patent application Ser. No. 14/821,686 (now U.S. Pat. No. 9,921,157), entitled "OPTICAL SYSTEM AND ASSAY CHIP FOR PROBING, DETECTING AND ANALYZING MOLECULES," filed Aug. 7, 2015; and U.S. Non-provisional patent application Ser. No. 14/821,688 (now U.S. Pat. No. 9,885,657), entitled "INTEGRATED DEVICE WITH EXTERNAL LIGHT SOURCE FOR PROBING, DETECTING, AND ANALYZING MOLECULES," filed Aug. 7, 2015.

Each of the above-listed related applications is hereby incorporated by reference in its entirety.

BACKGROUND

Photodetectors are used to detect light in a variety of applications. Integrated photodetectors have been developed that produce an electrical signal indicative of the intensity of incident light. Integrated photodetectors for imaging applications include an array of pixels to detect the intensity of light received from across a scene. Examples of integrated photodetectors include charge coupled devices (CCDs) and Complementary Metal Oxide Semiconductor (CMOS) image sensors.

SUMMARY

Some embodiments relate to an integrated circuit that includes a photodetection region configured to receive incident photons, the photodetection region being configured to produce a plurality of charge carriers in response to the incident photons. The integrated circuit also includes at least one charge carrier storage region. The integrated circuit also includes a charge carrier segregation structure configured to selectively direct charge carriers of the plurality of charge carriers into the at least one charge carrier storage region based upon times at which the charge carriers are produced.

Some embodiments relate to an integrated circuit that includes a photodetection region configured to receive incident photons, the photodetection region being configured to produce a plurality of charge carriers in response to the incident photons. The integrated circuit also includes at least one charge carrier storage region. The integrated circuit also includes means for selectively directing charge carriers of the plurality of charge carriers into the at least one charge carrier storage region based upon times at which the charge carriers are produced.

Some embodiments relate to a photodetection method, comprising receiving incident photons and selectively directing charge carriers of a plurality of charge carriers produced in response to the incident photons into at least one charge carrier storage region based upon times at which the charge carriers are produced.

Some embodiments relate to a computer readable storage medium having stored thereon instructions, which when executed by a processor, perform a photodetection method. The method includes controlling a charge carrier segregation structure to selectively direct charge carriers of a plurality of charge carriers produced in response to incident photons into at least one charge carrier storage region based upon times at which the charge carriers are produced.

Some embodiments relate to a method of forming an integrated circuit. The method includes forming a charge carrier confinement region comprising a photodetection region and a charge carrier travel region. The photodetection region is configured to produce a plurality of charge carriers in response to incident photons. The method also includes forming a charge carrier segregation structure configured to selectively direct charge carriers of the plurality of charge carriers into at least one charge carrier storage region based upon times at which the charge carriers are produced.

Some embodiments relate to a method of sequencing a nucleic acid. The method includes receiving photons from luminescent molecules attached, for at least a period of time, directly or indirectly, to respective nucleotides of the nucleic acid. The method also includes selectively directing charge carriers of a plurality of charge carriers produced in response to the incident photons into at least one charge carrier storage region based upon times at which the charge carriers are produced.

Some embodiments relate to a computer readable storage medium having stored thereon instructions, which when executed by a processor, perform a method of sequencing a nucleic acid. The method includes sequencing a nucleic acid using, at least in part, arrival times of incident photons detected by an integrated circuit that receives the photons from luminescent molecules connected to respective nucleotides of the nucleic acid.

Some embodiments relate to a method of sequencing a nucleic acid. The method includes, using an integrated circuit, detecting arrival times of incident photons from luminescent molecules connected to respective nucleotides of the nucleic acid. The method also includes identifying luminescent molecules using, at least in part, an integrated circuit that detects arrival times of incident photons from the luminescent molecules.

Some embodiments relate to a method of fluorescence lifetime imaging. The method includes producing an image indicating fluorescent lifetimes using, at least in part, an integrated circuit that detects arrival times of incident photons from fluorescent molecules.

Some embodiments relate to a method of time-of-flight imaging. The method includes receiving incident photons, and selectively directing charge carriers of a plurality of charge carriers produced in response to the incident photons into at least one charge carrier storage region based upon times at which the charge carriers are produced.

The foregoing summary is provided by way of illustration and is not intended to be limiting.

BRIEF DESCRIPTION OF DRAWINGS

In the drawings, each identical or nearly identical component that is illustrated in various figures is represented by a like reference character. For purposes of clarity, not every component may be labeled in every drawing. The drawings are not necessarily drawn to scale, with emphasis instead being placed on illustrating various aspects of the techniques and devices described herein FIG. 1A plots the probability of a photon being emitted as a function of time for two markers with different lifetimes.

FIG. 2B illustrates capturing a charge carrier at a different point in time and space than in FIG. 2A.

FIG. 3F indicates regions of diffusion, polysilicon, contact and metal 1.

FIG. 3G shows the pixel array of FIG. 3F and also indicates regions of diffusion, polysilicon, contact, metal 1, N-implant, P-implant, and P-epi.

FIG. 6A shows the position of a carrier once it is photogenerated.

FIG. 6B shows the position of a carrier shortly thereafter, as it travels in the downward direction in response to the established potential gradient.

FIG. 6C shows the position of the carrier as it reaches the drain.

FIG. 6D shows the position of a carrier (e.g., an electron) once it is photogenerated.

FIG. 6E shows the position of a carrier shortly thereafter, as it travels in the downward direction in response to the potential gradient.

FIG. 6F shows the position of the carrier as it reaches the potential barrier after time t1.

FIG. 6I shows an example in which an electron arrived between times t1 and t2, so it remains captured between potential barrier 501 and potential barrier 502.

FIG. 6J shows an example in which an electron arrived between times t1 and t2, so it remains captured between potential barrier 501 and potential barrier 502.

FIG. 7E shows a plan view illustrating an electron captured between potential barriers 503 and 504.

FIG. 7F shows a plan view illustrating the voltage of electrode st1 being raised and the carrier being transferred.

FIG. 7G shows a plan view illustrating the voltage electrode st1 being lowered and the carrier being captured in bin2.

FIG. 7H shows the characteristics of the electrodes of a charge carrier segregation structure, according to some embodiments.

FIG. 9B shows a readout sequence for performing correlated double sampling that does not require measuring a reset value for each signal value, according to some embodiments.

FIG. 10A illustrates an array of pixels having a plurality of columns C1 to Cn and a plurality of rows, with a selected row Ri being shown by way of illustration.

FIG. 10B shows an embodiment in which a common readout circuit may be provided for a plurality of columns.

FIG. 10C shows an embodiments with a plurality of readout circuits, fewer than the number of columns.

FIG. 10F shows an embodiment in which n columns of the pixel array share readout circuitry and/or an A/D converter.

DETAILED DESCRIPTION

Figure 1A:
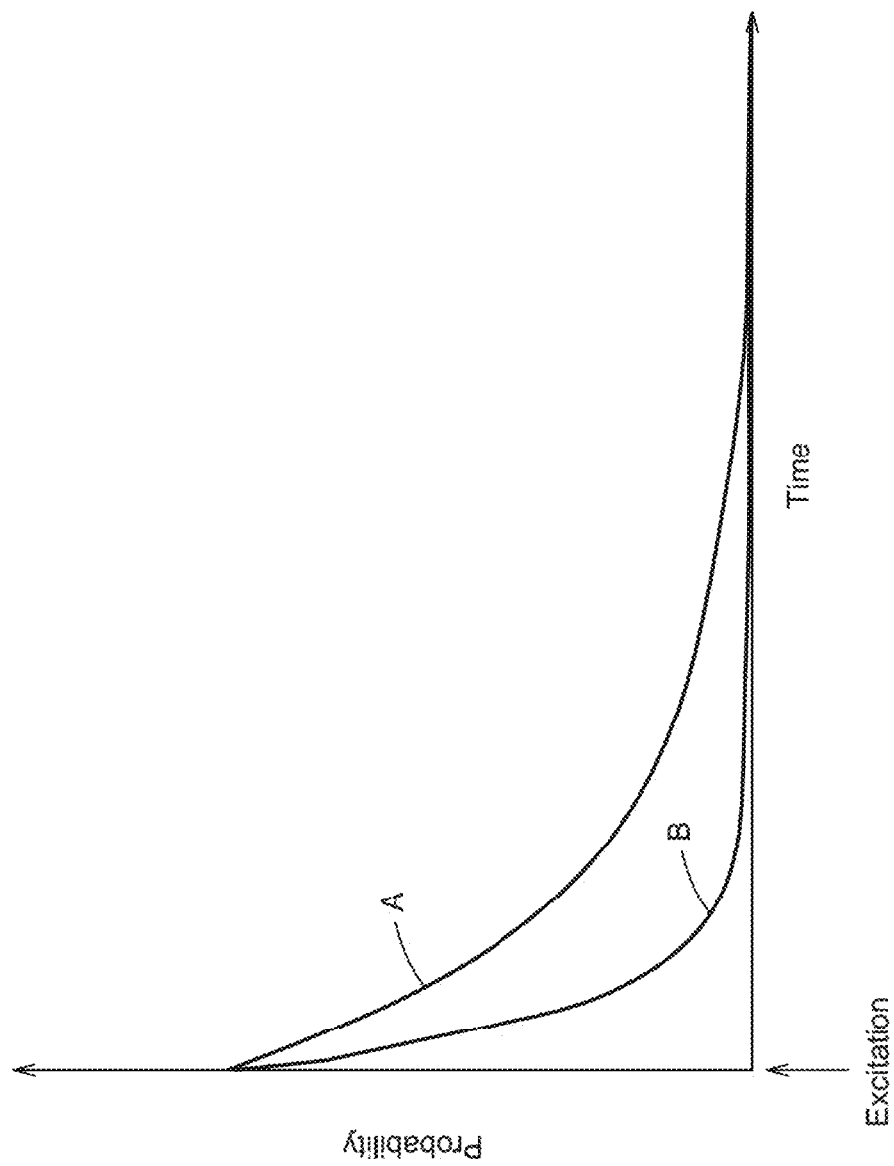
FIG. 1B shows example intensity profiles over time for an example excitation pulse (dotted line) and example fluorescence emission (solid line).

Described herein is an integrated photodetector that can accurately measure, or "time-bin," the timing of arrival of incident photons. In some embodiments, the integrated photodetector can measure the arrival of photons with nanosecond or picosecond resolution. Such a photodetector may find application in a variety of applications including molecular detection/quantiation, which may be applied to sequencing of nucleic acids (e.g., DNA sequencing). Such a photodetector can facilitate time-domain analysis of the arrival of incident photons from luminescent molecules used to label nucleotides, thereby enabling identification and sequencing of nucleotides based upon luminance lifetimes. Other examples of applications of the integrated photodetector include fluorescence lifetime imaging and time-of-flight imaging, as discussed further below.

Discussion of Time Domain Measurements for Molecular Detection/Quantitation

Detection and quantitation of biological samples may be performed using biological assays ("bioassays"). Bioassays conventionally involve large, expensive laboratory equipment requiring research scientists trained to operate the equipment and perform the bioassays. Bioassays are conventionally performed in bulk such that a large amount of a particular type of sample is necessary for detection and quantitation. Some bioassays are performed by tagging samples with luminescent markers that emit light of a particular wavelength. The samples are illuminated with a light source to cause luminescence, and the luminescent light is detected with a photodetector to quantify the amount of light emitted by the markers. Bioassays using luminescent tags and/or reporters conventionally involve expensive laser light sources to illuminate samples and complicated luminescent detection optics and electronics to collect the light from the illuminated samples.

In some embodiments, an integrated photodetector as described herein can detect the luminance characteristics of biological and/or chemical sample(s) in response to excitation. More specifically, such an integrated photodetector can detect the temporal characteristics of light received from the sample(s). Such an integrated photodetector can enable detecting and/or discriminating the luminance lifetime, e.g., the fluorescence lifetime, of light emitted by a luminescent molecule in response to excitation. In some embodiments, identification and/or quantitative measurements of sample(s) can be performed based on detecting and/or discriminating luminance lifetimes. For example, in some embodiments sequencing of a nucleic acid (e.g., DNA, RNA) may be performed by detecting and/or discriminating luminance lifetimes of luminescent molecules attached to respective nucleotides. Each luminescent molecule may be directly attached (e.g., bonded) to a corresponding nucleotide or indirectly attached to a corresponding nucleotide via a linker molecule that is bonded to the nucleotide and the luminescent molecule.

In some embodiments, an integrated photodetector having a number of photodetection structures and associated electronics, termed "pixels," can enable measurement and analysis of a plurality of samples in parallel (e.g., hundreds, thousands, millions or more), which can reduce the cost of performing complex measurements and rapidly advance the rate of discoveries. In some embodiments, each pixel of the photodetector may detect light from a sample, which may be a single molecule or more than one molecule. In some embodiments, such an integrated photodetector can be used for dynamic real time applications such as nucleic acid (e.g., DNA, RNA) sequencing.

Detection/Quantiation of Molecules Using Luminance Lifetimes

An integrated circuit having an integrated photodetector according to aspects of the present application may be designed with suitable functions for a variety of detection and imaging applications. As described in further detail below, such an integrated photodetector can have the ability to detect light within one or more time intervals, or "time bins." To collect information regarding the time of arrival of the light, charge carriers are generated in response to incident photons and can be segregated into respective time bins based upon their time of arrival.

An integrated photodetector according to some aspects of the present application may be used for differentiating among light emission sources, including luminescent molecules, such as fluorophores. Luminescent molecules vary in the wavelength of light they emit, the temporal characteristics of the light they emit (e.g., their emission decay time periods), and their response to excitation energy. Accordingly, luminescent molecules may be identified or discriminated from other luminescent molecules based on detecting these properties. Such identification or discrimination techniques may be used alone or in any suitable combination.

In some embodiments, an integrated photodetector as described in the present application can measure or discriminate luminance lifetimes, such as fluorescence lifetimes. Fluorescence lifetime measurements are based on exciting one or more fluorescent molecules, and measuring the time variation in the emitted luminescence. The probability of a fluorescent molecule to emit a photon after the fluorescent molecule reaches an excited state decreases exponentially over time. The rate at which the probability decreases may be characteristic of a fluorescent molecule, and may be different for different fluorescent molecules. Detecting the temporal characteristics of light emitted by fluorescent molecules may allow identifying fluorescent molecules and/or discriminating fluorescent molecules with respect to one another. Luminescent molecules are also referred to herein as luminescent markers, or simply "markers."

After reaching an excited state, a marker may emit a photon with a certain probability at a given time. The probability of a photon being emitted from an excited marker may decrease over time after excitation of the marker. The decrease in the probability of a photon being emitted over time may be represented by an exponential decay function $p(t) = e^{-t/\tau}$, where $p(t)$ is the probability of photon emission at a time, $t$, and $\tau$ is a temporal parameter of the marker. The temporal parameter $\tau$ indicates a time after excitation when the probability of the marker emitting a photon is a certain value. The temporal parameter, $\tau$, is a property of a marker that may be distinct from its absorption and emission spectral properties. Such a temporal parameter, $\tau$, is referred to as the luminance lifetime, the fluorescence lifetime or simply the "lifetime" of a marker.

FIG. 1A plots the probability of a photon being emitted as a function of time for two markers with different lifetimes. The marker represented by probability curve B has a probability of emission that decays more quickly than the probability of emission for the marker represented by probability curve A. The marker represented by probability curve B has a shorter temporal parameter, $\tau$, or lifetime than the marker represented by probability curve A. Markers may have fluorescence lifetimes ranging from 0.1-20 ns, in some embodiments. However, the techniques described herein are not limited as to the lifetimes of the marker(s) used.

The lifetime of a marker may be used to distinguish among more than one marker, and/or may be used to identify marker(s). In some embodiments, fluorescence lifetime measurements may be performed in which a plurality of markers having different lifetimes are excited by an excitation source. As an example, four markers having lifetimes of 0.5, 1, 2, and 3 nanoseconds, respectively, may be excited by a light source that emits light having a selected wavelength (e.g., 635 nm, by way of example). The markers may be identified or differentiated from each other based on measuring the lifetime of the light emitted by the markers.

Fluorescence lifetime measurements may use relative intensity measurements by comparing how intensity changes over time, as opposed to absolute intensity values. As a result, fluorescence lifetime measurements may avoid some of the difficulties of absolute intensity measurements. Absolute intensity measurements may depend on the concentration of fluorophores present and calibration steps may be needed for varying fluorophore concentrations. By contrast, fluorescence lifetime measurements may be insensitive to the concentration of fluorophores.

Luminescent markers may be exogenous or endogenous. Exogenous markers may be external luminescent markers used as a reporter and/or tag for luminescent labeling. Examples of exogenous markers may include fluorescent molecules, fluorophores, fluorescent dyes, fluorescent stains, organic dyes, fluorescent proteins, enzymes, and/or quantum dots. Such exogenous markers may be conjugated to a probe or functional group (e.g., molecule, ion, and/or ligand) that specifically binds to a particular target or component. Attaching an exogenous tag or reporter to a probe allows identification of the target through detection of the presence of the exogenous tag or reporter. Examples of probes may include proteins, nucleic acids such as DNA molecules or RNA molecules, lipids and antibody probes. The combination of an exogenous marker and a functional group may form any suitable probes, tags, and/or labels used for detection, including molecular probes, labeled probes, hybridization probes, antibody probes, protein probes (e.g., biotin-binding probes), enzyme labels, fluorescent probes, fluorescent tags, and/or enzyme reporters.

While exogenous markers may be added to a sample or region, endogenous markers may be already part of the sample or region. Endogenous markers may include any luminescent marker present that may luminesce or "auto-fluoresce" in the presence of excitation energy. Autofluorescence of endogenous fluorophores may provide for label-free and noninvasive labeling without requiring the introduction of endogenous fluorophores. Examples of such endogenous fluorophores may include hemoglobin, oxyhemoglobin, lipids, collagen and elastin crosslinks, reduced nicotinamide adenine dinucleotide (NADH), oxidized flavins (FAD and FMN), lipofuscin, keratin, and/or prophyrins, by way of example and not limitation.

Differentiating between markers by lifetime measurements may allow for fewer wavelengths of excitation light to be used than when the markers are differentiated by measurements of emission spectra. In some embodiments, sensors, filters, and/or diffractive optics may be reduced in number or eliminated when using fewer wavelengths of excitation light and/or luminescent light. In some embodiments, labeling may be performed with markers that have different lifetimes, and the markers may be excited by light having the same excitation wavelength or spectrum. In some embodiments, an excitation light source may be used that emits light of a single wavelength or spectrum, which may reduce the cost. However, the techniques described herein are not limited in this respect, as any number of excitation light wavelengths or spectra may be used. In some embodiments, an integrated photodetector may be used to determine both spectral and temporal information regarding received light. In some embodiments a quantitative analysis of the types of molecule(s) present may be performed by determining a temporal parameter, a spectral parameter, or a combination of the temporal and spectral parameters of the emitted luminescence from a marker.

An integrated photodetector that detects the arrival time of incident photons may reduce additional optical filtering (e.g., optical spectral filtering) requirements. As described below, an integrated photodetector according to the present application may include a drain to remove photogenerated carriers at particular times. By removing photogenerated carriers in this manner, unwanted charge carriers produced in response to an excitation light pulse may be discarded without the need for optical filtering to prevent reception of light from the excitation pulse. Such a photodetector may reduce overall design integration complexity, optical and/or filtering components, and/or cost.

In some embodiments, a fluorescence lifetime may be determined by measuring the time profile of the emitted luminescence by aggregating collected charge carriers in one or more time bins of the integrated photodetector to detect luminance intensity values as a function of time. In some embodiments, the lifetime of a marker may be determined by performing multiple measurements where the marker is excited into an excited state and then the time when a photon emits is measured. For each measurement, the excitation source may generate a pulse of excitation light directed to the marker, and the time between the excitation pulse and subsequent photon event from the marker may be determined. Additionally or alternatively, when an excitation pulse occurs repeatedly and periodically, the time between when a photon emission event occurs and the subsequent excitation pulse may be measured, and the measured time may be subtracted from the time interval between excitation pulses (i.e., the period of the excitation pulse waveform) to determine the time of the photon absorption event.

By repeating such experiments with a plurality of excitation pulses, the number of instances a photon is emitted from the marker within a certain time interval after excitation may be determined, which is indicative of the probability of a photon being emitted within such a time interval after excitation. The number of photon emission events collected may be based on the number of excitation pulses emitted to the marker. The number of photon emission events over a measurement period may range from 50-10,000,000 or more, in some embodiments, however, the techniques described herein are not limited in this respect. The number of instances a photon is emitted from the marker within a certain time interval after excitation may populate a histogram representing the number of photon emission events that occur within a series of discrete time intervals or time bins. The number of time bins and/or the time interval of each bin may be set and/or adjusted to identify a particular lifetime and/or a particular marker. The number of time bins and/or the time interval of each bin may depend on the sensor used to detect the photons emitted. The number of time bins may be 1, 2, 3, 4, 5, 6, 7, 8, or more, such as 16, 32, 64, or more. A curve fitting algorithm may be used to fit a curve to the recorded histogram, resulting in a function representing the probability of a photon to be emitted after excitation of the marker at a given time. An exponential decay function, such as $p(\tau) = e^{-t/\tau}$, may be used to approximately fit the histogram data. From such a curve fitting, the temporal parameter or lifetime may be determined. The determined lifetime may be compared to known lifetimes of markers to identify the type of marker present.

Figure 1B:
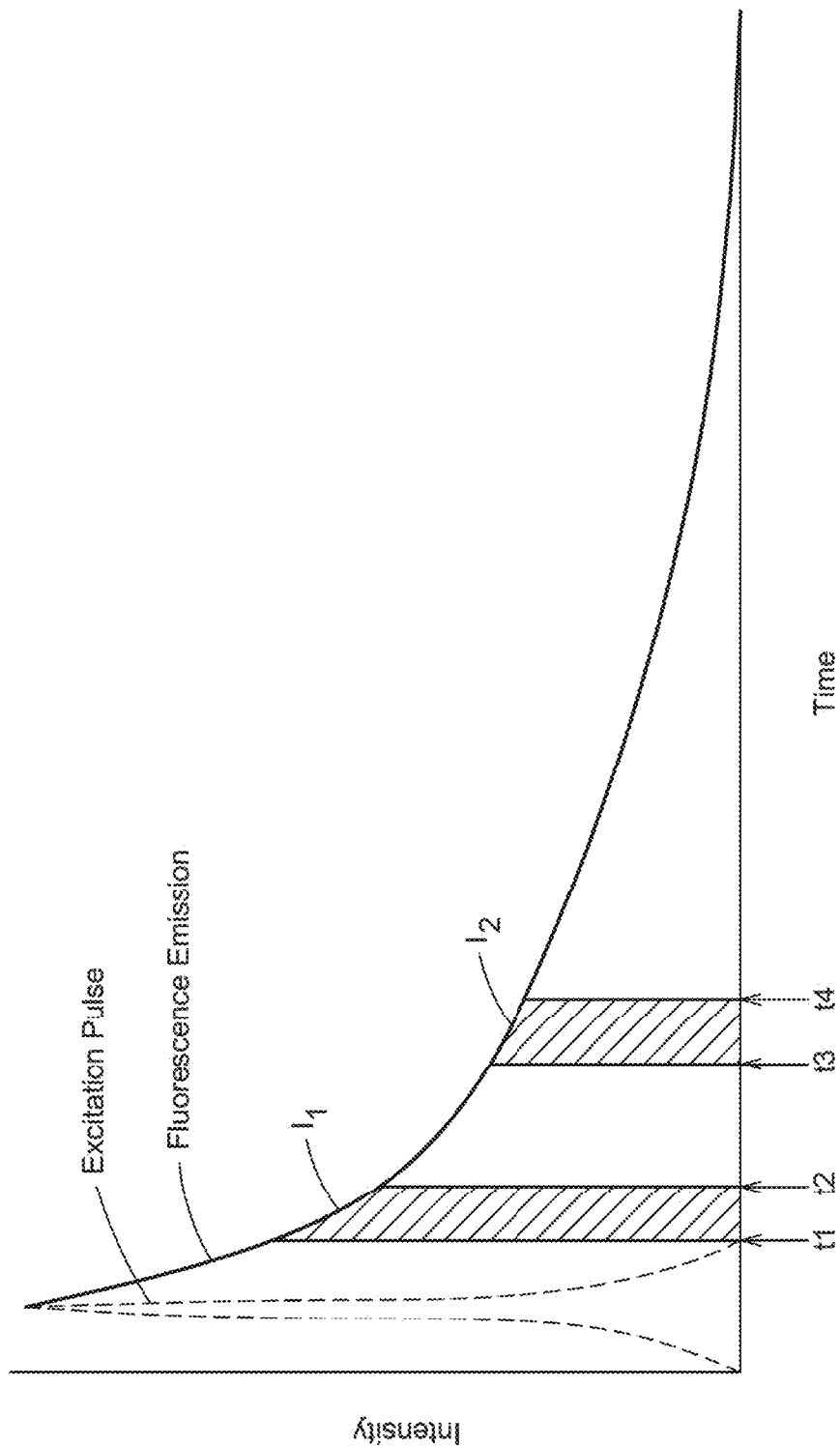

A lifetime may be calculated from the intensity values at two time intervals. FIG. 1B shows example intensity profiles over time for an example excitation pulse (dotted line) and example fluorescence emission (solid line). In the example shown in FIG. 1B, the photodetector measures the intensity over at least two time bins. The photons that emit luminescence energy between times t1 and t2 are measured by the photodetector as intensity I1 and luminescence energy emitted between times t3 and t4 are measured as I2. Any suitable number of intensity values may be obtained although only two are shown in FIG. 1B. Such intensity measurements may then be used to calculate a lifetime. When one fluorophore is present at a time, then the time binned luminescence signal may be fit to a single exponential decay. In some embodiments, only two time bins may be needed to accurately identify the lifetime for a fluorophore. When two or more fluorophores are present, then individual lifetimes may be identified from a combined luminescence signal by fitting the luminescence signal to multiple exponential decays, such as double or triple exponentials. In some embodiments two or more time bins may be needed in order to accurately identify more than one fluorescence lifetime from such a luminescence signal. However, in some instances with multiple fluorophores, an average fluorescence lifetime may be determined by fitting a single exponential decay to the luminescence signal.

In some instances, the probability of a photon emission event and thus the lifetime of a marker may change based on the surroundings and/or conditions of the marker. For example, the lifetime of a marker confined in a volume with a diameter less than the wavelength of the excitation light may be smaller than when the marker is not in the volume. Lifetime measurements with known markers under conditions similar to when the markers are used for labeling may be performed. The lifetimes determined from such measurements with known markers may be used when identifying a marker.

Sequencing Using Luminance Lifetime Measurements

Individual pixels on an integrated photodetector may be capable of fluorescence lifetime measurements used to identify fluorescent tags and/or reporters that label one or more targets, such as molecules or specific locations on molecules. Any one or more molecules of interest may be labeled with a fluorophore, including proteins, amino acids, enzymes, lipids, nucleotides, DNA, and RNA. When combined with detecting spectra of the emitted light or other labeling techniques, fluorescence lifetime may increase the total number of fluorescent tags and/or reporters that can be used. Identification based on lifetime may be used for single molecule analytical methods to provide information about characteristics of molecular interactions in complex mixtures where such information would be lost in ensemble averaging and may include protein-protein interactions, enzymatic activity, molecular dynamics, and/or diffusion on membranes. Additionally, fluorophores with different fluorescence lifetimes may be used to tag target components in various assay methods that are based on presence of a labeled component. In some embodiments, components may be separated, such as by using microfluidic systems, based on detecting particular lifetimes of fluorophores.

Measuring fluorescence lifetimes may be used in combination with other analytical methods. For an example, fluorescence lifetimes may be used in combination with fluorescence resonance energy transfer (FRET) techniques to discriminate between the states and/or environments of donor and acceptor fluorophores located on one or more molecules. Such measurements may be used to determine the distance between the donor and the acceptor. In some instances, energy transfer from the donor to the acceptor may decrease the lifetime of the donor. In another example, fluorescence lifetime measurements may be used in combination with DNA sequencing techniques where four fluorophores having different lifetimes may be used to label the four different nucleotides (A, T, G, C) in a DNA molecule with an unknown sequence of nucleotides. The fluorescence lifetimes, instead of emission spectra, of the fluorophores may be used to identify the sequence of nucleotides. By using fluorescence lifetime instead of emission spectra for certain techniques, accuracy and measurement resolution may increase because artifacts due to absolute intensity measurements are reduced. Additionally, lifetime measurements may reduce the complexity and/or expense of the system because fewer excitation energy wavelengths are required and/or fewer emission energy wavelengths need be detected.

The methods described herein may be used for sequencing of nucleic acids, such as DNA sequencing or RNA sequencing. DNA sequencing allows for the determination of the order and position of nucleotides in a target nucleic acid molecule. Technologies used for DNA sequencing vary greatly in the methods used to determine the nucleic acid sequence as well as in the rate, read length, and incidence of errors in the sequencing process. A number of DNA sequencing methods are based on sequencing by synthesis, in which the identity of a nucleotide is determined as the nucleotide is incorporated into a newly synthesized strand of nucleic acid that is complementary to the target nucleic acid. Many sequencing by synthesis methods require the presence of a population of target nucleic acid molecules (e.g., copies of a target nucleic acid) or a step of amplification of the target nucleic acid to achieve a population of target nucleic acids. Improved methods for determining the sequence of single nucleic acid molecules is desired.

There have been recent advances in sequencing single nucleic acid molecules with high accuracy and long read length. The target nucleic acid used in single molecule sequencing technology, for example the SMRT technology developed by Pacific Biosciences, is a single stranded DNA template that is added to a sample well containing at least one component of the sequencing reaction (e.g., the DNA polymerase) immobilized or attached to a solid support such as the bottom of the sample well. The sample well also contains deoxyribonucleoside triphosphates, also referred to a "dNTPs," including adenine, cytosine, guanine, and thymine dNTPs, that are conjugated to detection labels, such as fluorophores. Preferably each class of dNTPs (e.g. adenine dNTPs, cytosine dNTPs, guanine dNTPs, and thymine dNTPs) are each conjugated to a distinct detection label such that detection of the signal indicates the identity of the dNTP that was incorporated into the newly synthesized nucleic acid. The detection label may be conjugated to the dNTP at any position such that the presence of the detection label does not inhibit the incorporation of the dNTP into the newly synthesized nucleic acid strand or the activity of the polymerase. In some embodiments, the detection label is conjugated to the terminal phosphate (the gamma phosphate) of the dNTP.

Any polymerase may be used for single molecule DNA sequencing that is capable of synthesizing a nucleic acid complementary to a target nucleic acid. Examples of polymerases include *E. coli* DNA polymerase I, T7 DNA polymerase, bacteriophage T4 DNA polymerase φ29 (psi29) DNA polymerase, and variants thereof. In some embodiments, the polymerase is a single subunit polymerase. Upon base pairing between a nucleobase of a target nucleic acid and the complementary dNTP, the polymerase incorporates the dNTP into the newly synthesized nucleic acid strand by forming a phosphodiester bond between the 3' hydroxyl end of the newly synthesized strand and the alpha phosphate of the dNTP. In examples in which the detection label conjugated to the dNTP is a fluorophore, its presence is signaled by excitation and a pulse of emission is detected during the step of incorporation. For detection labels that are conjugated to the terminal (gamma) phosphate of the dNTP, incorporation of the dNTP into the newly synthesized strand results in release the beta and gamma phosphates and the detection label, which is free to diffuse in the sample well, resulting in a decrease in emission detected from the fluorophore.

The techniques described herein are not limited as to the detection or quantitation of molecules or other samples, or to performing sequencing. In some embodiments, an integrated photodetector may perform imaging to obtain spatial information regarding a region, object or scene and temporal information regarding the arrival of incident photons using the region, object or scene. In some embodiments, the integrated photodetector may perform luminescence lifetime imaging of a region, object or sample, such as fluorescence lifetime imaging.

Additional Applications

Although the integrated photodetector described herein may be applied to the analysis of a plurality of biological and/or chemical samples, as discussed above, the integrated photodetector may be applied to other applications, such as imaging applications, for example. In some embodiments, the integrated photodetector may include a pixel array that performs imaging of a region, object or scene, and may detect temporal characteristics of the light received at individual pixels from different regions of the region, object or scene. For example, in some embodiments the integrated photodetector may perform imaging of tissue based on the temporal characteristics of light received from the tissue, which may enable a physician performing a procedure (e.g., surgery) to identify an abnormal or diseased region of tissue (e.g., cancerous or pre-cancerous). In some embodiments, the integrated photodetector may be incorporated into a medical device, such as a surgical imaging tool. In some embodiments, time-domain information regarding the light emitted by tissue in response to a light excitation pulse may be obtained to image and/or characterize the tissue. For example, imaging and/or characterization of tissue or other objects may be performed using fluorescence lifetime imaging.

Although the integrated photodetector may be applied in a scientific or diagnostic context such as by performing imaging or analysis of biological and/or chemical samples, or imaging tissue, as described above, such an integrated photodetector may be used in any other suitable contexts. For example, in some embodiments, such an integrated photodetector may image a scene using temporal characteristics of the light detected in individual pixels. An example of an application for imaging a scene is range imaging or time-of-flight imaging, in which the amount of time light takes to reach the photodetector is analyzed to determine the distance traveled by the light to the photodetector. Such a technique may be used to perform three-dimensional imaging of a scene. For example, a scene may be illuminated with a light pulse emitted from a known location relative to the integrated photodetector, and the reflected light detected by the photodetector. The amount of time that the light takes to reach the integrated photodetector at respective pixels of the array is measured to determine the distance(s) light traveled from respective portions of the scene to reach respective pixels of the photodetector. In some embodiments, the integrated photodetector may be incorporated into a consumer electronic device such as a camera, cellular telephone, or tablet computer, for example, to enable such devices to capture and process images or video based on the range information obtained.

In some embodiments, the integrated photodetector described in the present application may be used to measure low light intensities. Such a photodetector may be suitable for applications that require photodetectors with a high sensitivity, such as applications that may currently use single photon counting techniques, for example. However, the techniques described herein are not limited in this respect, as the integrated photodetector described in the present applications may measure any suitable light intensities.

Additional Luminescence Lifetime Applications

Imaging and Characterization Using Lifetimes

As mentioned above, the techniques described herein are not limited to labeling, detection and quantitation using exogenous fluorophores. In some embodiments, a region, object or sample may be imaged and/or characterized using fluorescence lifetime imaging techniques though use of an integrated photodetector. In such techniques, the fluorescence characteristics of the region, object or sample itself may be used for imaging and/or characterization. Either exogenous markers or endogenous markers may be detected through lifetime imaging and/or characterization. Exogenous markers attached to a probe may be provided to the region, object, or sample in order to detect the presence and/or location of a particular target component. The exogenous marker may serve as a tag and/or reporter as part of a labeled probe to detect portions of the region, object, or sample that contains a target for the labeled probe. Autofluorescence of endogenous markers may provide a label-free and noninvasive contrast for spatial resolution that can be readily utilized for imaging without requiring the introduction of endogenous markers. For example, autofluorescence signals from biological tissue may depend on and be indicative of the biochemical and structural composition of the tissue.

Fluorescence lifetime measurements may provide a quantitative measure of the conditions surrounding the fluorophore. The quantitative measure of the conditions may be in addition to detection or contrast. The fluorescence lifetime for a fluorophore may depend on the surrounding environment for the fluorophore, such as pH or temperature, and a change in the value of the fluorescence lifetime may indicate a change in the environment surrounding the fluorophore. As an example, fluorescence lifetime imaging may map changes in local environments of a sample, such as in biological tissue (e.g., a tissue section or surgical resection). Fluorescence lifetime measurements of autofluorescence of endogenous fluorophores may be used to detect physical and metabolic changes in the tissue. As examples, changes in tissue architecture, morphology, oxygenation, pH, vascularity, cell structure and/or cell metabolic state may be detected by measuring autofluorescence from the sample and determining a lifetime from the measured autofluorescence. Such methods may be used in clinical applications, such as screening, image-guided biopsies or surgeries, and/or endoscopy. In some embodiments, an integrated photodetector of the present application may be incorporated into a clinical tool, such as a surgical instrument, for example, to perform fluorescence lifetime imaging. Determining fluorescence lifetimes based on measured autofluorescence provides clinical value as a label-free imaging method that allows a clinician to quickly screen tissue and detect small cancers and/or pre-cancerous lesions that are not apparent to the naked eye. Fluorescence lifetime imaging may be used for detection and delineation of malignant cells or tissue, such as tumors or cancer cells which emit luminescence having a longer fluorescence lifetime than healthy tissue. For example, fluorescence lifetime imaging may be used for detecting cancers on optically accessible tissue, such as gastrointestinal tract, bladder, skin, or tissue surface exposed during surgery.

In some embodiments, fluorescence lifetimes may be used for microscopy techniques to provide contrast between different types or states of samples. Fluorescence lifetime imaging microscopy (FLIM) may be performed by exciting a sample with a light pulse, detecting the fluorescence signal as it decays to determine a lifetime, and mapping the decay time in the resulting image. In such microscopy images, the pixel values in the image may be based on the fluorescence lifetime determined for each pixel in the photodetector collecting the field of view.

Imaging a Scene or Object Using Temporal Information

As discussed above, an integrated photodetector as described in the present application may be used in scientific and clinical contexts in which the timing of light emitted may be used to detect, quantify, and or image a region, object or sample. However, the techniques described herein are not limited to scientific and clinical applications, as the integrated photodetector may be used in any imaging application that may take advantage of temporal information regarding the time of arrival of incident photons. An example of an application is time-of-flight imaging.

Time-of-Flight Applications

In some embodiments, an integrated photodetector may be used in imaging techniques that are based on measuring a time profile of scattered or reflected light, including time-of-flight measurements. In such time-of-flight measurements, a light pulse may be is emitted into a region or sample and scattered light may be detected by the integrated photodetector. The scattered or reflected light may have a distinct time profile that may indicate characteristics of the region or sample. Backscattered light by the sample may be detected and resolved by their time of flight in the sample. Such a time profile may be a temporal point spread function (TPSF). The time profile may be acquired by measuring the integrated intensity over multiple time bins after the light pulse is emitted. Repetitions of light pulses and accumulating the scattered light may be performed at a certain rate to ensure that all the previous TPSF is completely extinguished before generating a subsequent light pulse. Time-resolved diffuse optical imaging methods may include spectroscopic diffuse optical tomography where the light pulse may be infrared light in order to image at a further depth in the sample. Such time-resolved diffuse optical imaging methods may be used to detect tumors in an organism or in part of an organism, such as a person's head.

Additionally or alternatively, time-of-flight measurements may be used to measure distance or a distance range based on the speed of light and time between an emitted light pulse and detecting light reflected from an object. Such time-of-flight techniques may be used in a variety of applications including cameras, proximity detection sensors in automobiles, human-machine interfaces, robotics and other applications that may use three-dimensional information collected by such techniques.

Integrated Photodetector for Time Binning Photogenerated Charge Carriers

Some embodiments relate to an integrated circuit having a photodetector that produces charge carriers in response to incident photons and which is capable of discriminating the timing at which the charge carriers are generated by the arrival of incident photons with respect to a reference time (e.g., a trigger event). In some embodiments, a charge carrier segregation structure segregates charge carriers generated at different times and directs the charge carriers into one or more charge carrier storage regions (termed "bins") that aggregate charge carriers produced within different time periods. Each bin stores charge carriers produced within a selected time interval. Reading out the charge stored in each bin can provide information about the number of photons that arrived within each time interval. Such an integrated circuit can be used in any of a variety of applications, such as those described herein.

An example of an integrated circuit having a photodetection region and a charge carrier segregation structure will be described. In some embodiments, the integrated circuit may include an array of pixels, and each pixel may include one or more photodetection regions and one or more charge carrier segregation structures, as discussed below.

Overview of Pixel Structure and Operation

Figure 2A:
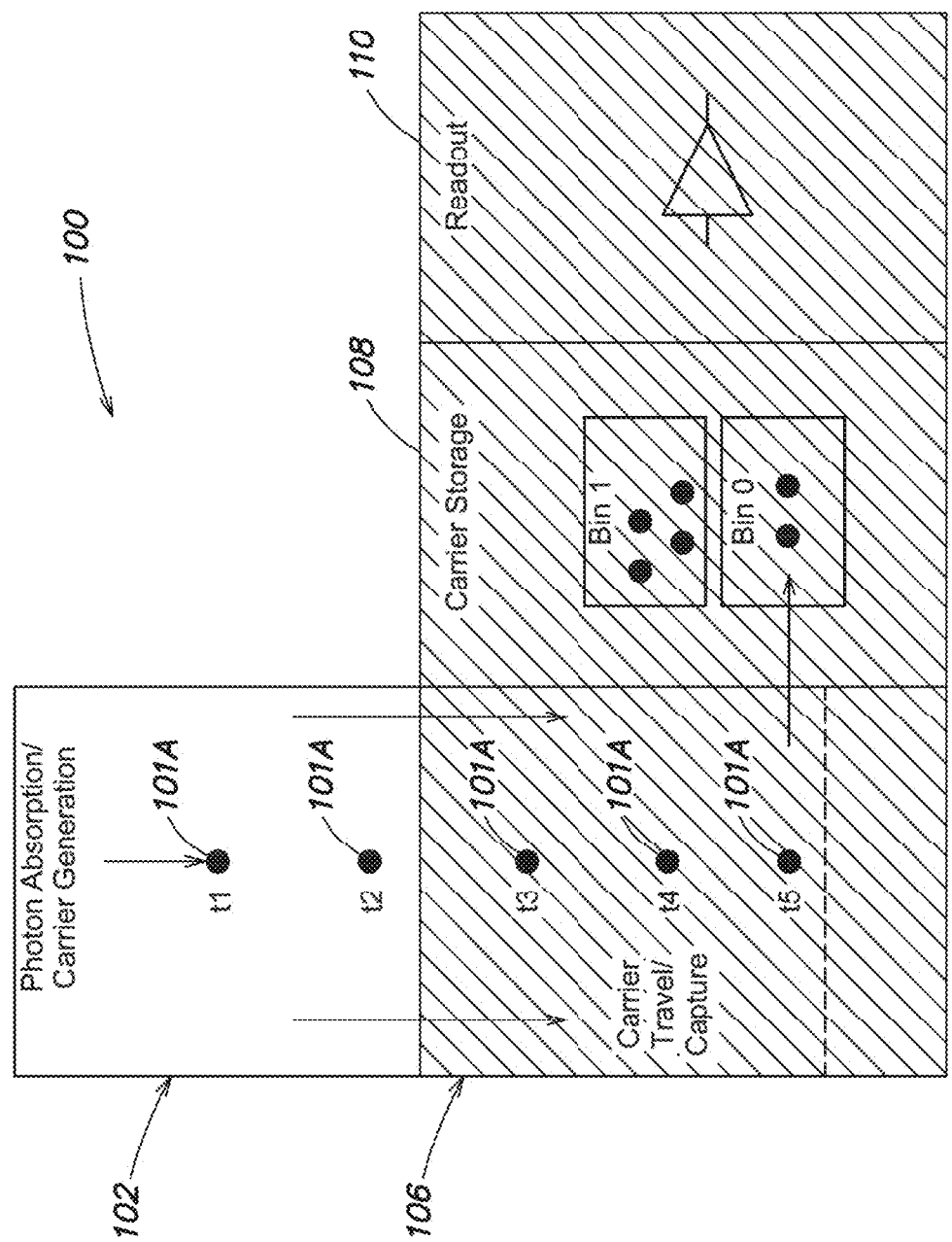
FIG. 2A shows a diagram of a pixel of an integrated photodetector, according to some embodiments.

FIG. 2A shows a diagram of a pixel 100, according to some embodiments. Pixel 100 includes a photon absorption/carrier generation region 102 (also referred to as a photodetection region), a carrier travel/capture region 106, a carrier storage region 108 having one or more charge carrier storage regions, also referred to herein as "charge carrier storage bins" or simply "bins," and readout circuitry 110 for reading out signals from the charge carrier storage bins.

The photon absorption/carrier generation region 102 may be a region of semiconductor material (e.g., silicon) that can convert incident photons into photogenerated charge carriers. The photon absorption/carrier generation region 102 may be exposed to light, and may receive incident photons. When a photon is absorbed by the photon absorption/carrier generation region 102 it may generate photogenerated charge carriers, such as an electron/hole pair. Photogenerated charge carriers are also referred to herein simply as "charge carriers."

An electric field may be established in the photon absorption/carrier generation region 102. In some embodiments, the electric field may be "static," as distinguished from the changing electric field in the carrier travel/capture region 106. The electric field in the photon absorption/carrier generation region 102 may include a lateral component, a vertical component, or both a lateral and a vertical component. The lateral component of the electric field may be in the downward direction of FIG. 2A, as indicated by the arrows, which induces a force on photogenerated charge carriers that drives them toward the carrier travel/capture region 106. The electric field may be formed in a variety of ways.

In some embodiments one or more electrodes may be formed over the photon absorption/carrier generation region 102. The electrodes(s) may have voltages applied thereto to establish an electric field in the photon absorption/carrier generation region 102. Such electrode(s) may be termed "photogate(s)." In some embodiments, photon absorption/carrier generation region 102 may be a region of silicon that is fully depleted of charge carriers.

In some embodiments, the electric field in the photon absorption/carrier generation region 102 may be established by a junction, such as a PN junction. The semiconductor material of the photon absorption/carrier generation region 102 may be doped to form the PN junction with an orientation and/or shape that produces an electric field that induces a force on photogenerated charge carriers that drives them toward the carrier travel/capture region 106. Producing the electric field using a junction may improve the quantum efficiency with respect to use of electrodes overlying the photon absorption/carrier generation region 102 which may prevent a portion of incident photons from reaching the photon absorption/carrier generation region 102. Using a junction may reduce dark current with respect to use of photogates. It has been appreciated that dark current may be generated by imperfections at the surface of the semiconductor substrate that may produce carriers. In some embodiments, the P terminal of the PN junction diode may connected to a terminal that sets its voltage. Such a diode may be referred to as a "pinned" photodiode. A pinned photodiode may promote carrier recombination at the surface, due to the terminal that sets its voltage and attracts carriers, which can reduce dark current. Photogenerated charge carriers that are desired to be captured may pass underneath the recombination area at the surface. In some embodiments, the lateral electric field may be established using a graded doping concentration in the semiconductor material.

In some embodiments, a absorption/carrier generation region 102 that has a junction to produce an electric field may have one or more of the following characteristics:
1) a depleted n-type region that is tapered away from the time varying field,
2) a p-type implant surrounding the n-type region with a gap to transition the electric field laterally into the n-type region, and/or
3) a p-type surface implant that buries the n-type region and serves as a recombination region for parasitic electrons.

In some embodiments, the electric field may be established in the photon absorption/carrier generation region 102 by a combination of a junction and at least one electrode. For example, a junction and a single electrode, or two or more electrodes, may be used. In some embodiments, one or more electrodes may be positioned near carrier travel/capture region 106 to establish the potential gradient near carrier travel/capture region 106, which may be positioned relatively far from the junction.

As illustrated in FIG. 2A, a photon may be captured and a charge carrier 101A (e.g., an electron) may be produced at time t1. In some embodiments, an electrical potential gradient may be established along the photon absorption/carrier generation region 102 and the carrier travel/capture region 106 that causes the charge carrier 101A to travel in the downward direction of FIG. 2A (as illustrated by the arrows shown in FIG. 2A). In response to the potential gradient, the charge carrier 101A may move from its position at time t1 to a second position at time t2, a third position at time t3, a fourth position at time t4, and a fifth position at time t5. The charge carrier 101A thus moves into the carrier travel/capture region 106 in response to the potential gradient.

The carrier travel/capture region 106 may be a semiconductor region. In some embodiments, the carrier travel/capture region 106 may be a semiconductor region of the same material as photon absorption/carrier generation region 102 (e.g., silicon) with the exception that carrier travel/capture region 106 may be shielded from incident light (e.g., by an overlying opaque material, such as a metal layer).

In some embodiments, and as discussed further below, a potential gradient may be established in the photon absorption/carrier generation region 102 and the carrier travel/capture region 106 by electrodes positioned above these regions. An example of the positioning of electrodes will be discussed with reference to FIG. 3B. However, the techniques described herein are not limited as to particular positions of electrodes used for producing an electric potential gradient. Nor are the techniques described herein limited to establishing an electric potential gradient using electrodes. In some embodiments, an electric potential gradient may be established using a spatially graded doping profile and/or a PN junction. Any suitable technique may be used for establishing an electric potential gradient that causes charge carriers to travel along the photon absorption/carrier generation region 102 and carrier travel/capture region 106.

A charge carrier segregation structure may be formed in the pixel to enable segregating charge carriers produced at different times. In some embodiments, at least a portion of the charge carrier segregation structure may be formed over the carrier travel/capture region 106. As will be described below, the charge carrier segregation structure may include one or more electrodes formed over the carrier travel/capture region 106, the voltage of which may be controlled by control circuitry to change the electric potential in the carrier travel/capture region 106.

The electric potential in the carrier travel/capture region 106 may be changed to enable capturing a charge carrier. The potential gradient may be changed by changing the voltage on one or more electrodes overlying the carrier travel/capture region 106 to produce a potential barrier that can confine a carrier within a predetermined spatial region. For example, the voltage on an electrode overlying the dashed line in the carrier travel/capture region 106 of FIG. 2A may be changed at time t5 to raise a potential barrier along the dashed line in the carrier travel/capture region 106 of FIG. 2A, thereby capturing charge carrier 101A. As shown in FIG. 2A, the carrier captured at time t5 may be transferred to a bin "bin0" of carrier storage region 108. The transfer of the carrier to the charge carrier storage bin may be performed by changing the potential in the carrier travel/capture region 106 and/or carrier storage region 108 (e.g., by changing the voltage of electrode(s) overlying these regions) to cause the carrier to travel into the charge carrier storage bin.

Changing the potential at a certain point in time within a predetermined spatial region of the carrier travel/capture region 106 may enable trapping a carrier that was generated by photon absorption that occurred within a specific time interval. By trapping photogenerated charge carriers at different times and/or locations, the times at which the charge carriers were generated by photon absorption may be discriminated. In this sense, a charge carrier may be "time binned" by trapping the charge carrier at a certain point in time and/or space after the occurrence of a trigger event. The time binning of a charge carrier within a particular bin provides information about the time at which the photogenerated charge carrier was generated by absorption of an incident photon, and thus likewise "time bins," with respect to the trigger event, the arrival of the incident photon that produced the photogenerated charge carrier.

FIG. 2B illustrates capturing a charge carrier at a different point in time and space. As shown in FIG. 2B, the voltage on an electrode overlying the dashed line in the carrier travel/capture region 106 may be changed at time t9 to raise a potential barrier along the dashed line in the carrier travel/capture region 106 of FIG. 2B, thereby capturing carrier 101B. As shown in FIG. 2B, the carrier captured at time t9 may be transferred to a bin "bin1" of carrier storage region 108. Since charge carrier 101B is trapped at time t9, it represents a photon absorption event that occurred at a different time (i.e., time t6) than the photon absorption event (i.e., at t1) for carrier 101A, which is captured at time t5.

Performing multiple measurements and aggregating charge carriers in the charge carrier storage bins of carrier storage region 108 based on the times at which the charge carriers are captured can provide information about the times at which photons are captured in the photon absorption/carrier generation area 102. Such information can be useful in a variety of applications, as discussed above.

Detailed Example of Pixel Structure and Operation

Figure 3A:
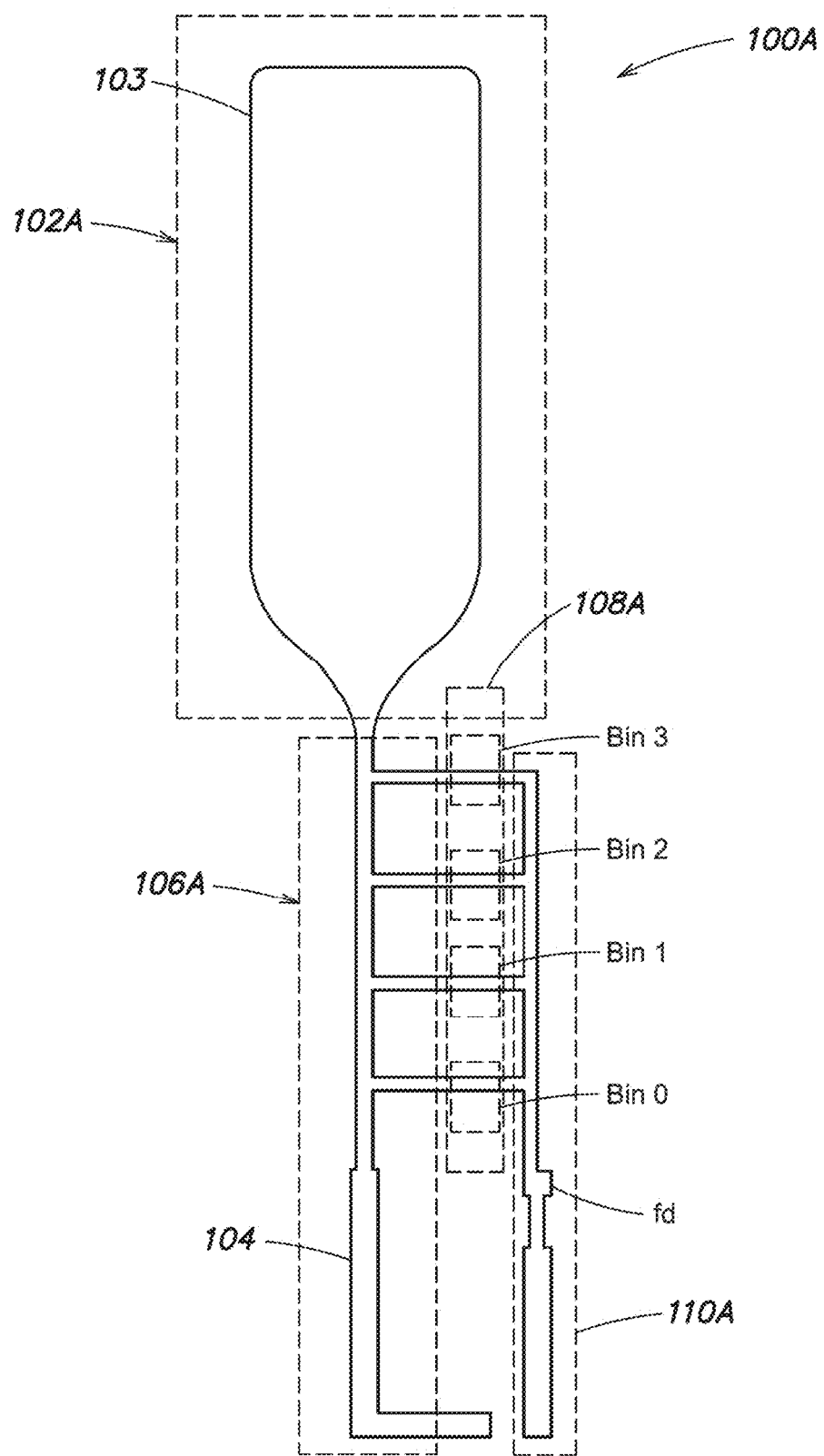
FIG. 3A shows a charge carrier confinement region of a pixel, according to some embodiments.

FIG. 3A shows a charge carrier confinement region 103 of a pixel 100A, according to some embodiments. As illustrated in FIG. 3A, pixel 100A may include a photon absorption/carrier generation area 102A (also referred to as a photodetection region), a carrier travel/capture area 106A, a drain 104, a plurality of charge carrier storage bins bin0, bin1, bin2, and bin3 of a carrier storage region 108A, and a readout region 110A.

Charge carrier confinement region 103 is a region in which photogenerated charge carriers move in response to the electric potential gradient produced by a charge carrier segregation structure. Charge carriers may be generated in photon absorption/carrier generation area 102A within charge carrier confinement region 103.

Charge carrier confinement region 103 may be formed of any suitable material, such as a semiconductor material (e.g., silicon). However, the techniques described herein are not limited in this respect, as any suitable material may form charge carrier confinement region 103. In some embodiments, charge carrier confinement region 103 may be surrounded by an insulator (e.g., silicon oxide) to confine charge carriers within charge carrier confinement region 103.

The portion of charge carrier confinement region 103 in photon absorption/carrier generation area 102A may have any suitable shape. As shown in FIG. 3A, in some embodiments the portion of charge carrier confinement region 103 in photon absorption/carrier generation area 102A may have a tapered shape, such that its width gradually decreases near carrier travel/capture area 106A. Such a shape may improve the efficiency of charge handling, which may be useful particularly in cases where few photons are expected to arrive. In some embodiments the portion of charge carrier confinement region 103 in photon absorption/carrier generation area 102A may be less tapered, or may not be tapered, which can increase the dynamic range. However, the techniques described herein are not limited as to the shape of charge carrier confinement region 103 in photon absorption/carrier generation area 102A.

As shown in FIG. 3A, a first portion of charge carrier confinement region 103 in carrier travel/capture area 106A may extend from the photon absorption/carrier generation area 102A to a drain 104. Extensions of the charge carrier confinement region 103 extend to the respective charge storage bins, allowing charge carriers to be directed into the charge carrier storage bins by a charge carrier segregation structure such as that described with respect to FIG. 3B. In some embodiments, the number of extensions of the charge carrier confinement region 103 that are present may be the same as the number of charge carrier storage bins, with each extension extending to a respective charge carrier storage bin.

Readout region 110A may include a floating diffusion node fd for read out of the charge storage bins. Floating diffusion node fd may be formed by a diffusion of n-type dopants into a p-type material (e.g., a p-type substrate), for example. However, the techniques described herein are not limited as to particular dopant types or doping techniques.

Figure 3B:
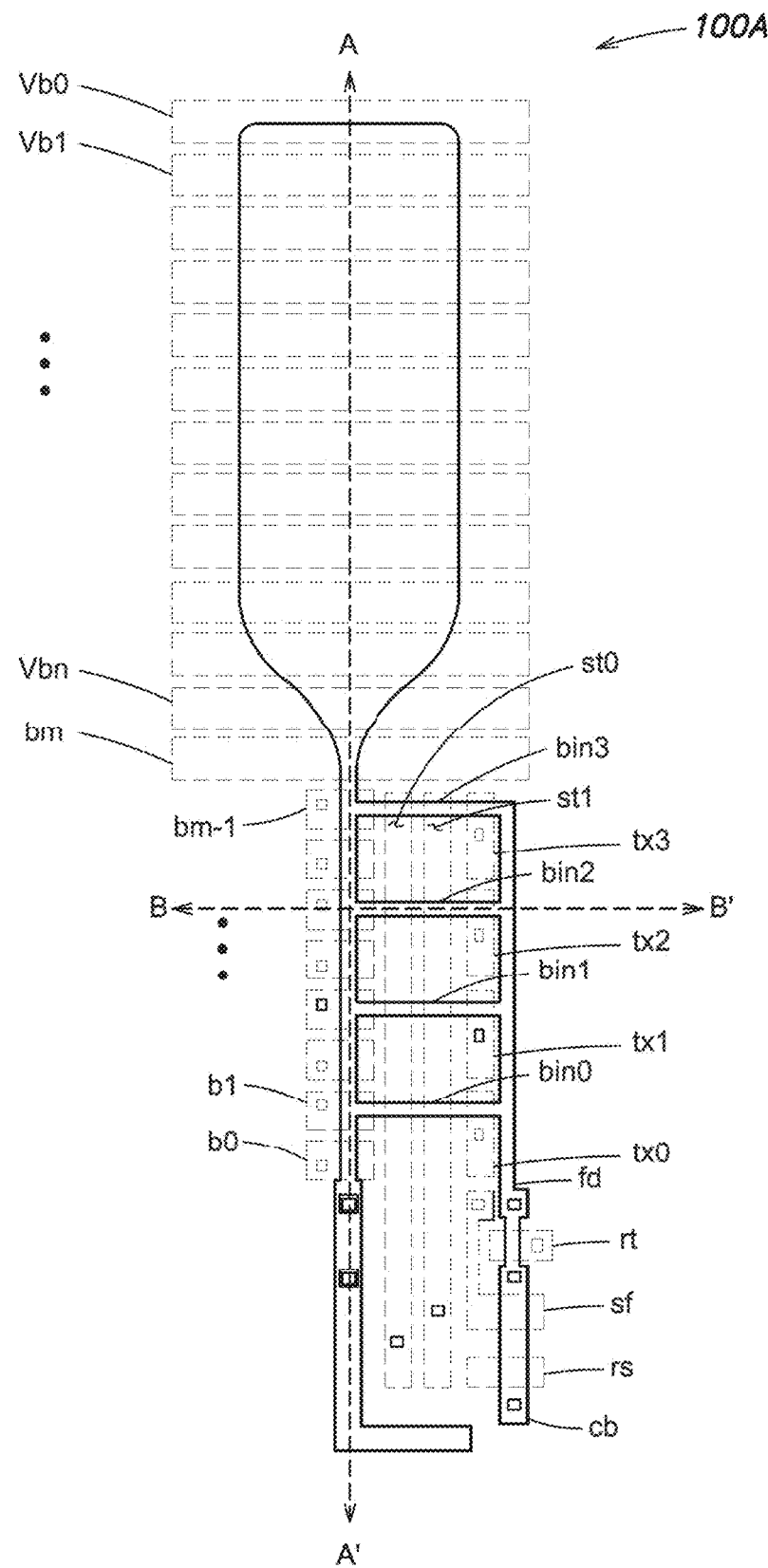
FIG. 3B shows the pixel of FIG. 3A with a plurality of electrodes Vb0-Vbn, b0-bm, st1, st2, and tx0-tx3 overlying the charge carrier confinement region of FIG. 3A.

FIG. 3B shows the pixel 100A of FIG. 3A with a plurality of electrodes Vb0-Vbn, b0-bm, st1, st2, and tx0-tx3 overlying the charge carrier confinement region 103 of FIG. 3A. The electrodes shown in FIG. 3B form at least a portion of a charge carrier segregation structure that can time-bin photogenerated carriers.

The electrodes shown in FIG. 3B establish an electric potential within the charge carrier confinement region 103. In some embodiments, the electrodes Vb0-Vbn, b0-bm may have a voltage applied thereto to establish a potential gradient within regions 102A and 106A such that charge carriers, e.g., electrons, travel in the downward direction of FIG. 3B toward the drain 104. Electrodes Vb0-Vbn may establish a potential gradient in the charge confinement region 103 of photon absorption/carrier generation area 102A. In some embodiments, respective electrodes Vb0-Vbn may be at constant voltages. Electrodes b0-bm may establish a potential gradient in the charge confinement region 103 of carrier travel/capture area 106A. In some embodiments, electrodes b0-bm may have their voltages set to different levels to enable trapping charge carriers and/or transferring charge carriers to one or more charge storage bins.

Electrodes st0 and st1 may have voltages that change to transfer carriers to the charge storage bins of charge carrier storage region 108A. Transfer gates tx0, tx1, tx2 and tx3 enable transfer of charge from the charge storage bins to the floating diffusion node fd. Readout circuitry 110 including reset transistor rt, amplification transistor sf and selection transistor rs is also shown.

In some embodiments, the potentials of floating diffusion node fd and each of the transfer gates tx0-tx3 may allow for overflow of charge carriers into the floating diffusion rather than into the carrier travel/capture area 106A. When charge carriers are transferred into a bin within the carrier storage region 108, the potentials of the floating diffusion node fd and the transfer gates tx0-tx3 may be sufficiently high to allow any overflow charge carriers in the bin to flow to the floating diffusion. Such a "barrier overflow protection" technique may reduce carriers overflowing and diffusing into the carrier travel/capture area 106A and/or other areas of the pixel. In some embodiments, a barrier overflow protection technique may be used to remove any overflow charge carriers generated by an excitation pulse. By allowing overflow charge carriers to flow to the floating diffusion, these charge carriers are not captured in one or more time bins, thereby reducing the impact of the excitation pulse on the time bin signals during readout.

In some embodiments in which electrodes Vb0-Vbn and b0-bm are disposed over the photon absorption/carrier generation region 102 and/or the carrier travel/capture region 106, the electrodes Vb0-Vbn and b0-bm may be set to voltages that increase for positions progressing from the top to the bottom of FIG. 3B, thereby establishing the potential gradient that causes charge carriers to travel in the downward direction of FIG. 3B toward the drain 104. In some embodiments, the potential gradient may vary monotonically in the photon absorption/carrier generation region 102 and/or the carrier travel/capture region 106, which may enable charge carriers to travel along the potential gradient into the carrier travel/capture region 106. In some embodiments, the potential gradient may change linearly with respect to position along the line A-A'. A linear potential gradient may be established by setting electrodes to voltages that vary linearly across the vertical dimension of FIG. 3B. However, the techniques described herein are not limited to a linear potential gradient, as any suitable potential gradient may be used. In some embodiments, the electric field in the carrier travel/capture region 106 may be high enough so charge carriers move fast enough in the carrier travel/capture region 106 such that the transit time is small compared to the time over which photons may arrive. For example, in the fluorescence lifetime measurement context, the transit time of charge carriers may be made small compared to the lifetime of a luminescent marker being measured. The transit time can be decreased by producing a sufficiently graded electric field in the carrier travel/capture region 106.

Figure 3C:
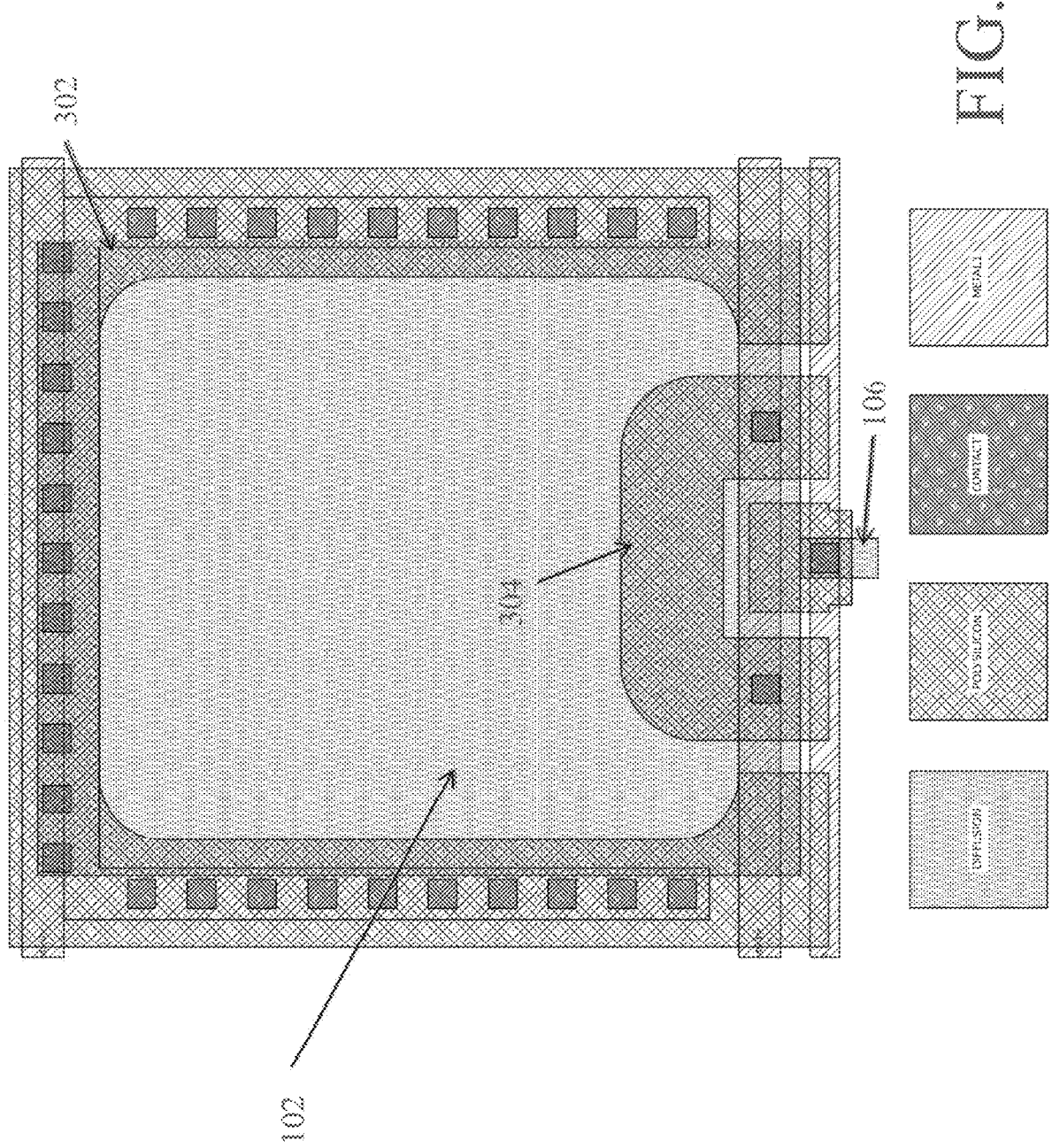
FIG. 3C shows an embodiment in which the photon absorption/carrier generation region includes a PN junction.

FIG. 3C shows an embodiment in which the photon absorption/carrier generation region 102 includes a PN junction. FIG. 3C shows an outer electrode 302, which may be at a relatively low potential, thereby "pinning" the surface potential at a relatively low potential. An electrode 304 may be included to assist in producing the potential gradient for a static electric field that drives carriers toward carrier travel/capture area 106 (the lower portion of carrier travel/ capture area 106 is not shown). FIG. 3C indicates regions of diffusion, polysilicon, contact and metal 1.

Figure 3D:
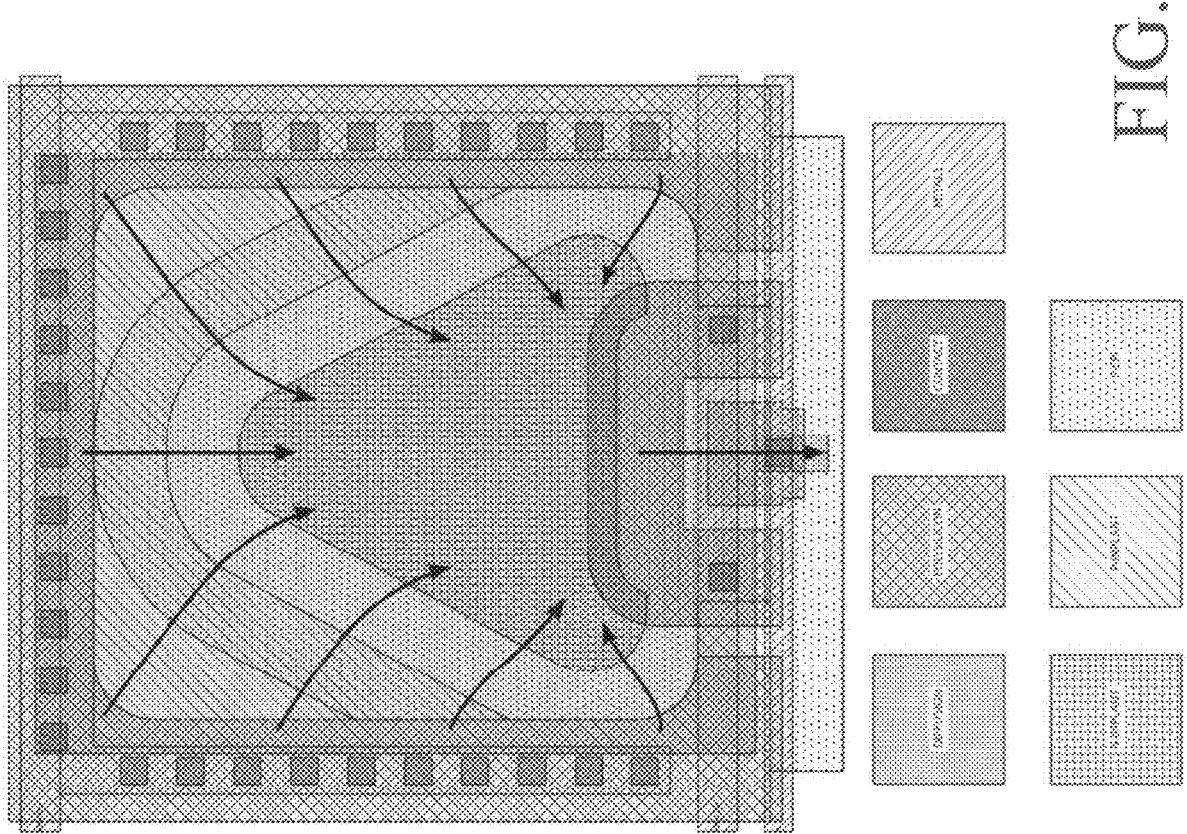
FIG. 3D shows a top view of a pixel as in FIG. 3C, with the addition of doping characteristics.

FIG. 3D shows a top view of a pixel as in FIG. 3C, with the addition of doping characteristics. FIG. 3D also shows the electric field sweeping carriers down to region 106 along the potential gradient established by the PN junction and the electrode 304. FIG. 3D indicates regions of diffusion, polysilicon, contact, metal 1, N-implant, P-implant, and P-epi.

Figure 3E:
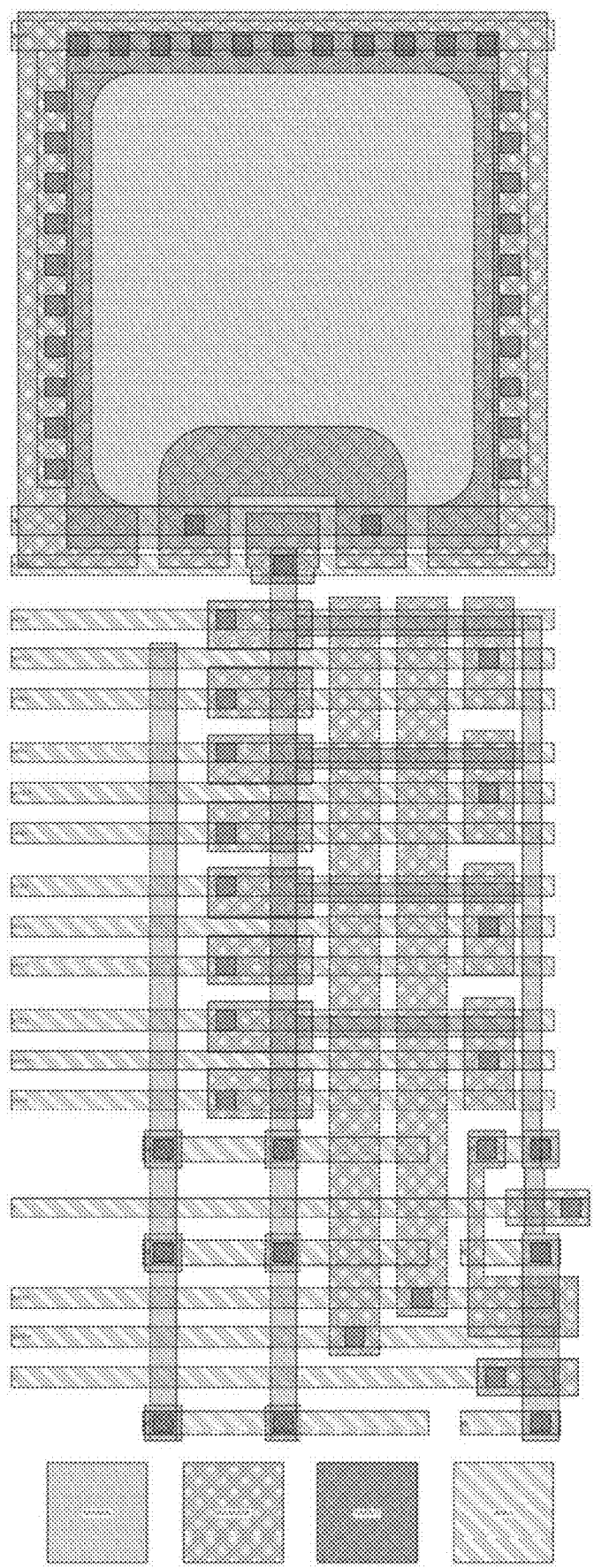
FIG. 3E shows a top view of a pixel as in FIG. 3C, including the carrier travel/capture area.

FIG. 3E shows a top view of a pixel as in FIG. 3C, including the carrier travel/capture area 106.

Figure 3F:
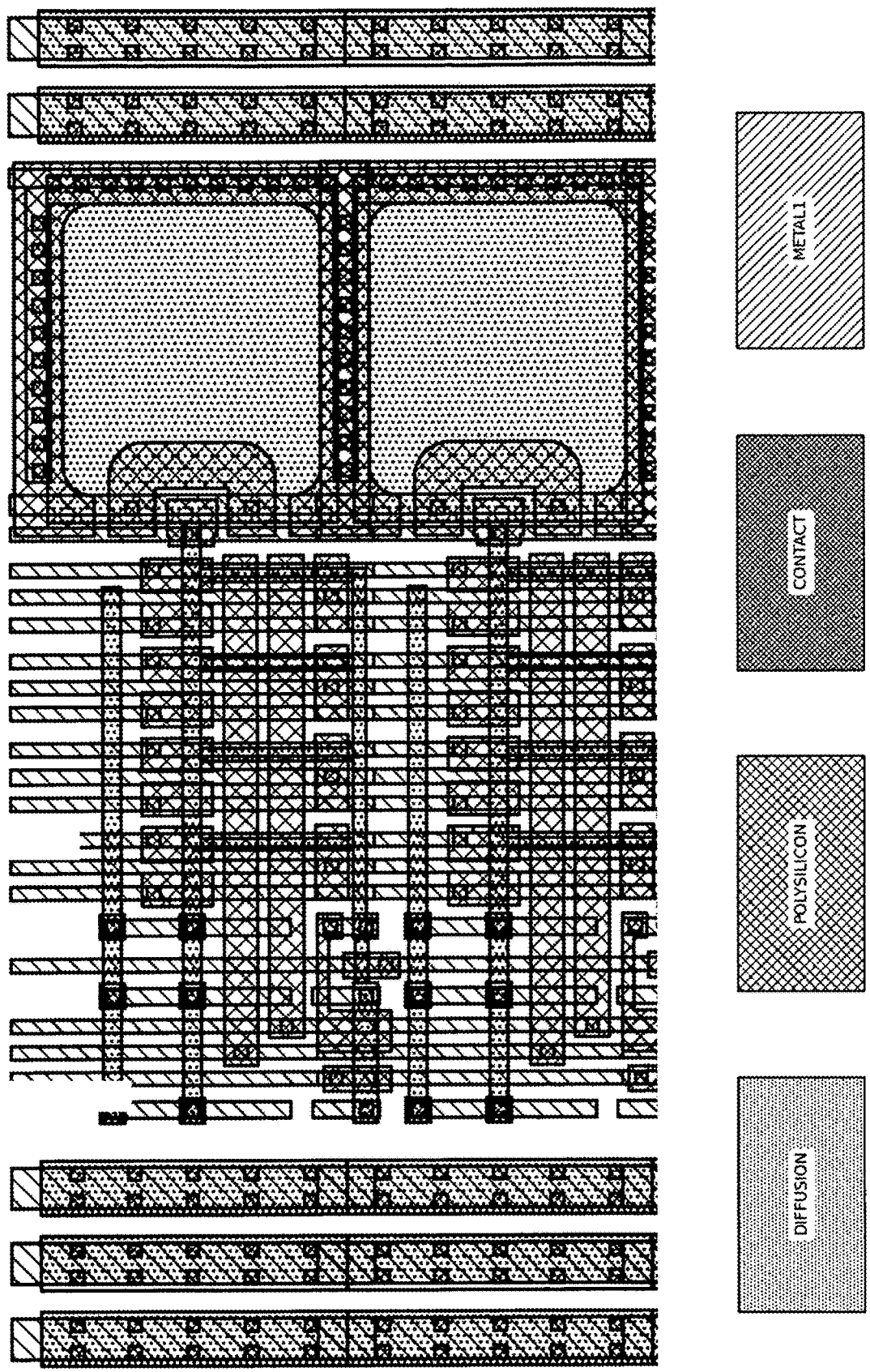
FIG. 3F shows an array of pixels as in FIG. 3E.

FIG. 3F shows an array of pixels as in FIG. 3E. FIG. 3F indicates regions of diffusion, polysilicon, contact and metal 1.

FIG. 3G shows the pixel array of FIG. 3F and also indicates regions of diffusion, polysilicon, contact, metal 1, N-implant, P-implant, and P-epi.

Figure 4:
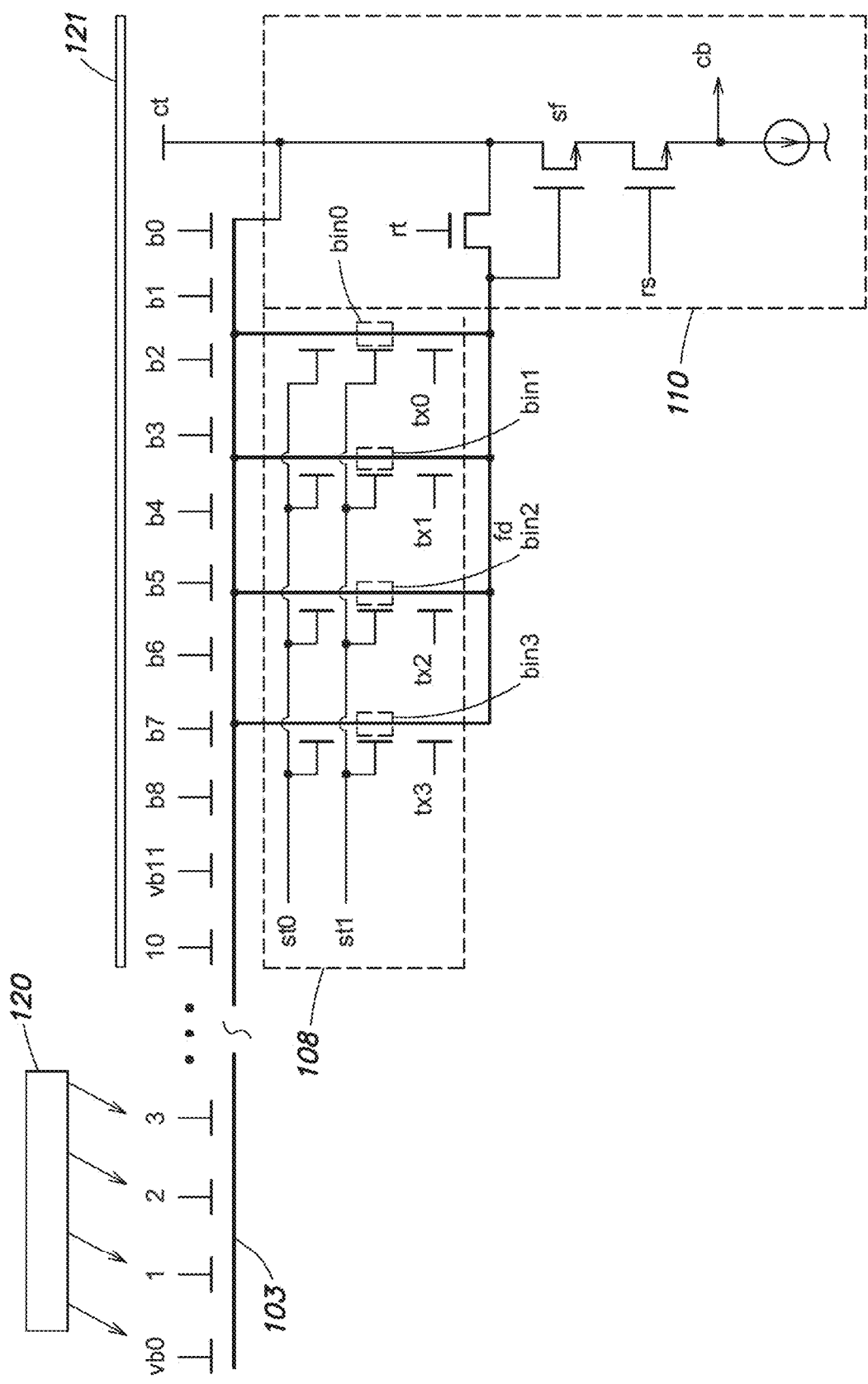
FIG. 4 shows a circuit diagram of the pixel of FIG. 3B. The charge carrier confinement area is shown in heavy dark lines.

FIG. 4 shows a circuit diagram of the pixel 100A of FIG. 3B. The charge carrier confinement area 103 is shown in heavy dark lines. Also shown are the electrodes, charge carrier storage area 108 and readout circuitry 110. In this embodiment, the charge storage bins bin0, bin1, bin2, and bin3 of carrier storage region 108 are within the carrier confinement area 103 under electrode st1. As discussed above, in some embodiments a junction may be used to produce a static field in region 102 instead of or in addition to the electrodes.

Light is received from a light source 120 at photon absorption/carrier generation area 102. Light source 120 may be any type of light source, including a luminescent sample (e.g., linked to a nucleic acid) or a region or scene to be imaged, by way of example and not limitation. A light shield 121 prevents light from reaching carrier travel/capture area 106. Light shield 121 may be formed of any suitable material, such a metal layer of the integrated circuit, by way of example and not limitation.

Figure 5A:
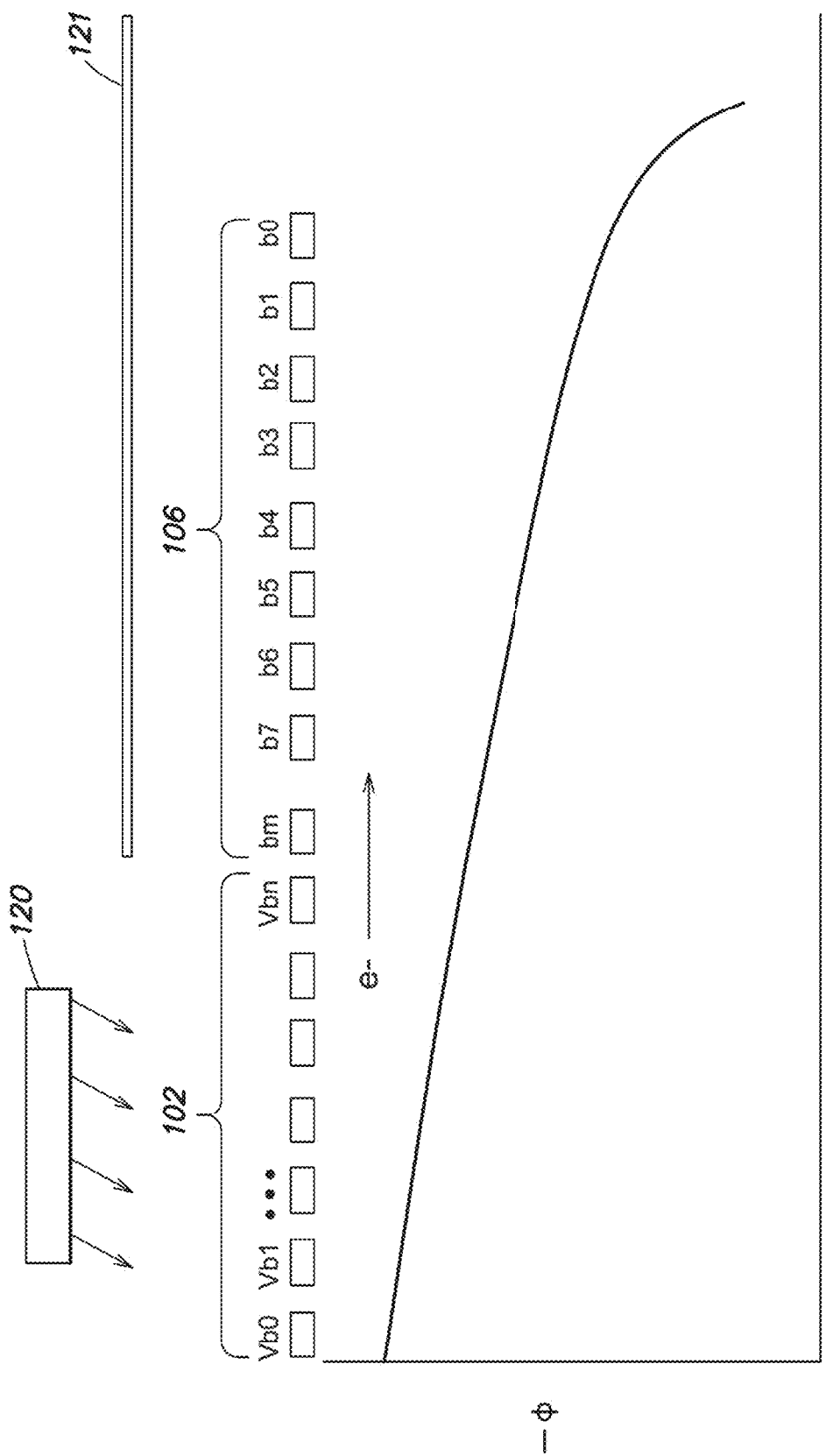
FIG. 5A illustrates a potential gradient that may be established in the charge carrier confinement area in the photon absorption/carrier generation area and the carrier travel/capture area along the line A-A' of FIG. 3B.

FIG. 5A illustrates a potential gradient that may be established in the charge carrier confinement area 103 in photon absorption/carrier generation area 102 and carrier travel/capture area 106 along the line A-A' of FIG. 3B. As illustrated in FIG. 5A, a charge carrier (e.g., an electron) may be generated by absorption of a photon within the photon absorption/carrier generation area 102. Electrodes Vb0-Vbn and b0-bm are set to voltages that increase to the right of FIG. 5A to establish the potential gradient the causes electrons to flow to the right in FIG. 5A (the downward direction of FIG. 3B). Additionally or alternatively, a PN junction may be present to establish or assist in establishing the field. In such an embodiment, carriers may flow below the surface, and FIG. 5A (and related figures) shows the potential in the region where the carriers flow. Initially, carriers may be allowed to flow through the carrier travel/capture area 106 into the drain 104, as shown in FIGS. 6A, 6B and 6C. FIG. 6A shows the position of a carrier 101 once it is photogenerated. FIG. 6B shows the position of a carrier 101 shortly thereafter, as it travels in the downward direction in response to the established potential gradient. FIG. 6C shows the position of the carrier 101 as it reaches the drain 104.

Figure 5B:
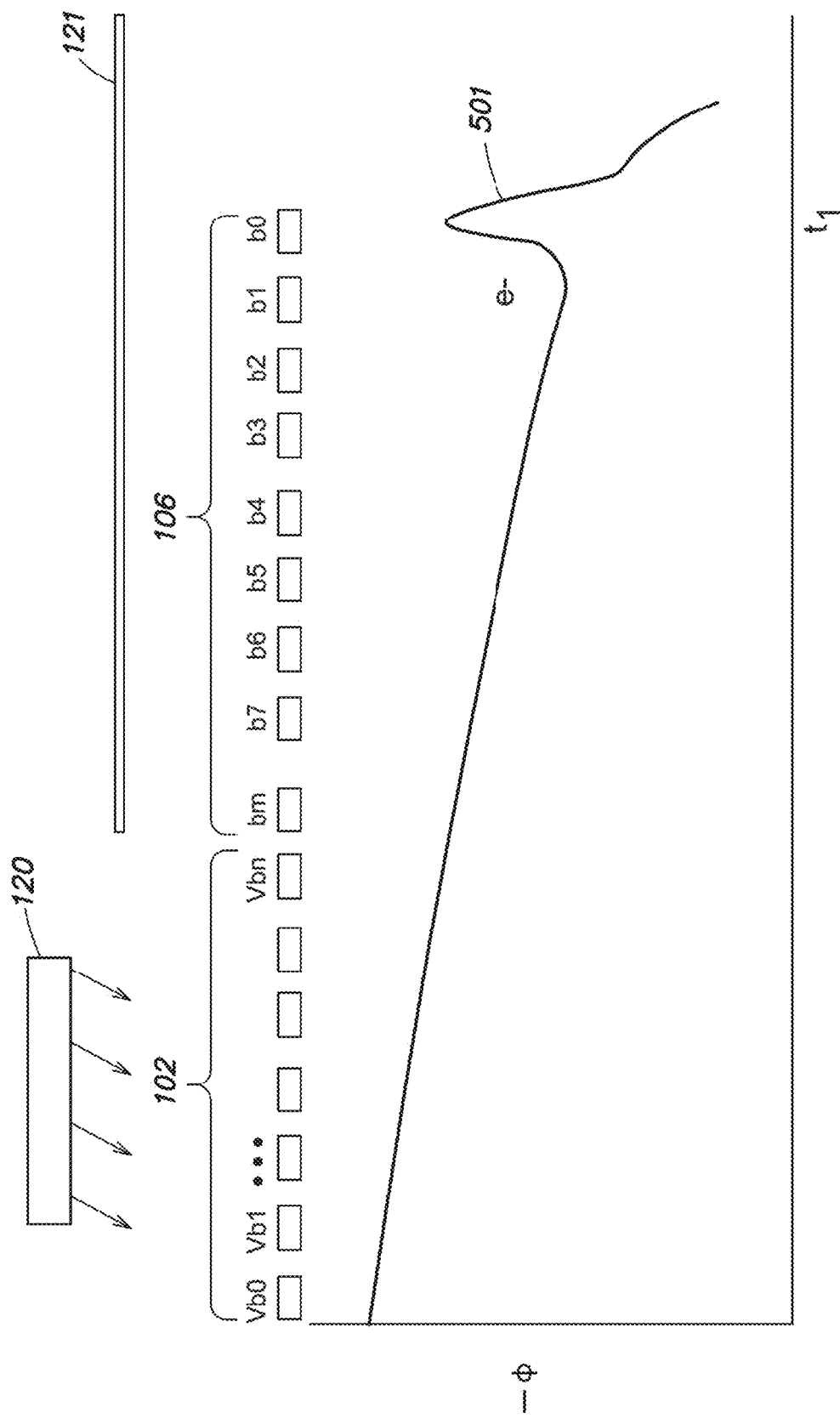
FIG. 5B shows that after a period of time a potential barrier to electrons may be raised at a time t1 by decreasing the voltage of electrode b0.

FIG. 5B shows that after a period of time a potential barrier 501 to electrons may be raised at a time t1 by decreasing the voltage of electrode b0. The potential barrier 501 may stop an electron from traveling to the right in FIG. 5B, as shown in FIGS. 6D, 6E and 6F. FIG. 6D shows the position of a carrier 101 (e.g., an electron) once it is photogenerated. FIG. 6E shows the position of a carrier 101 shortly thereafter, as it travels in the downward direction in response to the potential gradient. FIG. 6F shows the position of the carrier 101 as it reaches the potential barrier 501 after time t1.

Figure 5C:
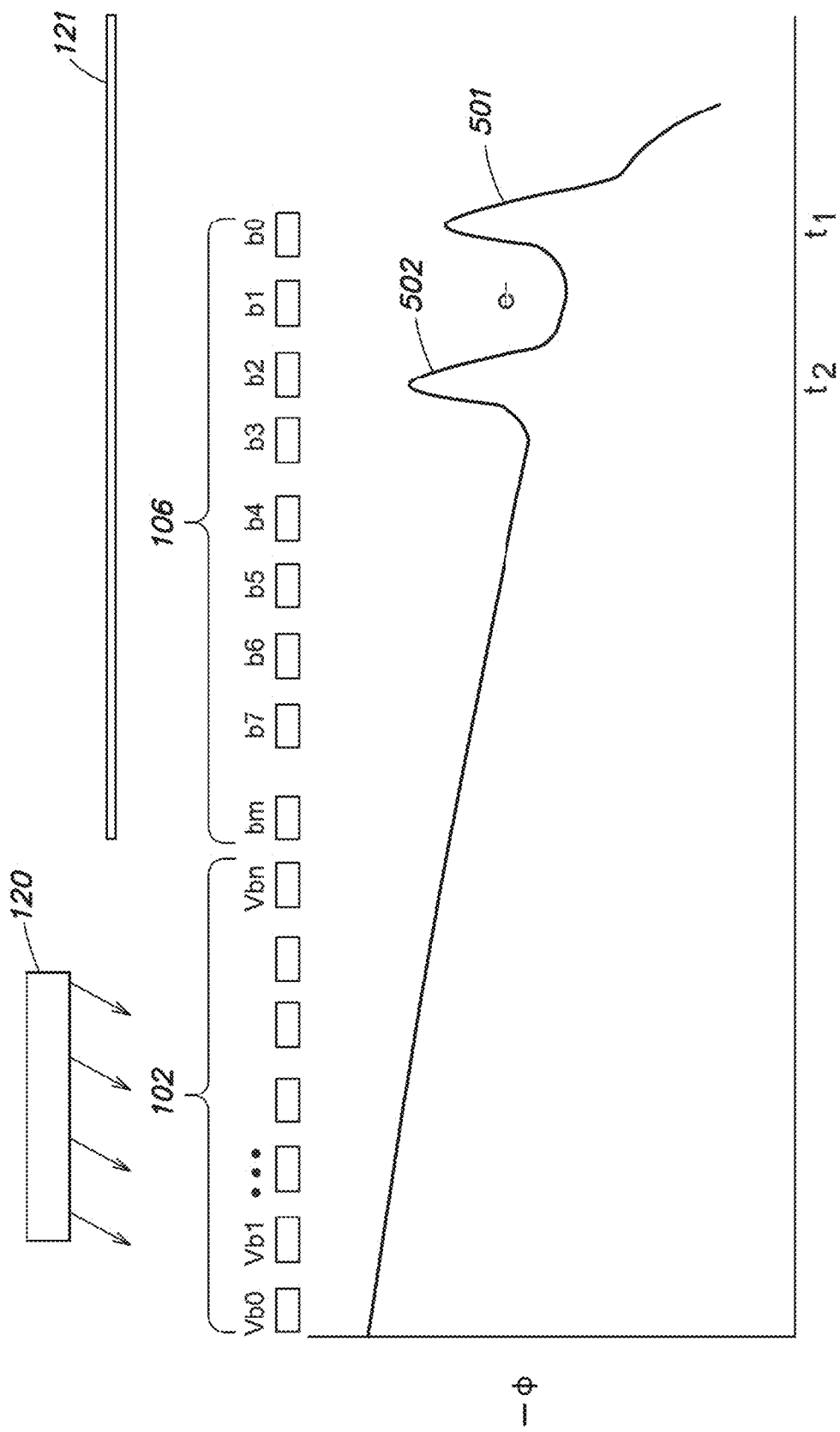
FIG. 5C shows that after another time period, another potential barrier to electrons may be raised at time t2 by decreasing the voltage of electrode b2.
Figure 6G:
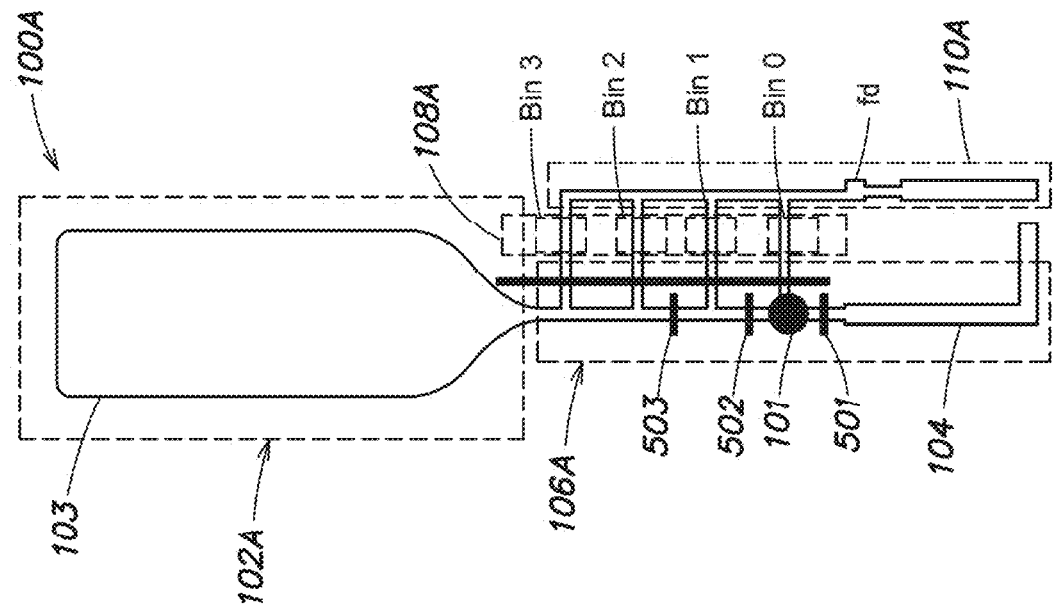
FIG. 6G shows that if an electron arrives between electrodes b0 and b2 between times t1 and t2, the electron will be captured between potential barrier 501 and potential barrier 502, as illustrated in FIG. 6G.

FIG. 5C shows that after another time period, another potential barrier 502 to electrons may be raised at time t2 by decreasing the voltage of electrode b2. If an electron arrives between electrodes b0 and b2 between times t1 and t2, the electron will be captured between potential barrier 501 and potential barrier 502, as illustrated in FIG. 5C and FIG. 6G.

Figure 5D:
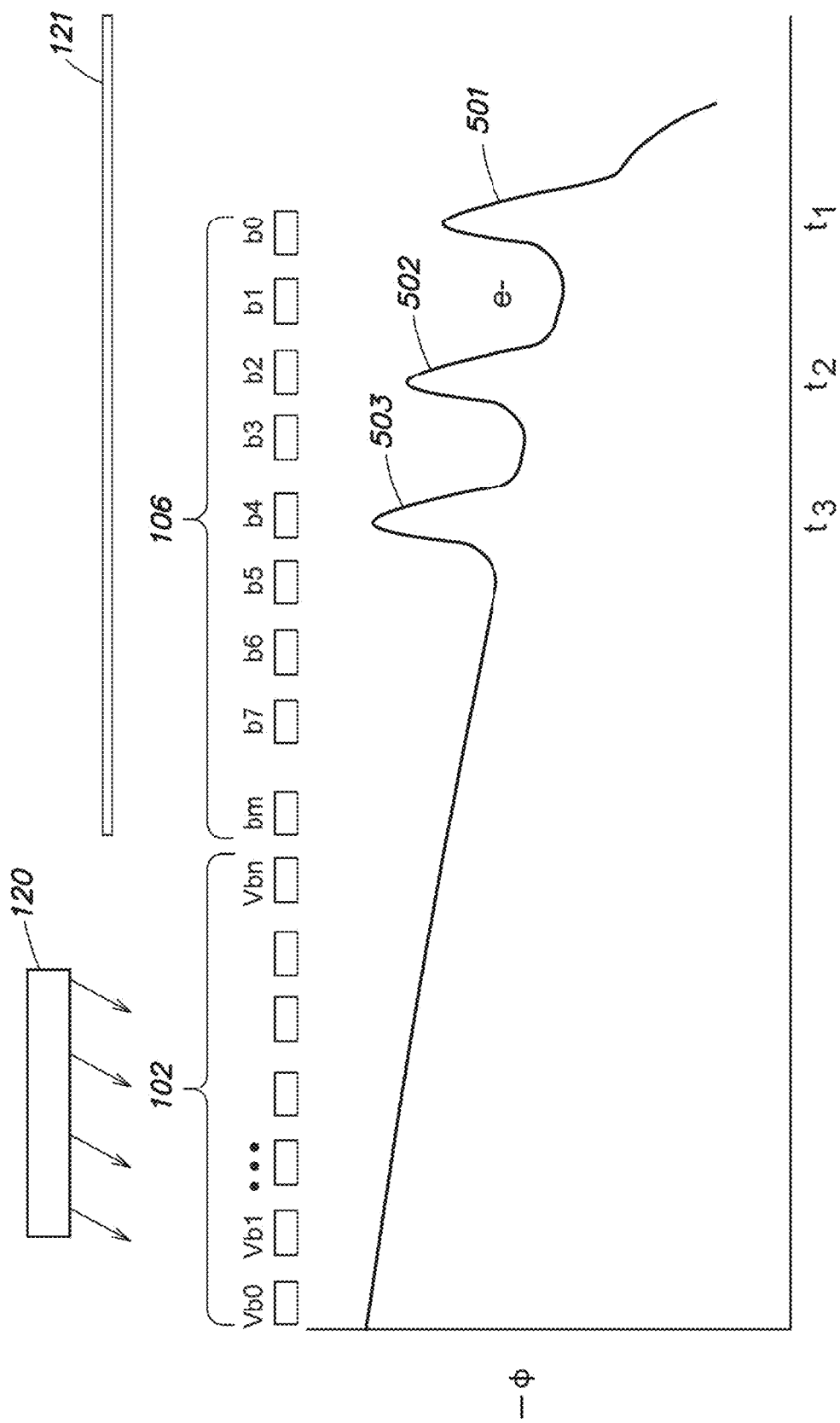
FIG. 5D shows that after another time period, another potential barrier to electrons may be raised at time t3 by decreasing the voltage of electrode b4.
Figure 6H:
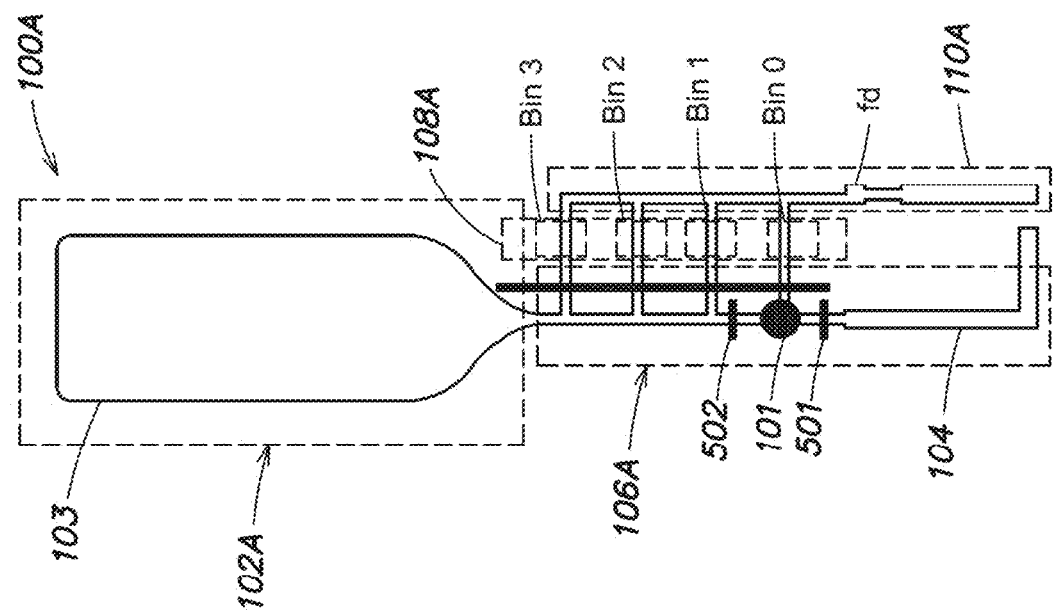
FIG. 6H shows an example in which an electron arrived between times t1 and t2, so it remains captured between potential barrier 501 and potential barrier 502.

FIG. 5D shows that after another time period, another potential barrier 503 to electrons may be raised at time t3 by decreasing the voltage of electrode b4. If an electron arrives between electrodes b2 and b4 between times t2 and t3, the electron will be trapped in a location between potential barrier 502 and potential barrier 503. In the example of FIGS. 5D and 6H, an electron arrived between times t1 and t2, so it remains captured between potential barrier 501 and potential barrier 502.

Figure 5E:
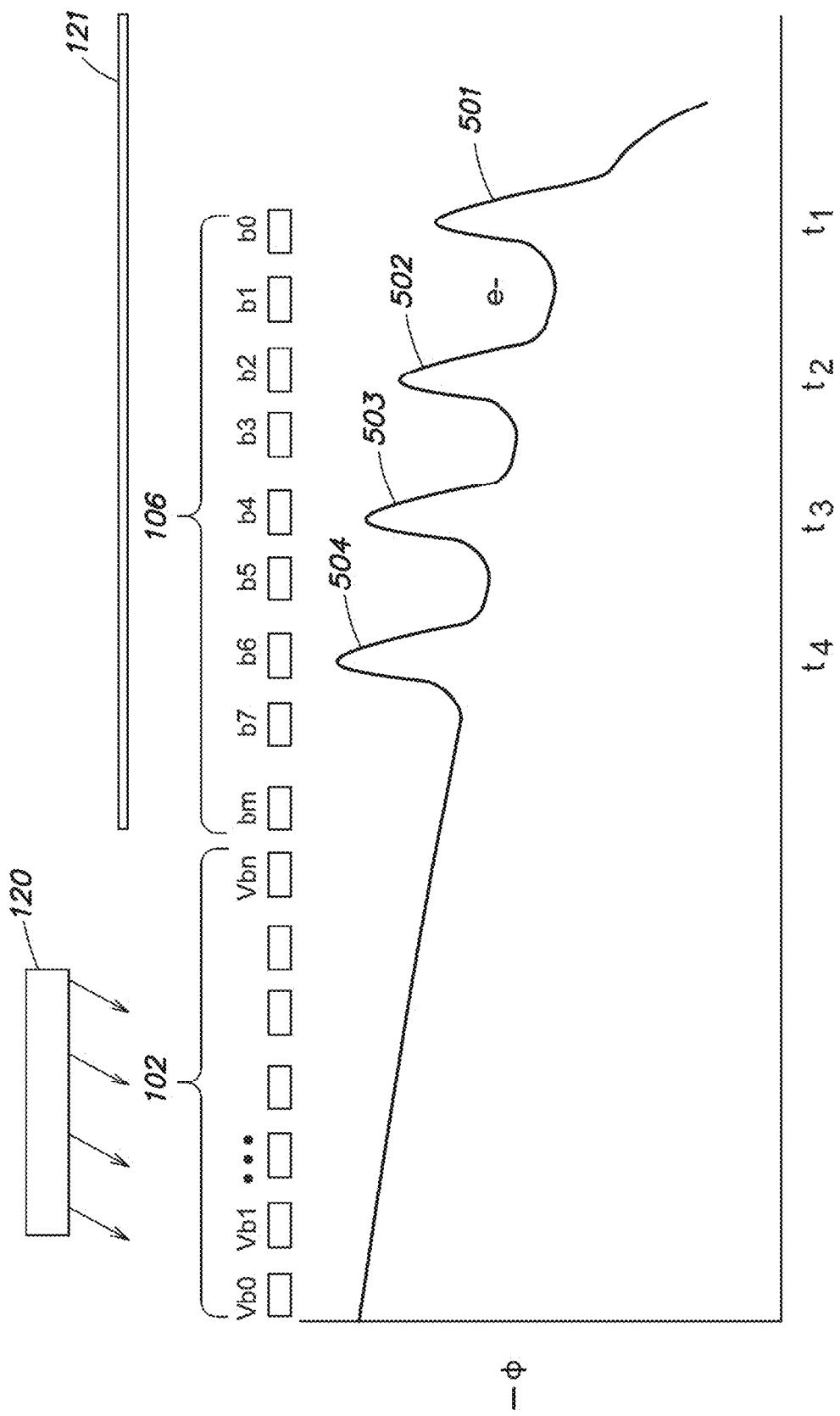
FIG. 5E shows that after another time period, another potential barrier to electrons may be raised at time t4 by decreasing the voltage of electrode b6.

FIG. 5E shows that after another time period, another potential barrier 504 to electrons may be raised at time t4 by decreasing the voltage of electrode b6. If an electron arrives between electrodes b4 and b6 between times t3 and t4, the electron will be trapped in a location between potential barrier 503 and potential barrier 504. In the example of FIGS. 5E and 6I, an electron arrived between times t1 and t2, so it remains captured between potential barrier 501 and potential barrier 502.

Figure 5F:
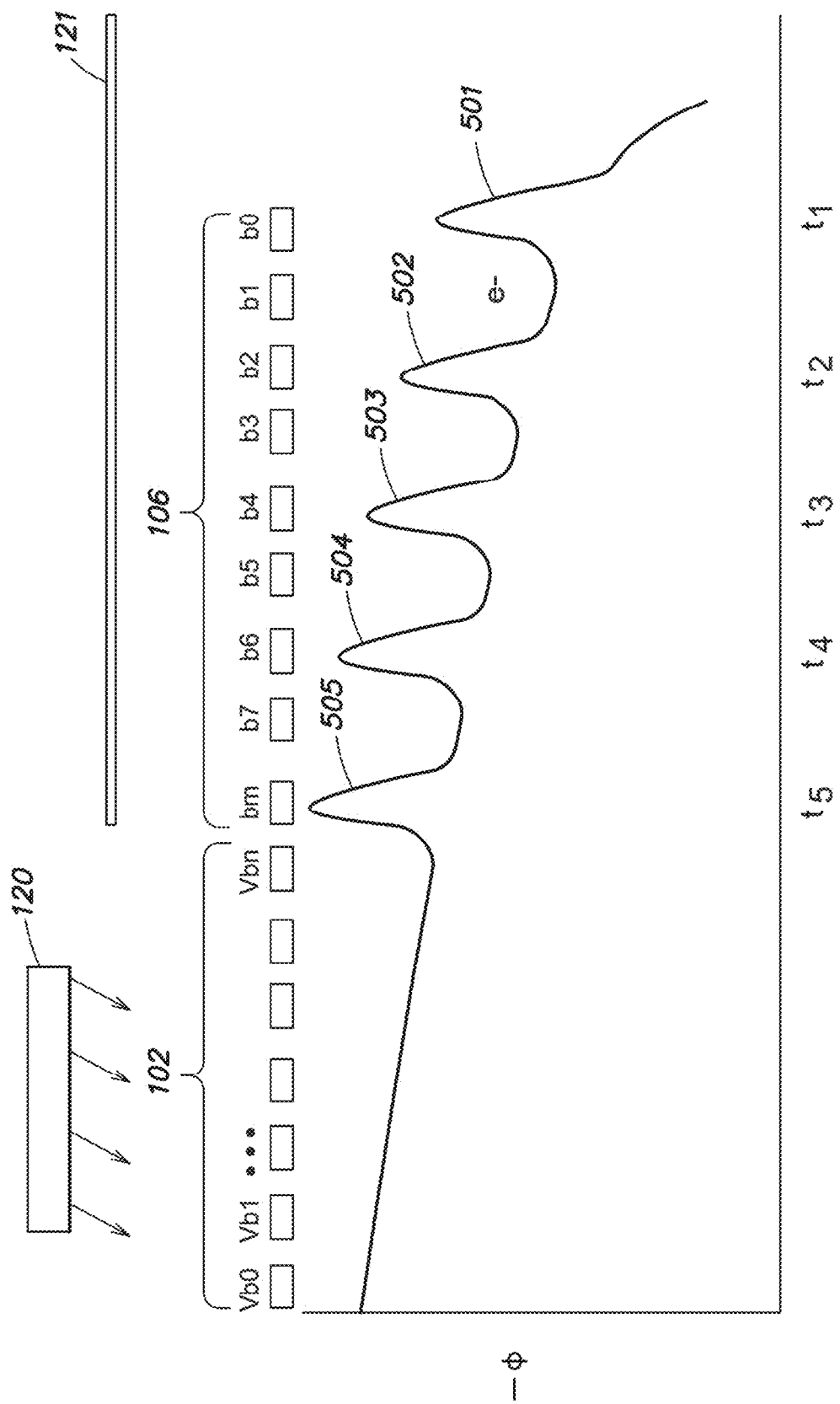
FIG. 5F shows that after another time period, another potential barrier to electrons may be raised at time t5 by decreasing the voltage of electrode bm.

FIG. 5F shows that after another time period, another potential barrier 505 to electrons may be raised at time t5 by decreasing the voltage of electrode bm. If an electron arrives between electrodes b6 and bm between times t4 and t5, the electron will be trapped in a location between potential barrier 504 and potential barrier 505. In the example of FIGS. 5F and 6J, an electron arrived between times t1 and t2, so it remains captured between potential barrier 501 and potential barrier 502.

Figure 6K:
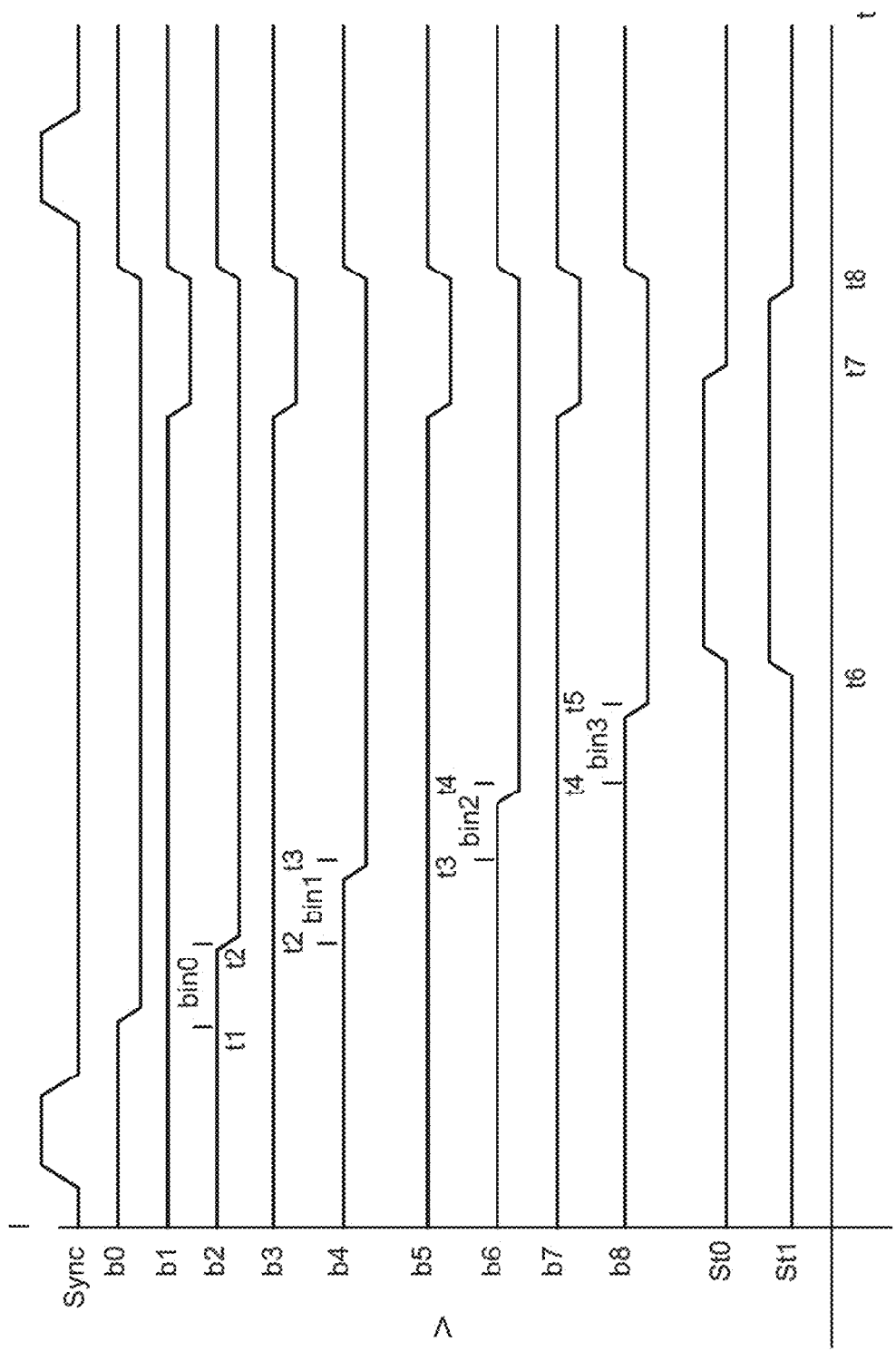
FIG. 6K shows a voltage timing diagram illustrating the voltages of electrodes b0-b8, st0 and st1 over time.

FIG. 6K shows a voltage timing diagram illustrating the voltages of electrodes b0-b8, st0 and st1 over time. A charge carrier moving through the carrier travel/capture area 106 during the sequence of raising potential barriers 501-505 will be captured at a location within the carrier travel/capture area 106 that depends on the time at which it arrives at the carrier travel/capture area 106, which in turn depends upon the time at which the charge carrier was generated by photon absorption in photon absorption/carrier generation area 102. The timing with which potential barriers 501-505 are raised sets the timing of the charge storage bins bin0-bin3. As shown in FIG. 6K, a carrier that arrives between times t1 and t2 will be trapped within a time interval for bin0, a carrier that arrives between times t2 and t3 will be trapped within a time interval for bin1, a carrier that arrives between times t3 and t4 will be trapped within a time interval for bin2, and a carrier that arrives between times t4 and t5 will be trapped within a time interval for bin3.

After the sequence shown in FIG. 5A-5F, a captured charge carrier may then be transferred to the appropriate charge carrier storage bin based on the location at which the charge carrier is captured within the carrier travel/capture area 106. In this embodiment, if an electron is captured under electrode b1, it is transferred to bin0. If an electron is captured under electrode b3, it is transferred to bin1. If an electron is captured under electrode b5, it is transferred to bin2. If an electron is captured under electrode b7, it is transferred to bin3. In some embodiments, transfer of any captured carrier(s) within the carrier travel/capture area 106 to their corresponding bin(s) may be performed in parallel (e.g., simultaneously). However, the techniques described herein are not limited as to transferring captured carriers to charge storage bins in parallel.

As shown in FIG. 6K, after the sequence shown in FIG. 5A-5F the voltages on electrodes st0 and st1 may be changed to transfer any captured charge carriers to the corresponding charge carrier storage bin(s). An example sequence for transferring captured charge carrier(s) will be discussed with respect to FIG. 6K and FIGS. 7A-7G.

Figure 7A:
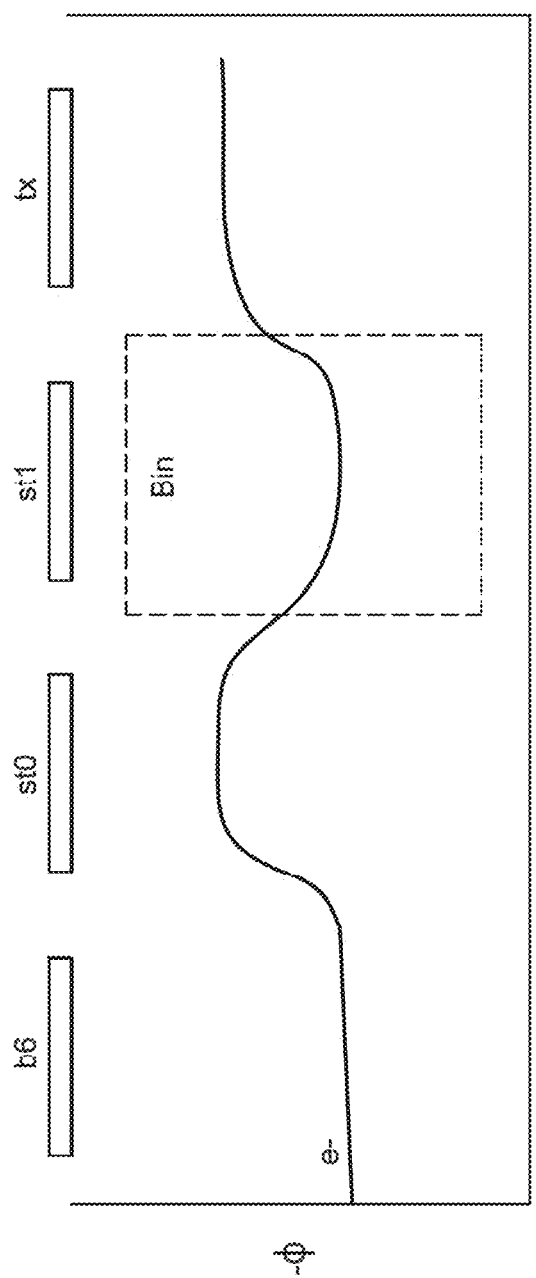
FIG. 7A shows a plot of the of potential for a cross section of the charge carrier confinement area along the line B-B' of FIG. 3B.

FIG. 7A shows a plot of the of potential for a cross section of the charge carrier confinement area 103 along the line B-B' of FIG. 3B. FIG. 7A shows the potential at time t5 (FIG. 6K) in an example where an electron is captured between potential barriers 503 and 504. A plan view showing an electron captured between potential barriers 503 and 504 is shown in FIG. 7E.

Figure 7B:
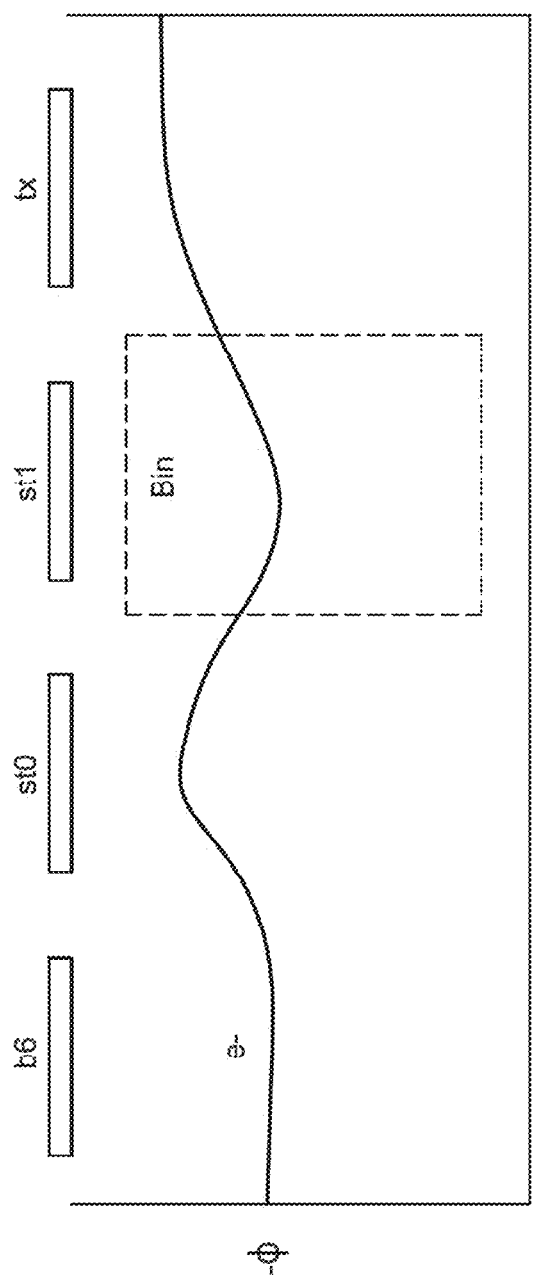
FIG. 7B shows that after time t5 the voltage on electrodes b1, b3, b5 and b7 optionally may be decreased (not shown in FIG. 6K) to raise the position of an electron within the potential well, to facilitate transferring the electron.

FIG. 7B shows that after time t5 the voltage on electrodes b1, b3, b5 and b7 optionally may be decreased (not shown in FIG. 6K) to raise the position of an electron within the potential well, to facilitate transferring the electron.

Figure 7C:
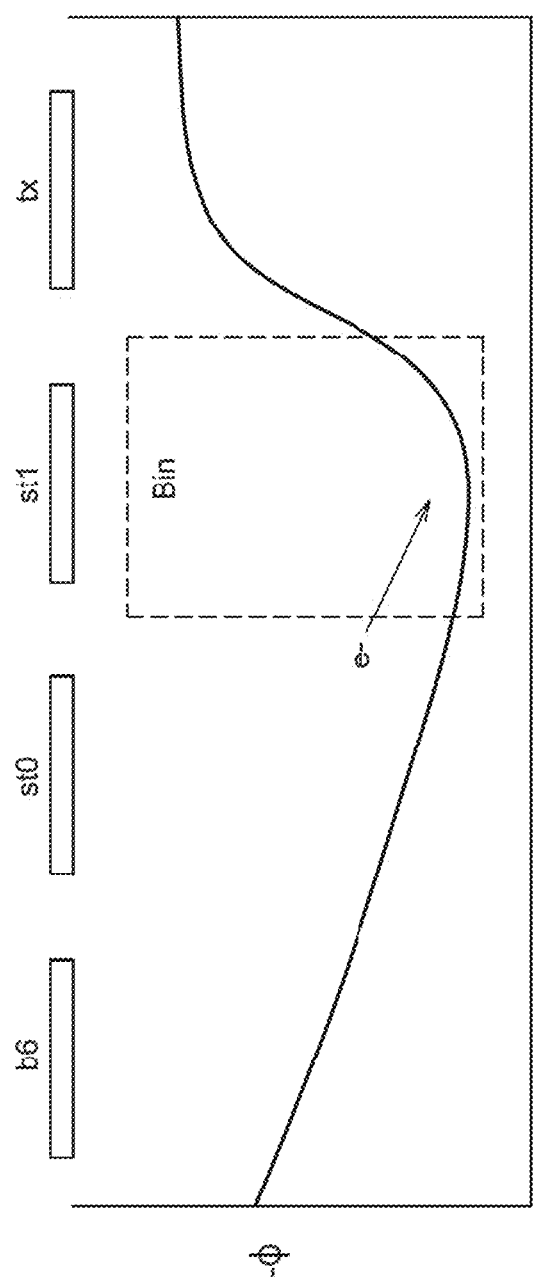
FIG. 7C shows that at time t6 (FIG. 6K), the voltages on electrodes st0 and st1 may be raised.

FIG. 7C shows that at time t6 (FIG. 6K), the voltages on electrodes st0 and st1 may be raised. Changing the voltages of the electrodes in this manner may provide a potential gradient that causes a transfer a charge carrier captured in carrier travel/capture area 106 to a corresponding charge storage bin under electrode st1. A plan view showing the voltage of electrode st1 being raised and the carrier 101 being transferred is shown in FIG. 7F.

Figure 7D:
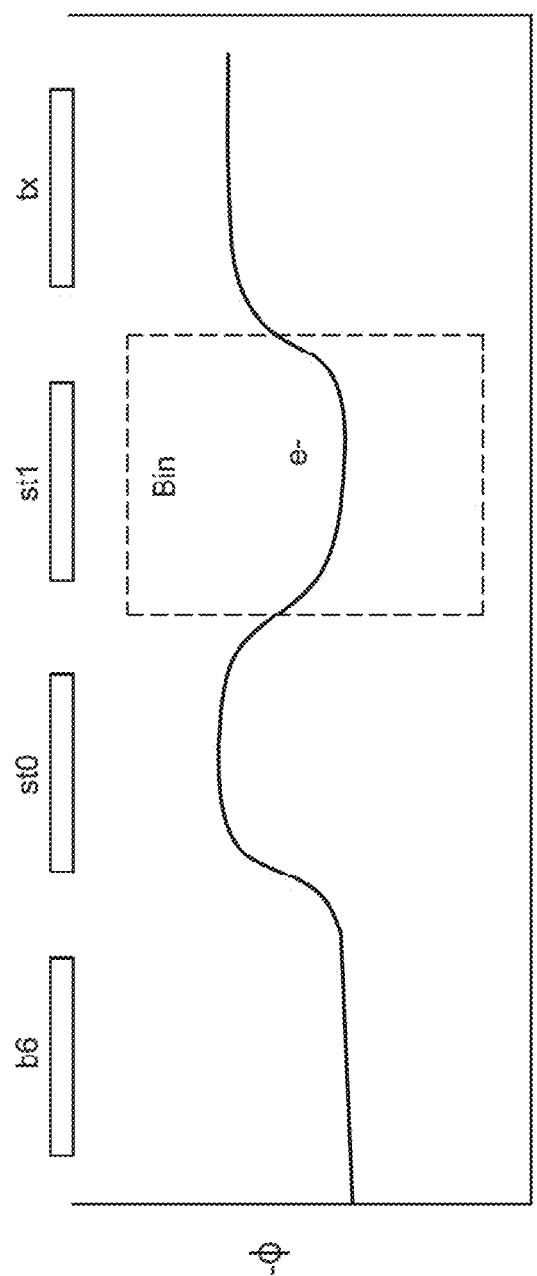
FIG. 7D shows that at time t7, the voltage on electrode st0 may be dropped, thereby confining the captured carrier (if any) in the corresponding bin (bin2 in this example).

FIG. 7D shows that at time t7, the voltage on electrode st0 may be dropped, thereby confining the captured carrier (if any) in the corresponding bin (bin2 in this example). The voltage on electrode b6 may be raised at time t8 to reestablish the potential gradient in the carrier travel/capture area 106. A plan view showing the voltage electrode st1 being lowered and the carrier 101 being captured in bin2 is shown in FIG. 7G.

FIG. 7H shows the characteristics of the electrodes of a charge carrier segregation structure, according to some embodiments. FIG. 7H specifies, for each electrode, the voltage during the gradient phase, the voltage during the binning phase, the voltage during the transfer phase, the voltage during the readout phase the high, and type of voltage change. However, this is merely an example, and the techniques described herein are not limited as to the implementation details illustrated in FIG. 7H.

Example Sequence of Measurements

Repeating the process of photon absorption/carrier generation and time binning of photogenerated charge carriers may enable gathering statistical information about the times at which photons arrive at the photodetector, as discussed below.

In some embodiments, a "measurement" may include receiving a photon, capturing a charge carrier at a particular time and/or location and transferring the captured carrier to a charge storage node corresponding to a particular time period or bin. A measurement may be repeated a plurality of times to gather statistical information about the times at which photons arrive at the photodetector.

Figure 8A:
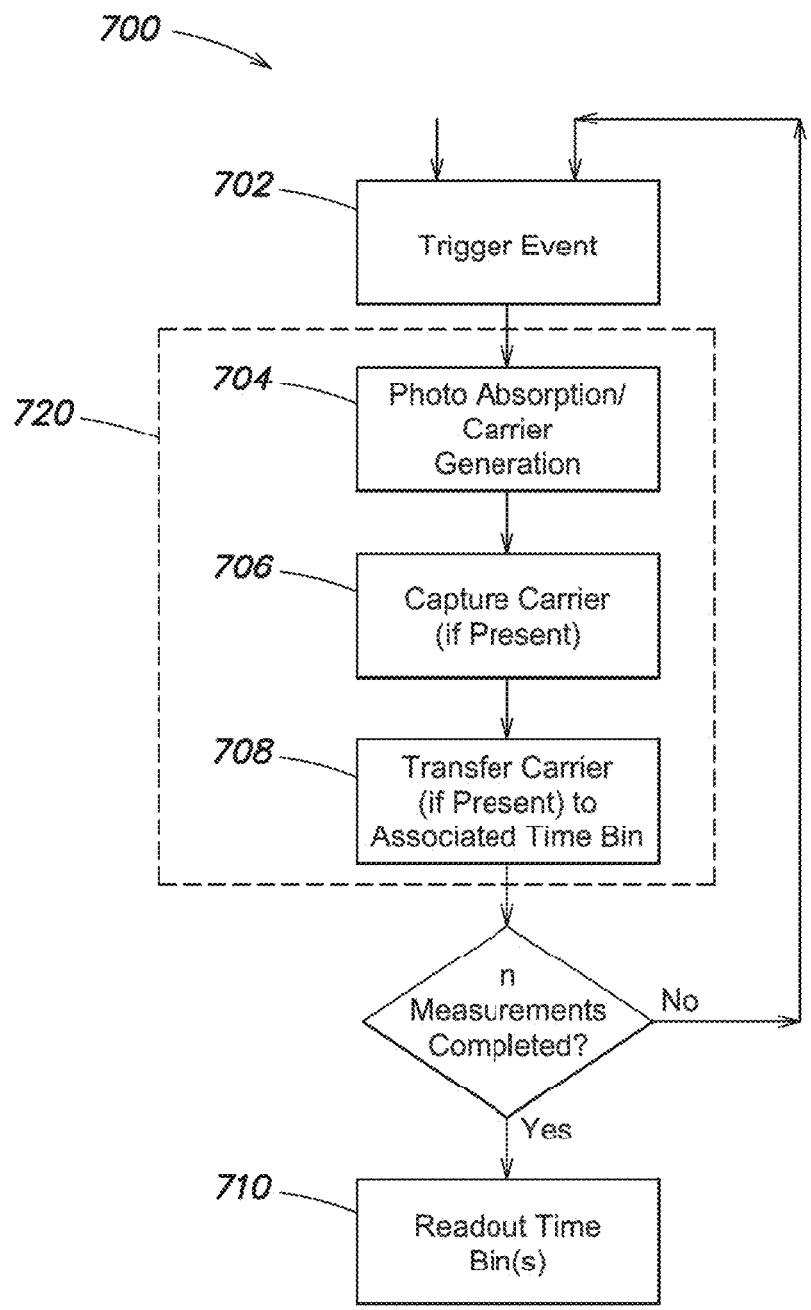
FIG. 8A shows a flowchart of a method that includes performing a plurality of measurements, according to some embodiments.

FIG. 8A shows a flowchart of a method 700 that includes performing a plurality of measurements 720, according to some embodiments. Such a method may be performed at least partially by an integrated device as described herein.

In step 702 a measurement 720 may be initiated by a trigger event. A trigger event may be an event that serves as a time reference for time binning arrival of a photon. The trigger event could be an optical pulse or an electrical pulse, for example, and could be a singular event or a repeating, periodic event. In the context of fluorescence lifetime measurement, the trigger event may be the generation of a light excitation pulse to excite a fluorophore. In the context of time-of-flight imaging, the trigger event may be a pulse of light (e.g., from a flash) emitted by an imaging device comprising the integrated photodetector. The trigger event can be any event used as a reference for timing the arrival of photons or carriers.

The generation of the light excitation pulse may produce a significant number of photons, some of which may reach the pixel 100 and may produce charge carriers in the photon absorption/carrier generation area 102. Since photogenerated carriers from the light excitation pulse are not desired to be measured, they may be allowed to flow down the electric potential to the drain 104 without being captured. Allowing photogenerated carriers produced by a light excitation pulse to flow to the drain 104 without being captured may reduce the amount of unwanted signal that otherwise may need to be prevented from arriving by complex optical components, such as a shutter or filter, which may add additional design complexity and/or cost. The timing of the raising of one or more potential barriers within the carrier travel/capture area 106 may be timed such that photogenerated carriers caused by any unwanted optical signal flow to the drain 104. Moreover, this technique may be used with any number of time bins, including embodiments with only a single time bin. For example, a pixel may include a single time bin and a drain where the timing of the potential barriers reduces signal associated with the excitation pulse while capturing the desired optical signal within the carrier travel/capture area 106.

The measurement 720 may then commence at step 704, in which photon(s) desired to be detected may be absorbed and a charge carrier may be generated in region 102. In the context of fluorescence lifetime measurement or time-of-flight imaging, step 704 may commence after the light excitation pulse is completed.

In step 706 charge carrier(s) moving through the carrier travel/capture area 106 may be captured at predetermined locations at selected times with respect to trigger event 702. In some embodiments, charge carrier(s) may be captured in one or more regions of the carrier travel/capture area 106 by raising one or more potential barriers to trap a carrier in a location that depends upon the time at which it was generated by photon absorption, as discussed above.

In step 708 captured charge carrier(s), if present, may be transferred from the location at which captured charge carrier(s) were captured to a corresponding charge storage bin, thereby "time-binning" the charge carrier.

Following step 708 the measurement 720 may be repeated n-1 times to obtain statistical information regarding the time periods at which photons tend to arrive after a trigger event 702. Time-binned charge carriers may be aggregated in the corresponding charge storage bins as the measurement 720 is repeated. Repeating the measurement 720 may enable aggregating a sufficient number of charge carriers in the charge carrier storage bins to provide statistically meaningful results. For example, in the context of fluorescence lifetime measurement, it may be expected that a photon absorption event in response to a photon received from a fluorophore may occur relatively rarely. For example, such an event may be expected to occur once in about 1,000 measurements. Accordingly, a large number of measurements 720 may need to be performed to aggregate a sufficient number of charge carriers in the charge carrier storage bins such that the results are statistically meaningful. In some embodiments, the number of measurements n of a fluorophore that may be performed for fluorescence lifetime measurement may be 500,000 or more, or 1,000,000 or more, to enable capturing and binning a sufficient number of charge carriers in each bin (i.e., tens or hundreds, or more, in some embodiments).

Once the allotted number of measurements n has been performed, the method 700 may proceed to step 710 of reading out the time bins. Reading out the time bins may include converting the amount of charge aggregated in each of the charge storage bins into corresponding voltages, as will be discussed below.

Figure 8B:
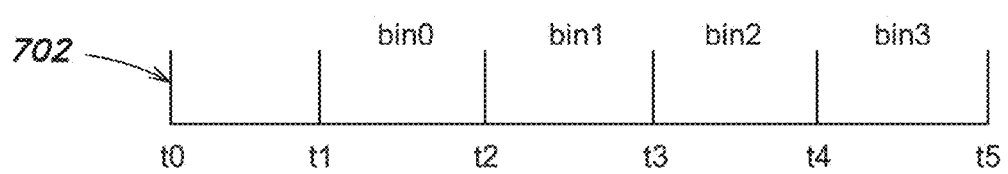
FIG. 8B is a diagram showing an excitation pulse being generated at time t0, and time bins bin0-bin3.

FIG. 8B is a diagram showing an excitation pulse being generated at time t0, and time bins bin0-bin3. Note that in this example the time bins for measuring photons do not begin until t1, a period of time after t0, which lets the excitation light end prior to measuring signal photons.

Figure 8C:
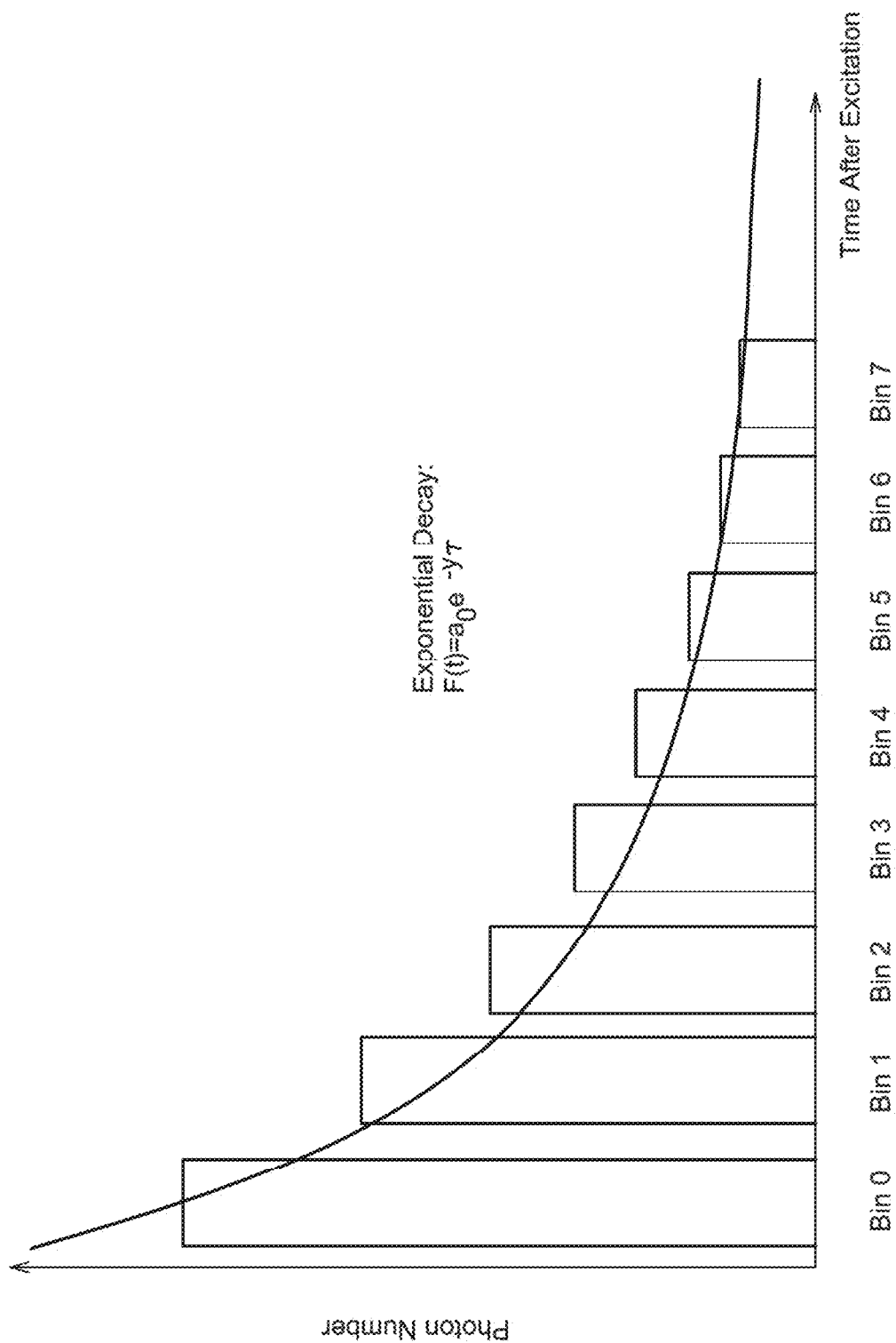
FIG. 8C shows a plot of the number of photons/charge carriers in each time bin for a set of fluorescence lifetime measurements in which the probability of a marker or die fluorescing decreases exponentially over time.

FIG. 8C shows a plot of the number of photons/charge carriers in each time bin for a set of fluorescence lifetime measurements in which the probability of a marker or die fluorescing decreases exponentially over time. By repeating the sequence of excitation, charge capture, and transfer into respective bins many times, and reading out the quantity of charge carriers transferred into each bin, a histogram of the number of photons registered in different bins may be produced that allows determining or approximating the lifetime of a fluorophore.

Method 700 may be performed over any suitable time period in which photons are desired to be captured. In the context of fluorescence lifetime measurement, a suitable period for performing method 700 may be 10 milliseconds, for example. In some embodiments, steps 702 to 708 may be repeated at a frequency that is the MHz range. In some embodiments, the time bins may have a resolution on the scale of picoseconds or nanoseconds.

Temporal Multiplexing of Detection in Response to Different Trigger Events

In some embodiments, measurements may be performed using a plurality of different types of trigger events. The trigger events may be multiplexed in time such that a pixel receives light in response to different types trigger events in different time periods. For example, in the context of luminance lifetime measurements, the trigger events may be excitation light pulses (e.g., laser pulses) of different wavelengths $\lambda_1$ and $\lambda_2$, which can excite different luminescent molecules (e.g., fluorophores). In some embodiments, fluorophores may be identified and/or discriminated from one another based on their response to different wavelengths $\lambda_1$ and $\lambda_2$ of excitation light. Exciting a sample with light excitation pulses of wavelengths $\lambda_1$ and $\lambda_2$ at different times, and analyzing the luminance emitted by the sample in response, can enable detecting and/or identifying luminescent molecules based on whether luminescence is detected in a first time period in response to excitation light of wavelength $\lambda_1$, or in a second time period in response to excitation light of wavelength $\lambda_2$. In addition to, or as an alternative to such temporal multiplexing, luminescent molecules may be identified and/or discriminated based upon measuring their luminance lifetimes.

In some embodiments, a nucleic acid may be sequenced based upon detecting light emitted by one or more fluorophores attached to nucleotides of the nucleic acid. In some embodiments, such sequencing may be performed by temporal multiplexing of excitation light of different wavelengths, based upon measuring luminance lifetimes, or based upon a combination of such techniques.

For example, in some embodiments, four different fluorophores may be linked to respective nucleotides (e.g., A, C, G and T) of a nucleic acid. The four fluorophores may be distinguishable from one another based upon a combination of excitation wavelength and luminance lifetime, as illustrated in the chart below.

|  | $\lambda_1$ | $\lambda_2$ |
| --- | --- | --- |
| Short Lifetime | Fluorophore 1 | Fluorophore 3 |
| Long Lifetime | Fluorophore 2 | Fluorophore 4 |

In some embodiments, the integrated photodetector may temporally multiplex detection of photons produced by a sample in response to light excitation pulses of different wavelengths. For example, in a first time period, light produced by a sample in response to excitation light of wavelength $\lambda_1$ may be detected. Subsequently, in a second time period, light produced by a sample in response to excitation light of wavelength $\lambda_2$ may be detected. To do so, a pixel having a plurality of time bins may use a first subset of time bins to detect arrival of photons in the first time period and a second subset of time bins to detect arrival of photons in the second time period. By examining whether light arrives at a pixel during the first time period or the second time period, it can be determined whether a fluorophore is fluorescing in response to light of wavelength $\lambda_1$ or light of wavelength 2.

In some embodiments, information regarding the arrival times of photons in response to a light excitation pulse can be used to determine and/or discriminate fluorescence lifetime, and thereby identify a fluorophore. In some embodiments, a first excitation pulse of a first wavelength may be emitted, then a first subset of the time bins of a pixel may be used to time-bin the arrival of incident photons in a first time interval. Then, a second excitation pulse of a second wavelength may be emitted, and a second subset of time bins of the pixel may be used to time-bin the arrival of incident photons in a second time interval. Accordingly, if photons are received in the first time interval and/or the second time interval, information about the lifetime of the fluorophore that produced the photons can be obtained. Repeating the process of temporal multiplexing of light excitation pulses along with measuring information regarding fluorescence lifetimes can provide sufficient information to enable identification of the fluorophore. Accordingly, the nucleotide to which the fluorophore is attached may be identified. As a sequencing reaction progresses, additional nucleotides may be incorporated into a polymerase over time. Performing and repeating the process of temporal multiplexing of light excitation pulses with measurements of fluorescence lifetimes can provide sufficient information to enable identification of such fluorophores. Accordingly, the sequence of nucleotides in a nucleic acid can be determined.

Figure 8D:
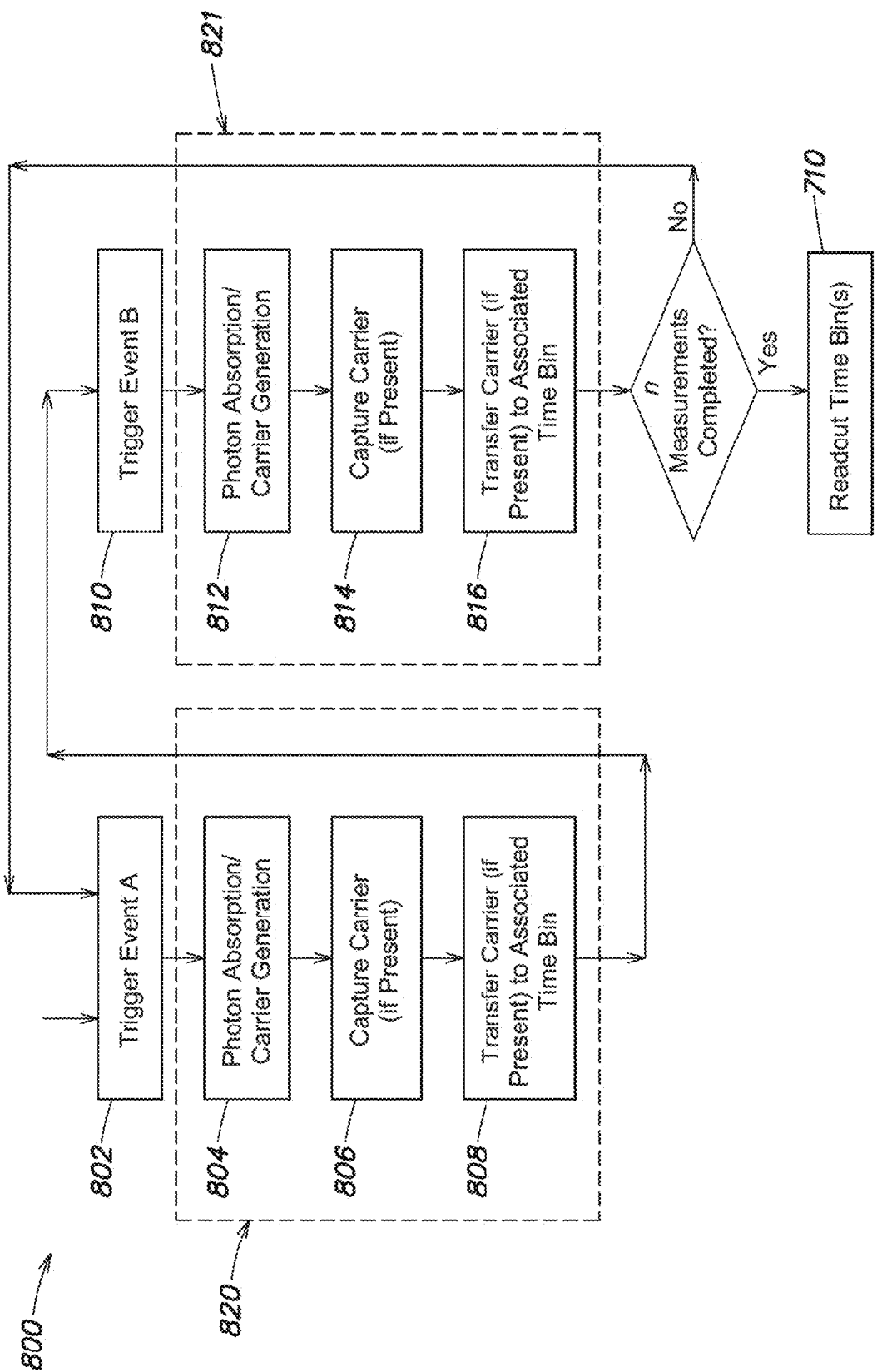
FIG. 8D shows a method of operating the integrated photodetector according to some embodiments in which light is received at the integrated photodetector in response to a plurality of different trigger events.
Figure 8E:
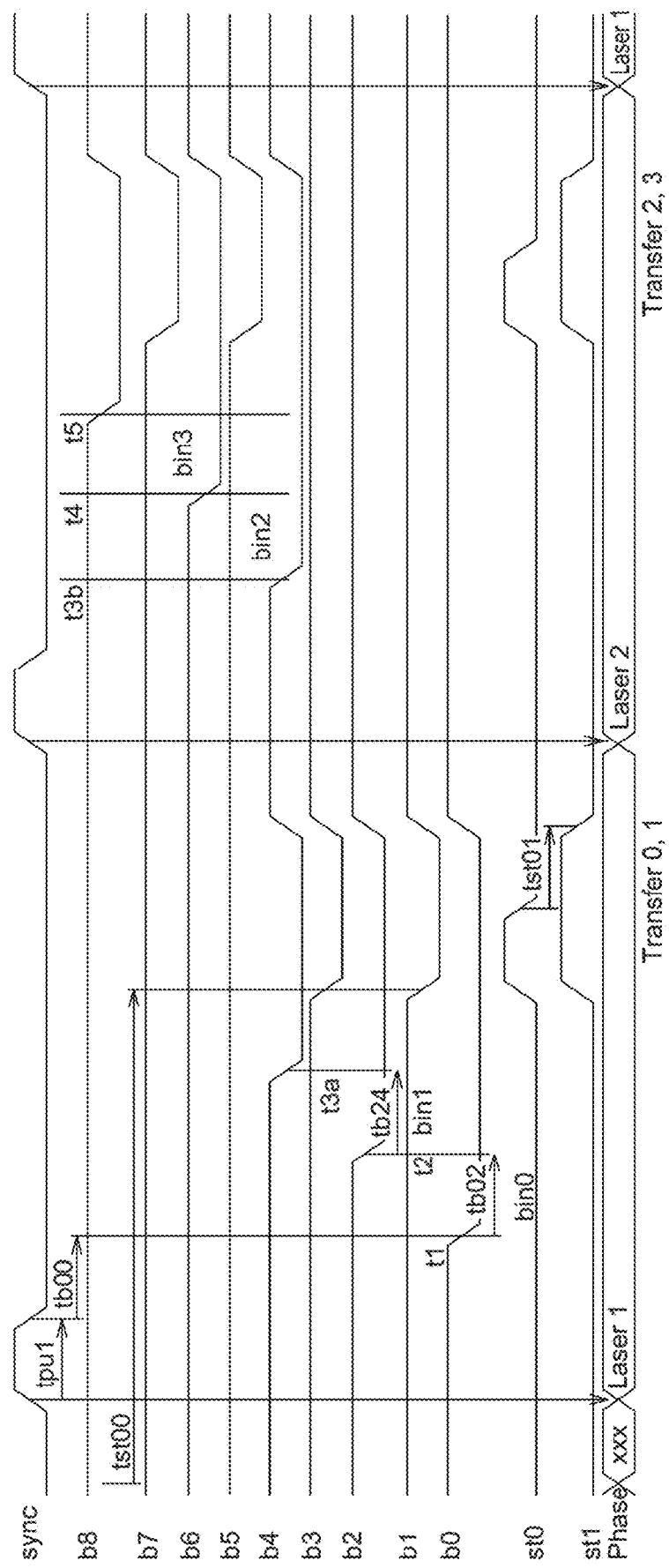
FIG. 8E illustrates voltages of the electrodes of the charge carrier segregation structure when performing the method of FIG. 8D.

FIG. 8D shows a method of operating the integrated photodetector according to some embodiments in which light is received at the integrated photodetector in response to a plurality of different trigger events. FIG. 8E illustrates voltages of the electrodes of the charge carrier segregation structure when performing the method of FIG. 8D.

In step 802, a measurement 820 may be initiated by a trigger event A. Trigger event A may be an event that serves as a time reference for time binning arrival of a photon. The trigger event may be an optical pulse or an electrical pulse, for example, and could be a singular event or a repeating, periodic event. In the context of fluorescence lifetime measurement, the trigger event A may be the generation of a light excitation pulse at a first wavelength to excite a first type of fluorophore.

The generation of the light excitation pulse may produce a significant number of photons, some of which may reach the pixel 100 and may produce charge carriers in the photon absorption/carrier generation area 102. Since photogenerated carriers from the light excitation pulse are not desired to be measured, they may be allowed to flow down the electric potential to the drain 104 without being captured, as discussed above. The raising of one or more potential barriers within the carrier travel/capture area 106 may be timed such that photogenerated carriers caused by any unwanted optical signal flow to the drain 104.

The measurement 820 may then proceed at step 804, in which photon(s) desired to be detected may be absorbed and a charge carrier may be generated in region 102. In the context of fluorescence lifetime measurement, step 804 may commence after the light excitation pulse is completed.

In step 806, charge carrier(s) moving through the carrier travel/capture area 106 may be captured at predetermined locations at selected times with respect to trigger event 802. In some embodiments, charge carrier(s) may be captured in one or more regions of the carrier travel/capture area 106 by raising one or more potential barriers to trap a carrier in a location that depends upon the time at which it was generated by photon absorption, as discussed above. In some embodiments, step 806 may include raising potential barriers 501, 503 and 503 in succession, thereby capturing charge (if present) corresponding to time bins bin0 and/or bin1.

In step 808, captured charge carrier(s), if present, may be transferred from the location at which they were captured to a corresponding charge storage bin, thereby "time-binning" the charge carrier. For example, any charge captured corresponding to time bins bin0 and/or bin1 may be transferred to bins bin0 and/or bin1 in step 808 using a technique shown in FIGS. 7A-7D, for example.

In step 810, a second measurement 821 may be initiated by a trigger event B. Trigger event B may be an event that serves as a time reference for time binning arrival of a photon. The trigger event may be an optical pulse or an electrical pulse, for example, and could be a singular event or a repeating, periodic event. In the context of fluorescence lifetime measurement, the trigger event B may be the generation of a light excitation pulse at a second wavelength to excite a second type of fluorophore.

The generation of the light excitation pulse may produce a significant number of photons, some of which may reach the pixel 100 and may produce charge carriers in the photon absorption/carrier generation area 102. Since photogenerated carriers from the light excitation pulse are not desired to be measured, they may be allowed to flow down the electric potential to the drain 104 without being captured, as discussed above. The raising of one or more potential barriers within the carrier travel/capture area 106 may be timed such that photogenerated carriers caused by any unwanted optical signal flow to the drain 104.

The second measurement 821 may then proceed at step 812, in which photon(s) desired to be detected may be absorbed and a charge carrier may be generated in region 102. In the context of fluorescence lifetime measurement, step 812 may commence after the second light excitation pulse is completed.

In step 814, charge carrier(s) moving through the carrier travel/capture area 106 may be captured at predetermined locations at selected times with respect to trigger event 810. In some embodiments, charge carrier(s) may be captured in one or more regions of the carrier travel/capture area 106 by raising one or more potential barriers to trap a carrier in a location that depends upon the time at which it was generated by photon absorption, as discussed above. In some embodiments, step 814 may include raising potential barriers 503, 504 and 505 in succession, thereby capturing charge (if present) corresponding to time bins bin2 and/or bin3.

In step 816, captured charge carrier(s), if present, may be transferred from the location at which they were captured to a corresponding charge storage bin, thereby "time-binning" the charge carrier. For example, any charge captured corresponding to time bins bin2 and/or bin3 may be transferred to bins bin2 and/or bin3 in step 816 using a technique shown in FIGS. 7A-7D, for example.

Although an example has been described in which a pixel has four time bins, and two bins are allocated to measuring arrival times of light produced in response to each of the respective light excitation pulses, the techniques described herein are not limited in this respect. For example, the pixel may have a larger or smaller number of bins, which may be allocated in any suitable way to measuring light in response to different excitation pulses. Further, the techniques described herein are not limited to light excitation pulses of two different wavelengths, as light excitation pulses of any number of wavelengths may be used, and multiplexed accordingly.

Following step 816, the measurements 820 and 821 may be repeated n−1 times to obtain statistical information regarding the time periods at which photons tend to arrive after a trigger event. Time-binned charge carriers may be aggregated in the corresponding charge storage bins as the measurements are repeated.

Once the allotted number of measurements n has been performed, the method 800 may proceed to step 710 of reading out the time bins. Reading out the time bins may include converting the amount of charge aggregated in each of the charge storage bins into corresponding voltages, as will be discussed below.

Example Readout Circuitry and Sequences

As illustrated in FIGS. 2A and 2B, pixel 100 may include readout circuitry 110 that allows reading out the charge stored in the charge storage bin(s) of the charge carrier storage region 108. Pixel 100 may be an active pixel, such that readout circuitry 110 includes a readout amplifier, or a passive pixel in which readout circuitry 110 does not include a readout amplifier. Any suitable type of active pixel or passive pixel readout circuitry may be used.

If readout circuitry 110 includes a readout amplifier, any suitable type of amplifier may be used. Examples of suitable amplifiers include amplifiers abased on a common source configuration and amplifiers abased on a source-follower configuration. However, the techniques described herein are not limited as to any particular amplifier configuration.

If readout circuitry 110 includes a readout amplifier, the readout amplifier may take the charge accumulated in a charge storage bin (e.g., bin0, bin1, bin2 or bin3) as an input and produce a voltage representative of the charge in the charge storage bin as an output.

One example of readout circuitry 110 based on a source-follower configuration is illustrated in FIG. 4. The example of readout circuitry 110 shown in FIG. 4 is a "4T" configuration having four transistors: rt, sf, rs, and one of the transfer gates tx0-tx3. Since the three transistors rt, sf, and rs are shared among each charge storage bin, the example circuitry shown in FIG. 4 for all four bins is a "1.75T" configuration, (4 transfer gates+3 transistors)/4 bins. However, the techniques described herein are not limited to using readout circuitry 110 having a 1.75T configuration, as any other suitable type of readout configuration may be used.

Further, any suitable readout techniques may be used, including noise reduction techniques. In some embodiments, readout circuitry 110 may read out the charge carrier storage bins using correlated double sampling. Correlated double sampling is technique in which a first sample may be taken of a node at a reset voltage level which includes an undetermined amount of noise, and a second sample may be taken of a signal level at the node including the same undetermined noise. The noise can be subtracted out by subtracting the sampled reset level from the sampled signal level.

Figure 9A:
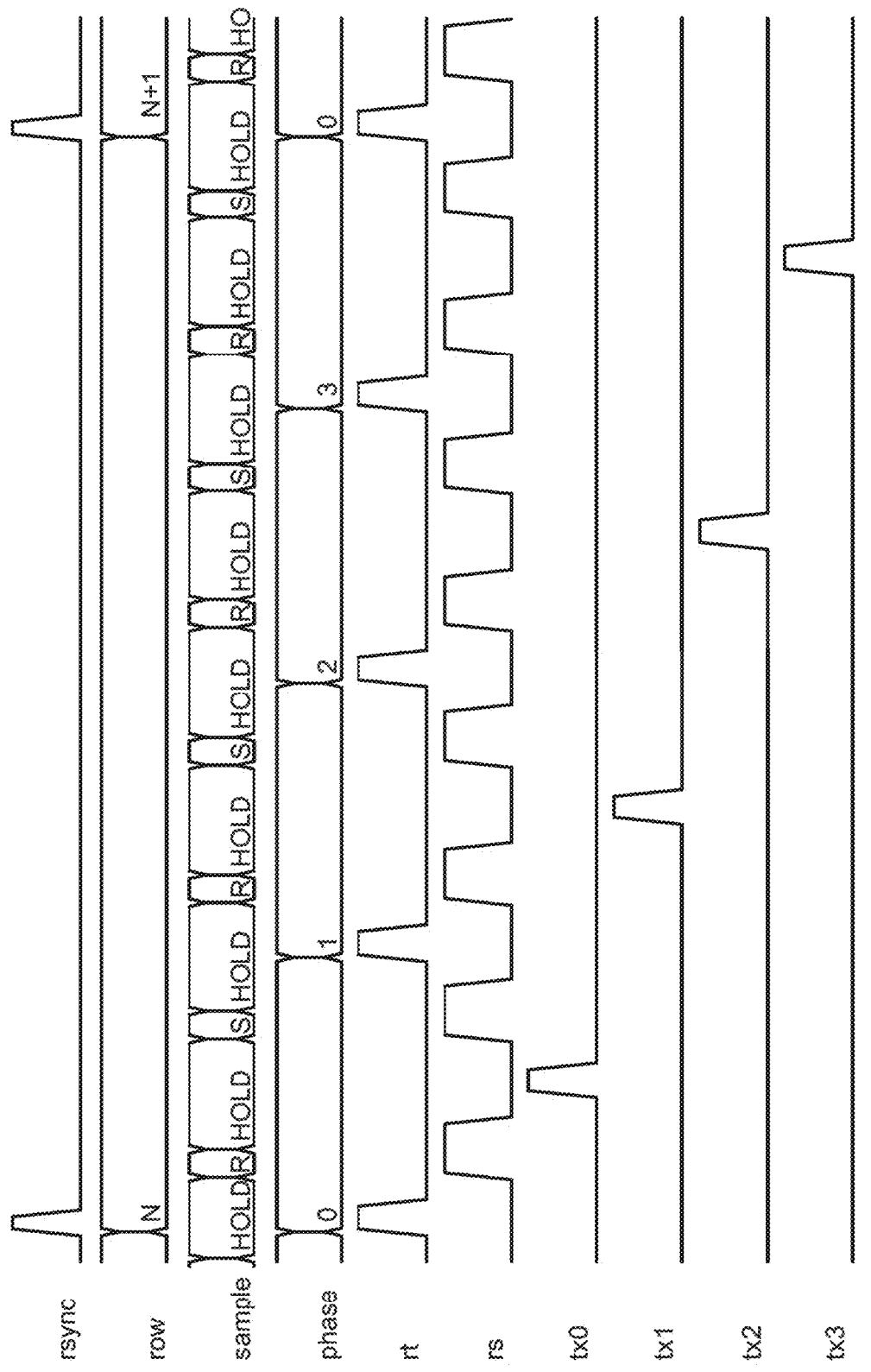
FIG. 9A shows an example of a timing diagram for sequentially reading out bins bin0-bin3 using correlated double sampling.

Readout circuitry 110 may perform readout of the charge storage bins sequentially or in parallel. An example of a timing diagram for sequentially reading out bins bin0-bin3 with readout circuitry 110 shown in FIG. 4 using correlated double sampling is shown in FIG. 9A. As shown in FIG. 9A, initially reset transistor rt may be turned on to set the floating diffusion node fd to a reset voltage ct. During the time period in which the voltage of the floating diffusion node is reset the transfer gates tx0-tx3 are turned off to keep the charge carriers stored in their respective bins. After the floating diffusion node fd is reset the reset voltage may be sampled by turning off transistor rt and turning on transistor rs to produce an output voltage cb. The reset voltage represented by output voltage cb may be stored in an analog format (e.g., on a capacitor) or in a digital format (e.g., by A/D conversion and storage). Then, transfer gate tx0 may be turned on to allow the charge from bin0 to flow to the floating diffusion fd. The signal voltage may be sampled by turning on transistor rs to produce an output voltage cb based on the charge stored in bin0. The signal voltage represented by output voltage cb may be stored in an analog format (e.g., on a capacitor) or in a digital format (e.g., by A/D conversion and storage).

Then, transistor rt may be turned on to set the floating diffusion fd to a reset voltage ct. During the time period in which the voltage of the floating diffusion node fd is reset the transfer gates tx0-tx3 are turned off to keep the charge carriers stored in their respective bins. After the floating diffusion node fd is reset the reset voltage may be sampled by turning off transistor rt and turning on transistor rs to produce an output voltage cb. Again, the reset voltage represented by output voltage cb may be stored in an analog format (e.g., on a capacitor) or in a digital format (e.g., by A/D conversion and storage). Then, transfer gate tx1 may be turned on to allow the charge from bin1 to flow to the floating diffusion. The signal voltage may be sampled by turning on transistor rs to produce an output voltage cb based on the charge stored in bin1. Again, the signal voltage represented by output voltage cb may be stored in an analog format (e.g., on a capacitor) or in a digital format (e.g., by A/D conversion and storage).

The same process may then be performed for bin2 and bin3 by performing a reset, sampling the reset voltage, transferring the charge from a bin to the floating diffusion node fd, and sampling the signal. Accordingly, in the readout sequence illustrated in FIG. 9A, eight samples may be taken representing the reset value and signal values for the four bins. The stored reset value for each bin may be subtracted from the stored signal value to obtain a result indicative of the charge stored in each bin, thus completing the correlated double sampling process.

Optionally, as discussed above, the sampled reset voltage level for a bin may be stored on a first capacitor and the sampled signal for the bin may be stored on a second capacitor. Optionally, before sampling the reset level and signal level onto the capacitors the capacitors may be cleared by setting them to the same voltage.

FIG. 9B shows a readout sequence for performing correlated double sampling that does not require measuring a reset value for each signal value, according to some embodiments. In the example of FIG. 9B, a single reset value is measured for all the bins of the pixel. To obtain the signal for the first bin, a reset value may be subtracted from the measured signal value, as discussed above. Instead of resetting the floating diffusion at this point, charge may be transferred to the floating diffusion from the second bin, thereby aggregating the charge for the first and second bins. The signal for the second bin can be obtained by subtracting the signal for the first bin from the aggregated signal for the first and second bins. Since both the signal for the first bin and the aggregated signal for the first and second bins include the same reset noise, the result is that the reset noise is subtracted out. The process may continue for the remaining bins, with the aggregated signal for the previous bin being subtracted from the aggregated signal for the next bin. Aggregating the stored charge for the bins in this manner can allow reading our larger signals than would be the case if each bin were read out individually, and can reduce noise, as the sampled signals will be higher above the noise floor than would be the case if each bin were read out individually. In the example with four time bins, five samples may be taken—one reset value and four samples representing the cumulative charge stored in the charge storage bins. This process will be described in greater detail with reference to FIG. 9B.

As shown in FIG. 9B, initially reset transistor rt may be turned on to set the floating diffusion node fd to a reset voltage ct. During the time period in which the voltage of the floating diffusion node is reset the transfer gates tx0-tx3 are turned off to keep the charge carriers stored in their respective bins. After the floating diffusion node fd is reset the reset voltage may be sampled by turning off transistor rt and turning on transistor rs to produce an output voltage cb. The reset voltage represented by output voltage cb may be stored in an analog format (e.g., on a capacitor) or in a digital format (e.g., by A/D conversion and storage). Then, transfer gate tx0 may be turned on to allow the charge from bin0 to flow to the floating diffusion. The signal voltage for bin0 may be sampled by turning on transistor rs to produce an output voltage cb based on the charge stored in bin0.

Then, transfer gate tx1 may be turned on to allow the charge from bin1 to flow to the floating diffusion. The signal voltage for bin1+bin0 may be sampled by turning on transistor rs to produce an output voltage cb based on the charge stored in bin1 plus the charge stored on bin0. The output signal value for bin0 may be subtracted from the output signal value for bin0+bin1 to produce a signal indicative of the charge stored on bin1.

A similar process may then be performed for bin2 and bin3 by subtracting the measured signal level for bin n from the measured signal level for bin n+1. Accordingly, using such a technique the number of samples that may need to be taken may be reduced.

The following formulas show how to calculate the "corrected" (using correlated double sampling) signal for each bin using only a single measured reset value.

corrected signal bin0=measured signal bin0−reset level corrected signal bin1=measured signal for (bin0+ bin1)−measured signal bin0 corrected signal bin2=measured signal for (bin0+ bin1+bin2)−measured signal for (bin 0+bin1)

corrected signal bin3=measured signal for (bin0+ bin1+bin2+bin3)−measured signal for (bin0+ bin1+bin2)

In some embodiments, oversampling of the readout from a pixel may be performed. Oversampling involves reading the same signal from the pixel a plurality of times. Each time a signal is read from the pixel, there may be slight variations in the signal that is read due to noise. Oversampling of the readout of a signal and averaging the samples can reduce the noise (e.g., white noise) in measurements. In some embodiments, multiple samples may be taken (e.g., 4-8 samples) to read a single nominal signal value from the pixel (e.g., a single reset level or signal level). In some embodiments, each of the samples of a signal may be read out through the readout signal change and converted into digital values (e.g., digital words). The average of the samples may then be calculated, and the average used as the measured signal from the pixel. For example, if oversampling by 8× is used, eight samples may be taken for each reset and signal value, for a total of 64 samples in the case of measuring 4 time bins and 4 reset levels, or 40 samples in the case of measuring 1 reset level and 4 aggregated signal levels.

Pixel Array Readout Circuitry

Readout in Parallel, Sequential Readout, and Readout with a Combination of Parallel and Sequential Readout As discussed above, the pixel array may include a plurality of pixels arranged in rows and columns. In some embodiments, readout may be performed row by row. In some embodiments, a row of the pixel array may be selected, and a readout process may be performed for the selected row of pixels. The readout circuitry for a column of pixels may be common to the pixels in the column, such that readout may be performed by the readout circuitry for respective pixels in the column as different rows are selected. Readout for a selected row may be performed in parallel (termed "column parallel"), sequentially, or a combination of parallel and sequentially (termed "semi-column parallel").

To perform readout of the pixels of a selected row in column parallel, individual readout circuitry may be provided for each column so that the pixels of each column in the selected row can be read out at the same time, as illustrated in FIG. 10A. FIG. 10A illustrates an array of pixels having a plurality of columns C1 to Cn and a plurality of rows, with a selected row Ri being shown by way of illustration. In the embodiment of FIG. 10A, each column of pixels has an associated readout circuit 905. Since each column of pixels has an associated readout circuit 905, the signals from each pixel in row Ri can be read out at the same time.

To perform readout of the pixels of a selected row in sequence, individual readout circuitry need not be provided for each column. For example, in some embodiments a common readout circuit may be provided, and each pixel of the selected row may be read out sequentially. FIG. 10B shows an embodiment in which a common readout circuit 905 may be provided for a plurality of columns. The common readout circuit may be selectively connected to a column by a switch network 906 under the control of suitable control circuitry. For example, in some embodiments, switch network 906 may be sequentially connect individual columns of pixels to the readout circuit 905.

To perform readout of the pixels in semi-column parallel, a plurality of readout circuits 905 may be provided, fewer than the number of columns, as illustrated in FIG. 10C. In such a semi-column parallel architecture, each readout circuit 905 may be shared by a subset of the columns. Each readout circuit 905 may sequentially read out a subset of columns in the array. As shown in FIG. 10C, readout circuit 905A may be selectively connected to its respective columns by a switch network 906A. Readout circuit 905B may be selectively connected to its respective columns by a switch network 906B.

In some embodiments, a readout circuit 905 may include one or more amplifier(s) to amplify a signal from a pixel and an analog to digital converter to convert the amplified signal into a digital value. Examples of configurations of readout circuits 905 according to various embodiments are described below.

Sample and Hold Circuit

Figure 10D:
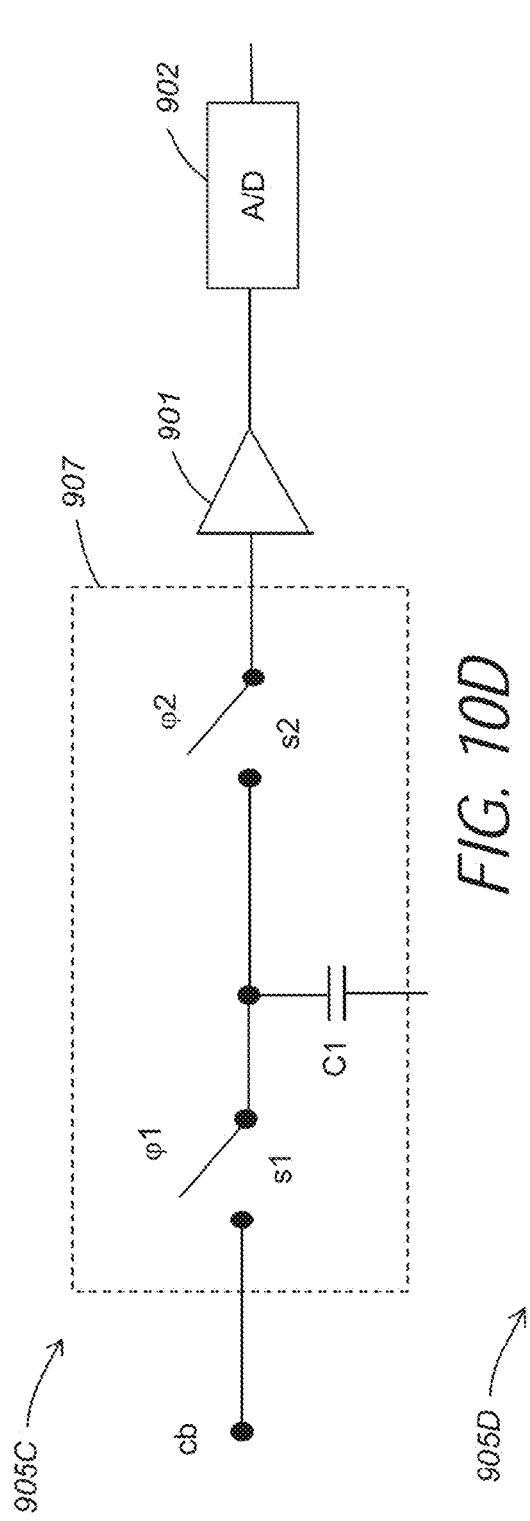
FIG. 10D shows a circuit diagram illustrating column readout circuitry which includes sample and hold circuitry, amplifier circuitry and an analog-to-digital (A/D) converter.

In some embodiments, the readout circuitry for a column may include one or more sample and hold circuits. FIG. 10D shows a circuit diagram illustrating column readout circuitry 905C, which includes sample and hold circuitry 907, amplifier circuitry 901, and an analog-to-digital (A/D) converter 902. The sample and hold circuit 907 may sample the output voltage from a pixel (e.g., at node cb) onto a capacitive element (e.g., a capacitor), and then hold the voltage on the capacitor while it is read out by an amplifier. As discussed above, the output voltage from the pixel may represent the number of charge carriers captured during one or more time intervals.

The sample and hold circuit may operate in a plurality of phases, termed a "sample" phase and a "hold" phase. In the "sample" phase, the voltage value from the pixel may be sampled onto a capacitive element. The voltage to be read out is thus stored on the capacitive element. Following the "sample" phase, the voltage of the capacitor is read in the "hold" phase. During the "hold" phase, the voltage of the capacitor may be read out from the capacitive element and processed by one or more amplifiers and then converted into digital form by an analog to digital (A/D) converter. As illustrated in FIG. 10D, during the sample phase ($\varphi 1$), switch s1 is turned on (set in its conductive state) and switch s2 is turned off (set in its non-conductive state), thereby sampling the voltage from readout terminal cb of a pixel onto a capacitive element, e.g., capacitor C1. The hold phase ($\varphi 2$) follows the sample phase. During the hold phase the switch s1 is turned off and the switch s2 is turned on, thereby connecting the capacitor C1 to the amplifier circuitry 901. By turning off switch S 1, the voltage of the capacitor may be held substantially constant while the voltage is read, as the amplifier circuitry 901 may have a high input impedance. The amplified signal from the amplifier circuitry 901 may be provided to an A/D converter 902 to convert the amplified voltage into a digital value.

In some embodiments, power consumption and/or cost can be reduced by reducing or minimizing the number of circuits (e.g., amplifiers, analog to digital converters) used. In some embodiments, to reduce or minimize the number of circuits in the readout chain one or more circuits of the readout chain may be shared by more than one column of the pixel array.

Multiplexing Readout Circuitry Component(s)

Figure 10E:
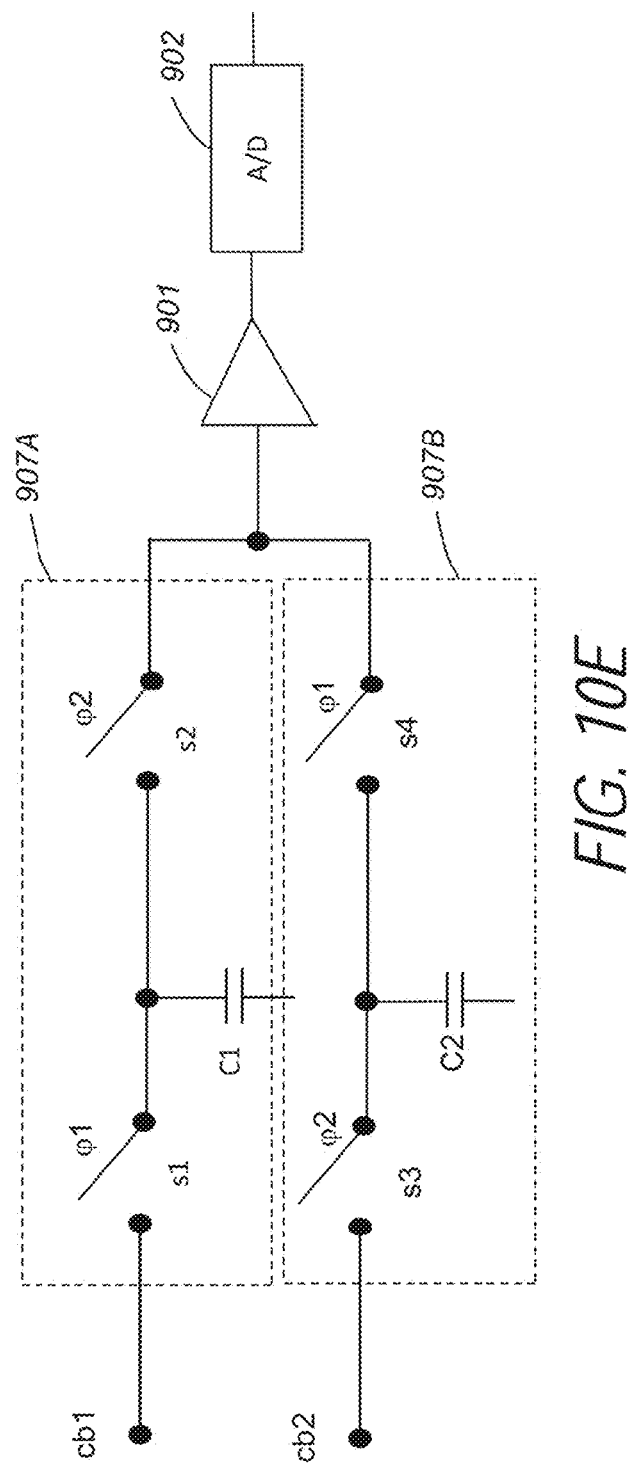
FIG. 10E illustrates an embodiment of readout circuitry in which both the amplifier circuitry and the A/D converter are shared by two columns of the pixel array.

In some embodiments, one or more components of the readout circuitry may be shared by two or more columns of the pixel array. For example, as shown in FIG. 10E, all or a portion of amplifier circuitry 901, the A/D converter 902, or both, may be shared by two or more columns of the pixel array. FIG. 10E illustrates an embodiment of readout circuitry 905D in which both the amplifier circuitry 901 and the A/D converter 902 are shared by two columns of the pixel array. In the embodiment of FIG. 10E, respective column lines are connected to respective pixel nodes cb1 and cb2. Each column line is connected to a respective sample and hold circuit 907A, 907B. Amplifier circuitry 901 and A/D converter 902 may be shared by both columns. The input to the amplifier circuitry 901 may be multiplexed between the sample and hold circuits 907A and 907B such that their outputs are connected to the amplifier circuitry 901 at different times (e.g., sequentially). By using shared readout circuit components such as amplifier circuitry 901 and/or A/D converter 902, the number of components in the readout circuitry can be reduced, which can reduce the cost and/or power consumption of the readout circuitry.

In some embodiments, the sample and hold phases for the columns sharing the amplifier circuitry 901 may be alternated, such that when a the column is in the sampling phase and not connected to the amplifier circuitry 901, the other column is in the hold phase and its sample and hold circuit is connected to amplifier circuitry 901 to amplify the voltage it previously sampled. In the embodiment of FIG. 10F, the sample and read phases are alternated between the two columns, with the upper column being in the sample phase during phase 1 and in the hold phase during phase 2, and the lower column being in the sample phase during phase 2 and the hold phase during phase 1. During phase 1 (φ1), the signal from node cb 1 is sampled onto capacitor C1 by turning on switch s1, and switch s2 is turned off, switch s3 is turned off, and capacitor C2 is connected to the amplifier 901 via switch s4, which is turned on. During phase 2 (φ2), the signal from node cb 2 is sampled onto capacitor C2 by turning on switch s3, switch s4 is turned off, switch s1 is turned off, and capacitor C1 is connected to the amplifier 901 via switch s2, which is turned on. Sharing the amplifier circuitry 901 by more than one column may reduce the downtime of amplifier circuitry 901, as it does not need to sit idle during a sampling phase for a column.

In some embodiments, more than two columns of the pixel array may share readout circuitry 901 and/or A/D converter 902. FIG. 10F shows an embodiment in which n columns of the pixel array share readout circuitry 901 and/or A/D converter 902. Capacitors C1-Cn may be sequentially connected to the readout circuitry 901 to read out their voltage values. Capacitors C1-Cn may be connected to the readout circuitry 901 in any suitable order. The sampling phase of the respective sample and hold circuits for each column may be timed to occur during a period in which the sample and hold circuit is not being read out by the amplifier circuitry 901. In some embodiments, and as discussed above, the sampling phases may be timed to occur during a time interval in which the amplifier circuitry 901 is reading out a different row, to limit the amount of time the amplifier circuitry 901 sits idle. For example, as discussed above, the voltage from node cb1 may be sampled on capacitor C1 during phase 1. During phase 2, the voltage of capacitor C1 may be read out by amplifier circuitry 901 and the voltage from node cb2 may be sampled on capacitor C2. During phase 3, the voltage of capacitor C2 may be read out by amplifier circuitry 901 and the voltage from a third node cb3 may be sampled on a third capacitor C3, etc. The process may then begin again with phase 1 starting during the time the last column (row n) is read out by amplifier circuitry 901, or after the last column is read out by amplifier circuitry 901. Any suitable number of columns may share amplifier circuitry 901, such as 2, 4, 8, 16, 32, 64, 128, etc., or any other suitable number (which need not be a power of 2).

Figure 10G:
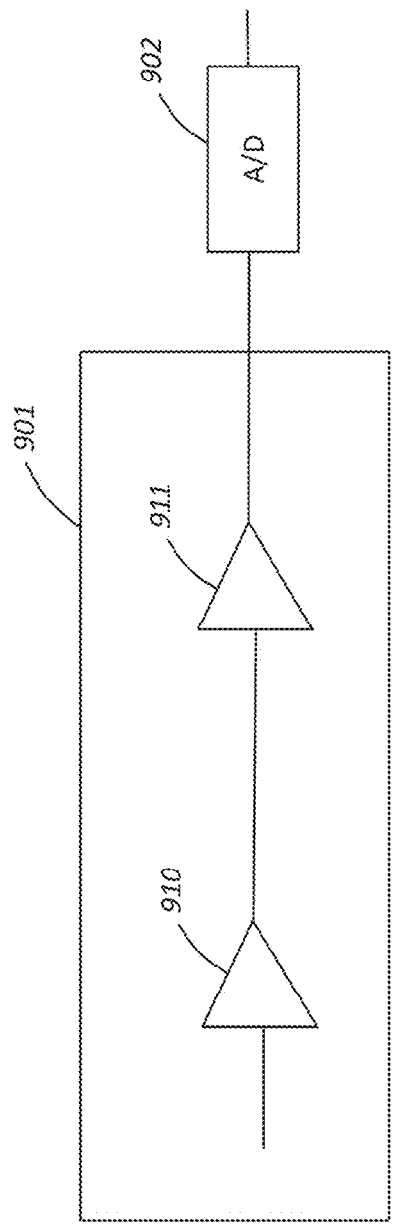
FIG. 10G shows an example of amplifier circuitry that includes a plurality of amplifiers.

FIG. 10G shows a diagram of readout circuitry including amplifier circuitry 901. In the embodiment of FIG. 10G, amplifier circuitry 901 includes a plurality of cascaded amplifiers 910 and 911. Using a plurality of cascaded amplifiers 910 and 911 can reduce power consumption, as achieving the desired signal gain may be achieved with less power dissipation when a plurality of amplifiers 910 and 911 are used as opposed to using a single amplifier to achieve the same gain.

Figure 10H:
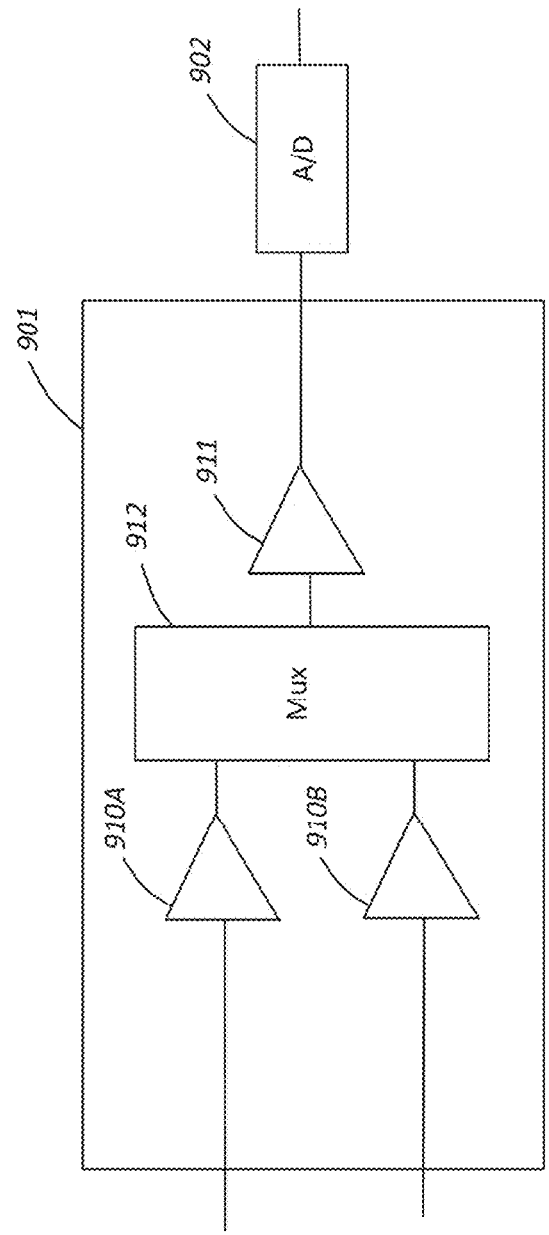
FIG. 10H shows a diagram of readout circuitry including amplifier circuitry having first stage amplifiers for respective columns and a second stage amplifier that is shared by the two columns.

FIG. 10H shows a diagram of readout circuitry including amplifier circuitry 901 having first stage amplifiers 910A and 910B for respective columns and a second stage amplifier 911 that is shared by the two columns. A multiplexer 912 connects first stage amplifiers 910A and 910B to the second stage amplifier 911 at different times. In some embodiments, the amplifiers 910A, 910B and 911 may be differential amplifiers.

Figure 10I:
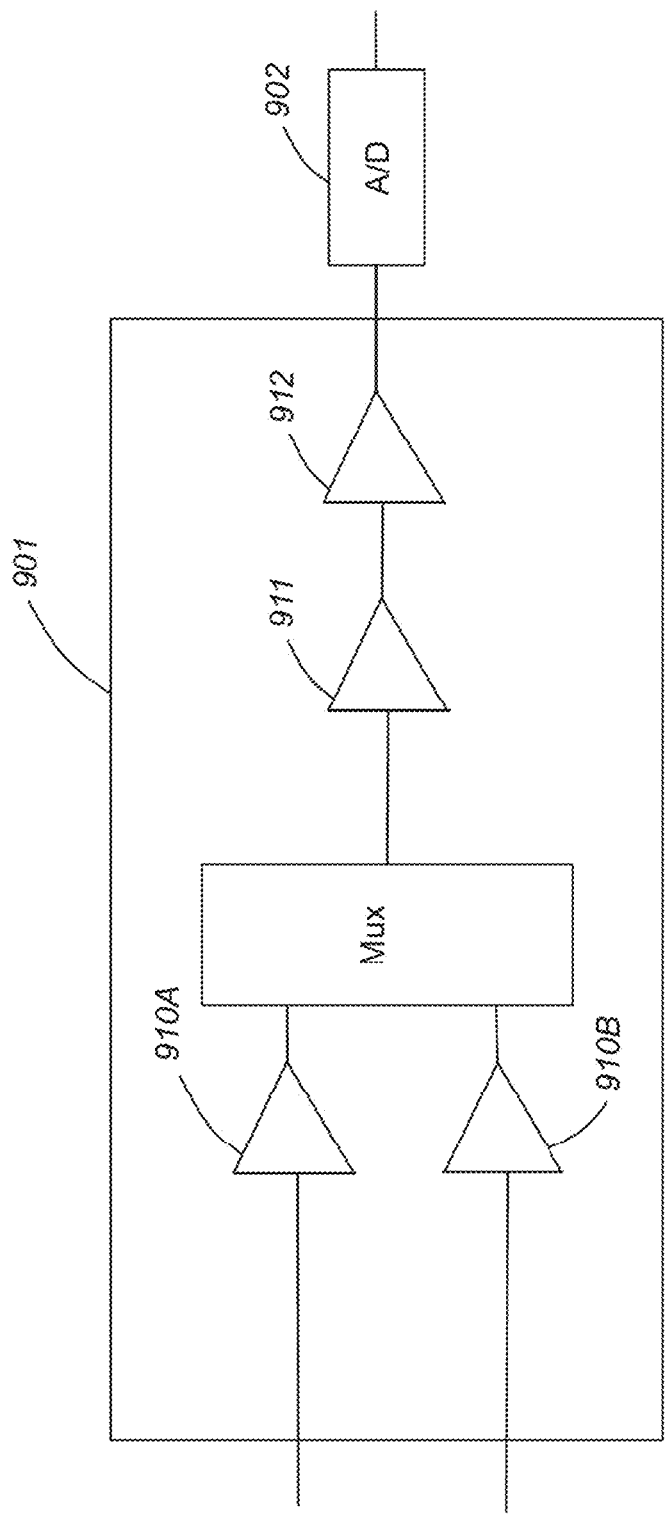
FIG. 10I shows a diagram of readout circuitry including first-stage amplifiers, a second stage amplifier and a third stage amplifier.

FIG. 10I shows a diagram of readout circuitry including first-stage amplifiers 910A and 910B, a second stage amplifier 911 and a third stage amplifier 912. As discussed above, using an additional amplifier stage to achieve a desired gain value may reduce power consumption with respect to using fewer amplifier stages to achieve the desired gain value. In some embodiments, the amplifiers 910A, 910B, 911 and 912 may be differential amplifiers.

In some embodiments, gain may be applied in the signal chain in a plurality of stages. In some embodiments, the first-stage amplifier (e.g., 910A, 910B) may have a gain of 2 or more, the second stage amplifier (e.g., 911) may have a gain of 1-8, or more, and the third stage amplifier (e.g., 912) may have a gain of 1-2, or more, for an overall gain of the three stages of 2-32, or more.

In some embodiments, the amplifiers may have a digitally programmable gain. The gain of one or more stages may be changed depending on the characteristics of the light being received. For example, if more than one wavelength of light excitation pulse (e.g., laser pulse) is used that produce different responses in the pixel, the gain of one or more amplifiers in the readout chain may be changed depending on which wavelength of light is currently being detected. If one wavelength results in smaller number of charge carriers being produced, the gain may be increased to accommodate the reduced signal level. If another wavelength results in a larger number of charge carriers being produced, the gain may be decreased. In some embodiments, the gains of the readout chain for different wavelengths may be normalized to one another to produce the same output levels in response to different wavelengths.

Readout Circuitry Design Considerations

Since in some embodiments, the number of charge carriers captured for each time bin may be relatively small, e.g., on the order of hundreds of charge carriers, the signal to be detected from each pixel may be relatively small. Accordingly, in some embodiments the signal chain running from a pixel to (and including) an analog to digital converter may include low-noise readout circuitry. Techniques and circuits for limiting the noise in the readout chain will be discussed below.

In some embodiments, differential processing of signals may reduce or minimize noise in the readout chain. Differential processing of signals can reject common-mode noise that may be injected into the readout chain. The readout circuitry may include one or more differential components, such as a differential sample and hold circuit, differential amplifier(s) and/or a differential A/D converter. In some embodiments, differential signal processing may be used as early as possible in the readout chain (e.g., as close as possible to the pixel output), to avoid injecting common-mode noise into the readout chain. In some embodiments, the entire readout chain from a pixel output to a digital word may be performed by differential circuit components. However, the techniques described herein are not limited in this respect, as in some embodiments one or more single-ended readout circuitry components may be used.

Figure 10J:
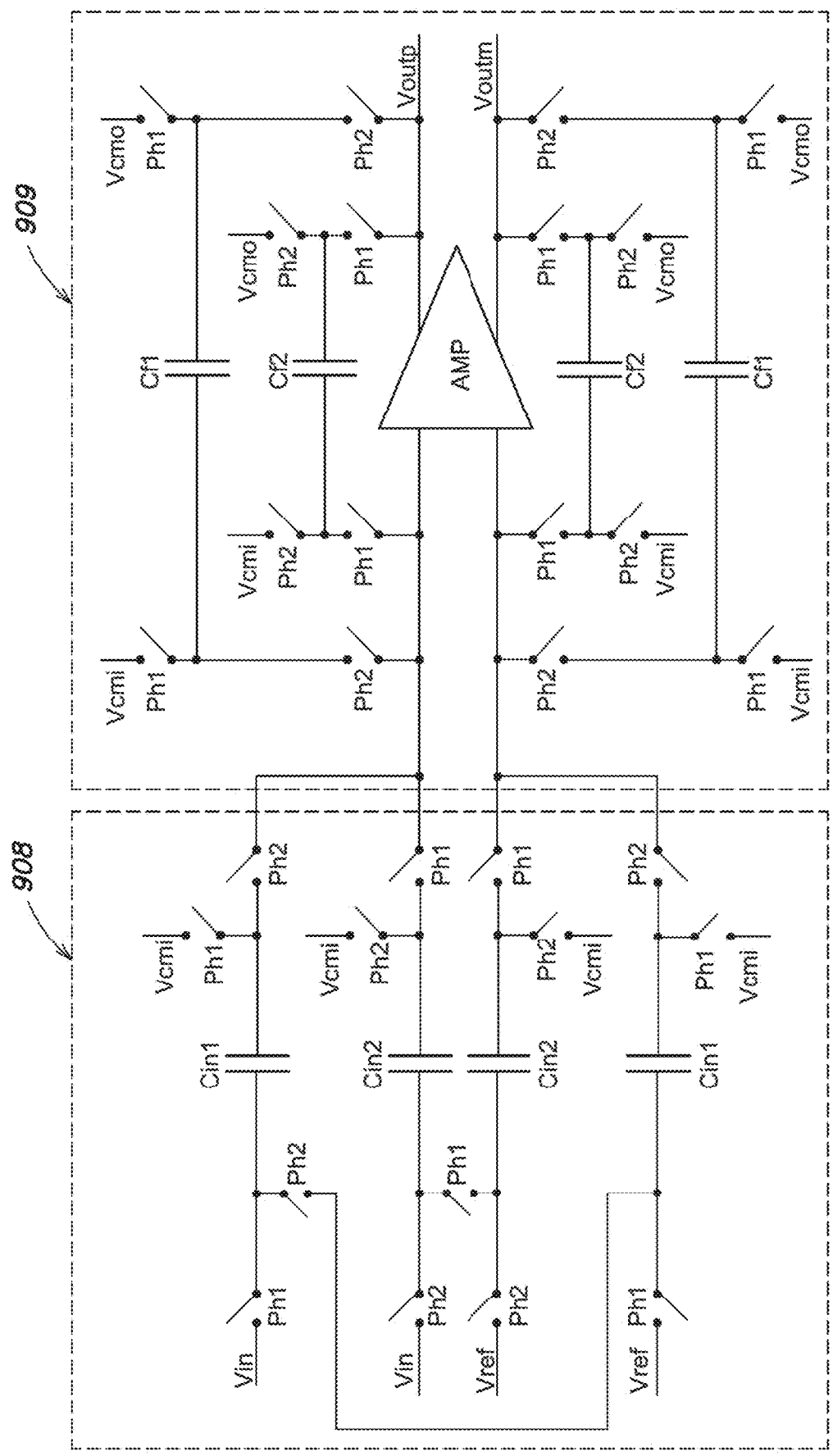
FIG. 10J shows readout circuitry shared by two columns including a differential sample and hold circuit and a differential amplifier.

FIG. 10J shows readout circuitry shared by two columns including a differential sample and hold circuit 908 and a differential amplifier 909. The differential sample and hold circuit 908 includes capacitors Cin1 for a first column of the pixel array and capacitors Cin2 for a second column of the pixel array. The differential amplifier 909 includes capacitors Cf1 for a first column of the pixel array and capacitors Cf2 for a second column of the pixel array.

Figure 10K:
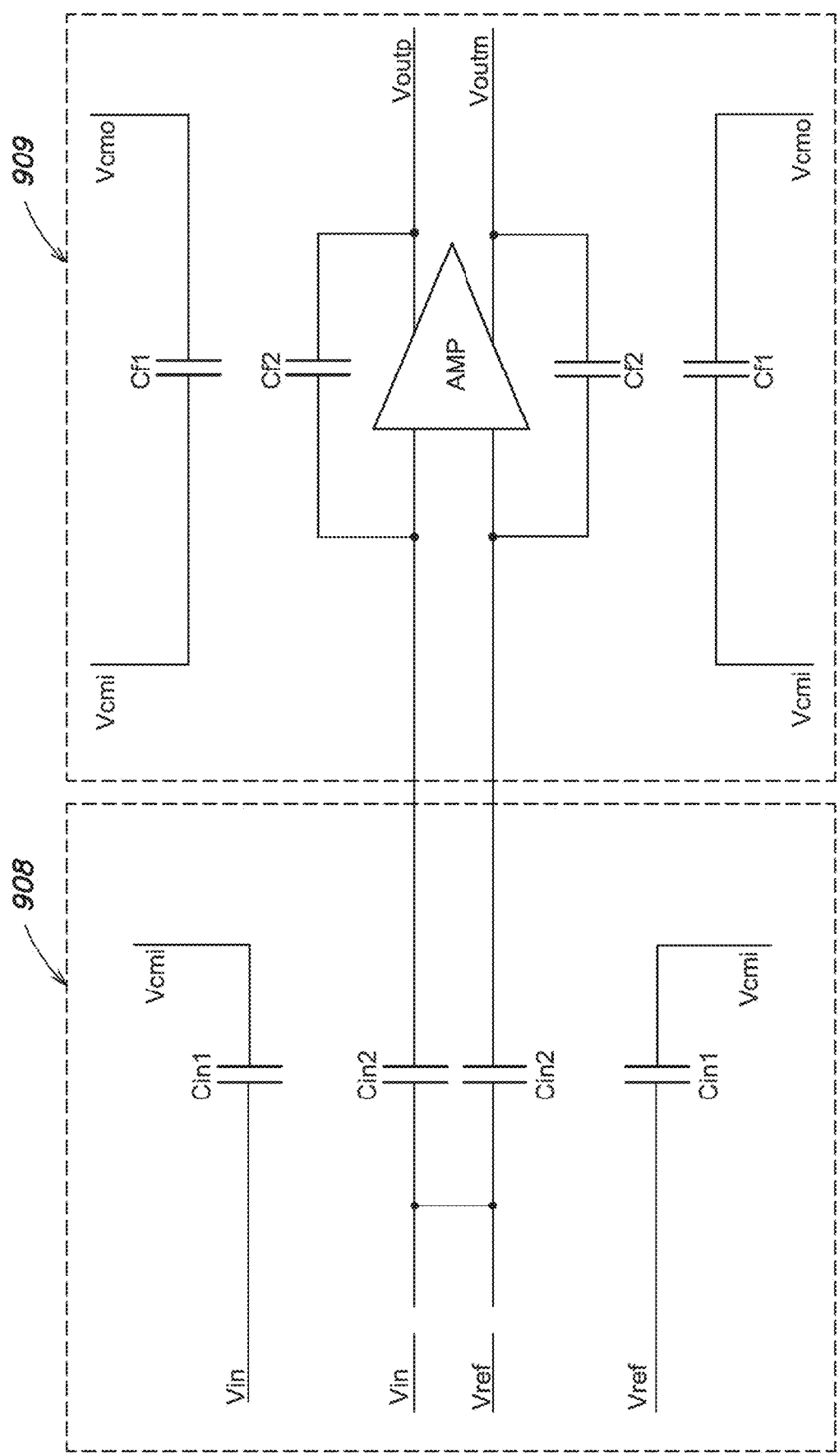
FIG. 10K shows a diagram of the differential sample and hold circuit and a differential amplifier when the first column is in the sample phase and the second column is in the hold phase.
Figure 10L:
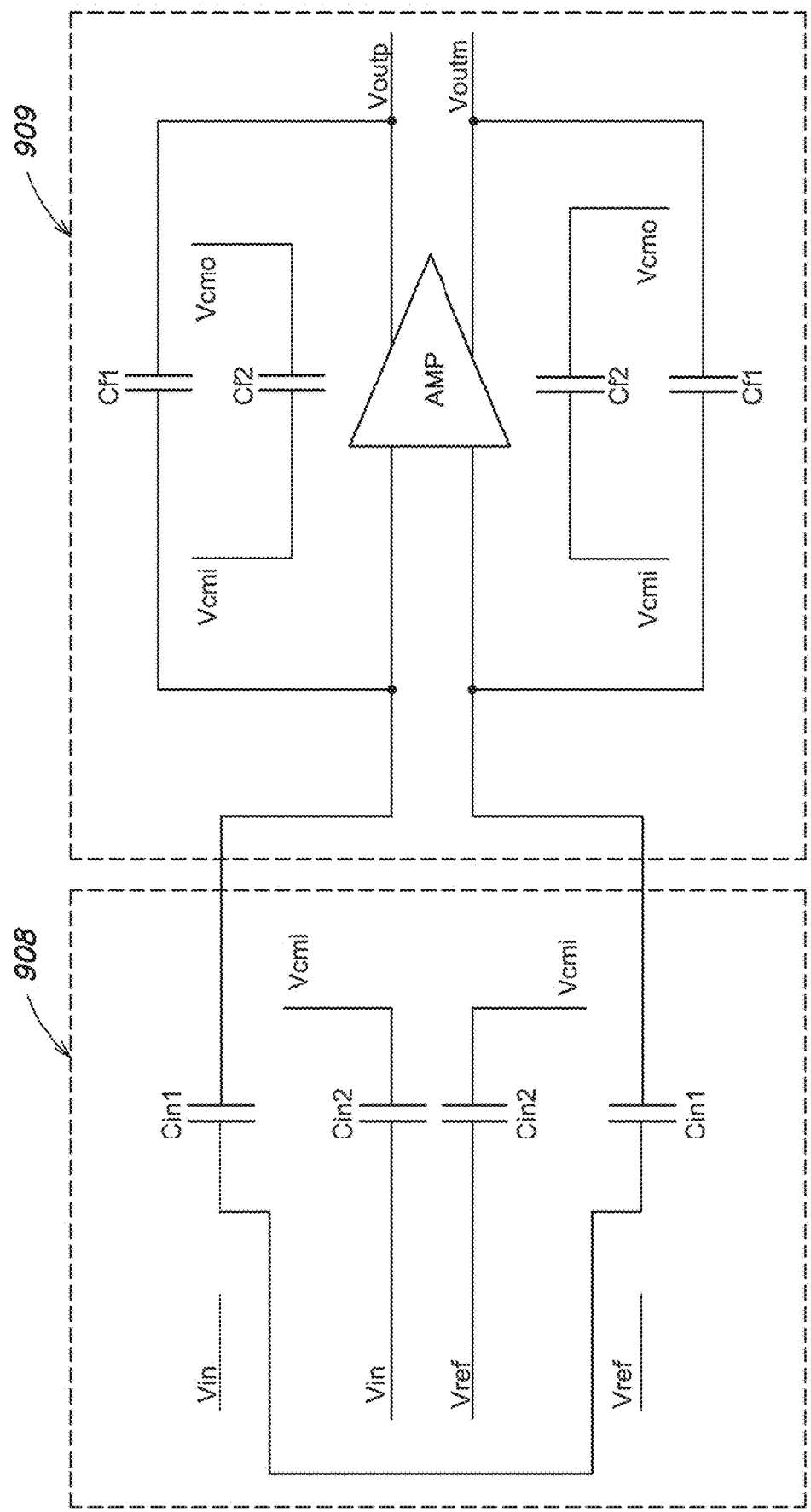
FIG. 10L shows a diagram of the differential sample and hold circuit and a differential amplifier when the second column is in the sample phase and the first column is in the hold phase.

FIG. 10K shows a diagram of the differential sample and hold circuit 908 and a differential amplifier 909 when the first column is in the sample phase and the second column is in the hold phase, with capacitors Cin2 being connected to the input of the differential amplifier 909. FIG. 10L shows a diagram of the differential sample and hold circuit 908 and a differential amplifier 909 when the second column is in the sample phase and the first column is in the hold phase, with capacitors Cin1 being connected to the input of the differential amplifier 909.

Figure 10M:
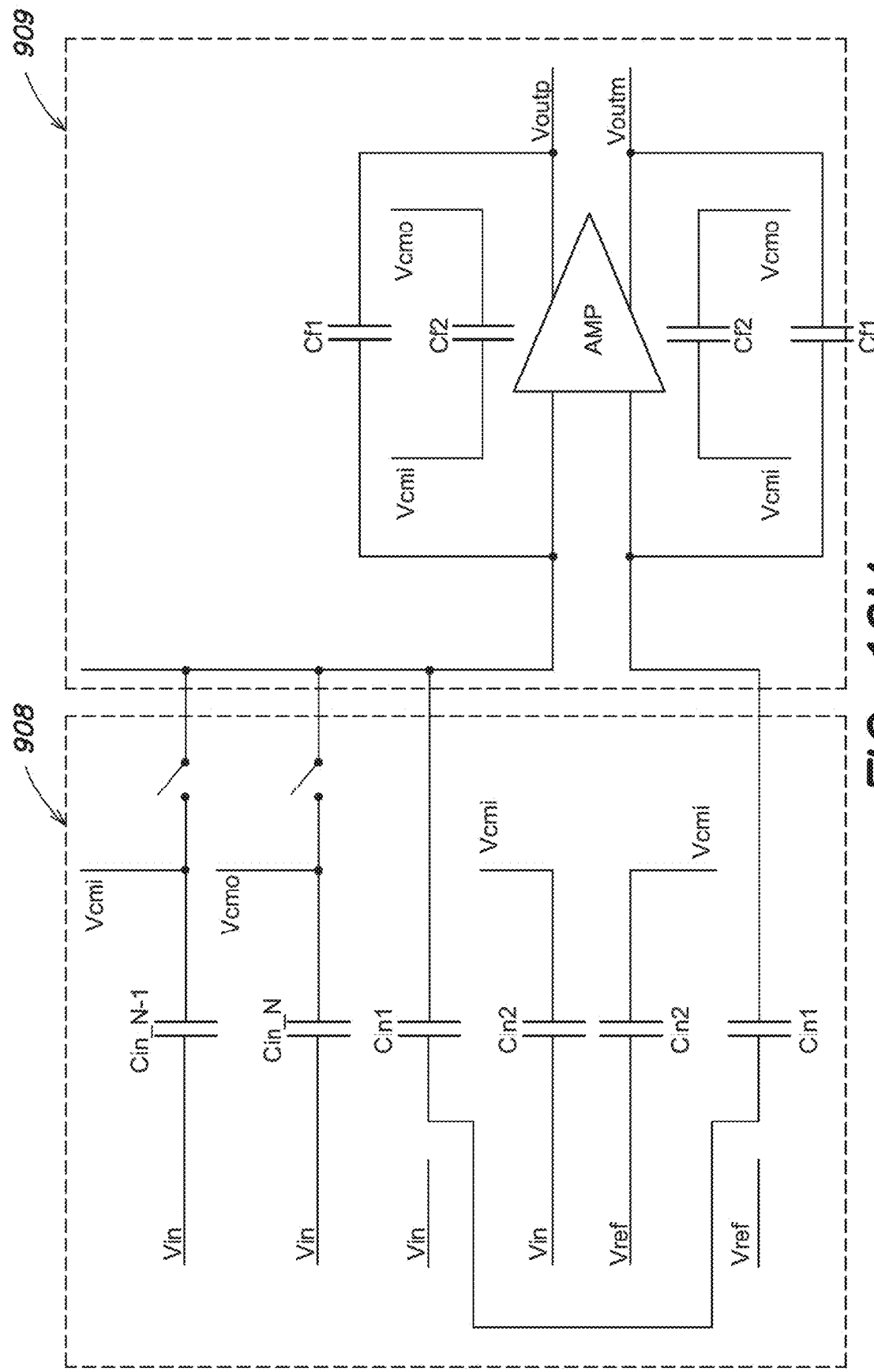
FIG. 10M shows readout circuitry shared by more than two columns including a differential sample and hold circuit and a differential amplifier.

FIG. 10M shows readout circuitry shared by more than two columns including a differential sample and hold circuit 908 and a differential amplifier 909. FIG. 10M is similar to FIG. 10F in that a differential amplifier 901 is shared by more than two columns, with the use of a differential sample and hold circuit 908 and a differential amplifier 909.

Dark Current Sampling

As understood by those of ordinary skill in the art, "dark current" is current that is produced in a photodetector when no light is being detected by the photodetector. Designing a photodetector to correct for the effect of dark current can improve the quality of photodetection.

In some embodiments of the integrated device described herein, one or more of the charge storage bins may be used to sample the dark current. For example, a charge storage bin may sample dark current by aggregating carriers that arrive during a time period in which no light or a very low level of light is received by the photodetector. In some embodiments, such as those relating to fluorescence lifetime measurements, the last bin (e.g., bin3) may be used to sample the dark current if the timing is such that it occurs once the probability of light emission drops to a negligible value. Sampling the dark current may allow subtracting the dark current from samples in other bins, thereby correcting for the effect of dark current.

Number and Timing of Time Bins

Any suitable number of time bins may be used. In FIGS. 3A and 3B, an example of a pixel with four time bins has been illustrated. FIG. 8C shows a plot in which eight bins are used. However, a pixel having any suitable number of time bins may be produced based on the desired temporal resolution and other factors. Increasing the number of bins may increase the area taken up by each pixel, and may be achieved by reducing the overall number of pixels or by using a fabrication process having a smaller feature size. Using a small number of bins may allow increasing the number of pixels that can fit on a chip. In some embodiments, a single bin may be used to determine the number of photons arriving within a particular time period. The number of bins may be increased or decreased at least in part by increasing or decreasing the number extensions of the charge carrier confinement region fabricated on the chip extending from the carrier travel/capture region 106. The number of electrodes b0-bm-1, transfer electrodes, etc., may be increased or decreased accordingly based on the number of bins desired to be included in a pixel.

The timing of the time bins may be chosen in any suitable way. In some embodiments, the timing may be selected by setting start and end times for the time bin(s), as illustrated in FIG. 6K. For example, the timing for bin0 may be set by selecting the times at which t1 and t2 occur, and the timing of the remaining bins may be set similarly.

In some embodiments, the timing for the time bins may be a fixed such that the timing is the same in each measurement period. The timing may be set based upon a global timing signal. For example, a timing signal may establish the start of a measurement period, and time bins may be controlled to start and end based upon a predetermined amount of time having elapsed from the timing signal. In the fluorescence lifetime measurement context, the timing for the time bins may be set with respect to the timing of an excitation pulse based upon the possible range of fluorescence lifetimes that are expected to be detected. In the time-of-flight imaging context, the timing of the time bins may be set based on an expected distance range for the scene to be imaged. However, in some embodiments the timing of the time bins may be variable or programmable.

In some embodiments, the timing for the time bins may be set based upon the timing of a trigger event 702 that initiates a measurement period for a measurement 720. In the fluorescence lifetime measurement context, the timing for the time bins may be set in response to detecting the timing of an excitation pulse that excites a fluorophore. For example, when an light excitation pulse reaches the pixel 100, a surge of carriers may travel from the photon absorption/carrier generation region 102 to the drain 104. The accumulation of photogenerated carriers at the drain 104 in response to the excitation pulse may cause a change in voltage of the drain 104. Accordingly, in some embodiments the excitation pulse may be detected by detecting the voltage of the drain 104. For example, a comparator may compare the voltage of the drain 104 to a threshold, and may produce a pulse when the voltage of the drain 104 exceeds the threshold. The timing of the pulse may be indicate the timing of the trigger event 702, and the timing of the time bins (e.g., t1, t2, etc.) may be set based upon this timing. However, the techniques described herein are not limited in this respect, as any suitable technique may be used to detect the start of a measurement 720.

In some embodiments, the integrated device may be programmable to enable changing the timing of the time bins. In some embodiments, the timing of the time bins may be programmed for a particular set of measurements to be performed. For example, if the integrated device is used for a first type of test using a first set of markers having lifetimes within a first range, the time bins may be programmed to suitable values for discriminating lifetimes of the markers within that range. However, if the integrated device is used for another type of test that uses different markers having different lifetimes, the time bins may be changed by programming them to correspond to different time intervals suitable for the markers used in the second type of test.

Figure 11:
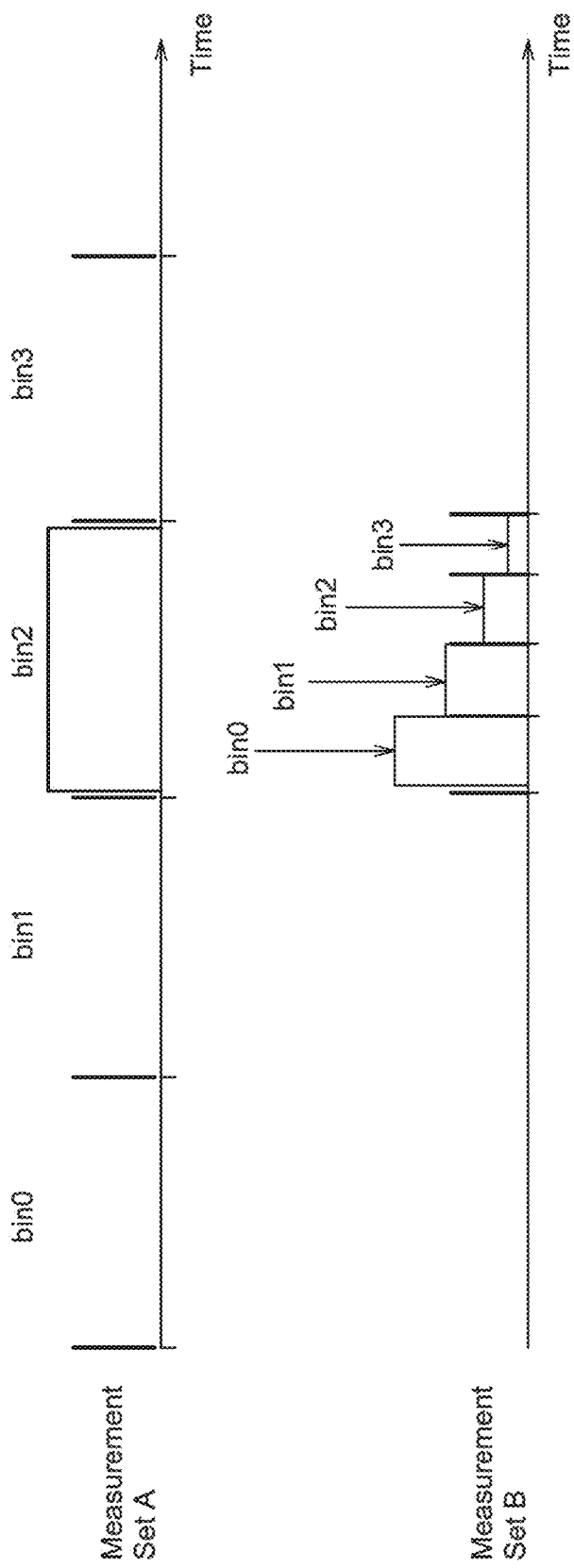
FIG. 11 shows the timing of the time bins may be controlled adaptively between measurements based on the results of a set of measurements.

In some embodiments, the timing of the time bins may be controlled adaptively between measurements based on the results of a set of measurements. For example, as illustrated in FIG. 11, a first set of measurements (Measurement Set A) may be performed using a first set of time bins that span a relatively large time interval. The quantity of photons that arrived for each bin may be analyzed to determine whether a change should be made to the timing selected for the time bins to improve or optimize the temporal information obtained. In some embodiments, the quantity of photons that arrive for each bin may be analyzed to determine a narrower time interval of interest. For example, after performing a set of measurements with time bins as shown in Measurement Set A of FIG. 11, it may be determined that a significant number of photons arrived in the time period corresponding to bin2 and no photons arrived in the time periods corresponding to other bins. A second set of time bins may then be selected for a second set of measurements (Measurement Set B) that focuses on the narrower time period corresponding to bin2 of Measurement Set A. As illustrated in FIG. 11, Measurement Set B has four time bins within the time period corresponding to bin2 of Measurement Set A. By performing measurements with time bins according to Measurement Set B, further detail about the timing of arrival of photons may be obtained. For example, as illustrated in FIG. 11, higher temporal resolution about the timing of arrival of incident photons may be obtained within a selected time interval. Such an adaptive time bin determination process may allow obtaining a level of time resolution using a relatively small number of bins (e.g., 4 bins) that otherwise may necessitate a large number of bins (e.g., 16 bins).

In some embodiments, the timing for the time bins may be the same in all pixels of the array. In some embodiments, the timing may be different in different pixels such that different pixels capture carriers in different time bins. For example, a first set of pixels may capture carriers in a first set of time bins, and a second set of pixels may capture carriers in a second set of time bins that are at least partially different from the first set of time bins. For example, one row of pixels may have the time timing for their time bins and another row of pixels may have a different timing for their time bins. In some embodiments, a first set of rows of pixels (e.g., four rows) may have the same timing for their time bins, and another set of rows of pixels (e.g., another four rows) may have a different timing for their time bins. Pixels may be set and/or programmed individually and/or as a group.

Pixels with Sub-Pixels

Wavelength Discrimination

In some embodiments, a pixel of a pixel array may include a plurality of sub-pixels that are each capable of performing different types of measurements. Any number of sub-pixels may be included in a pixel.

Figure 12:
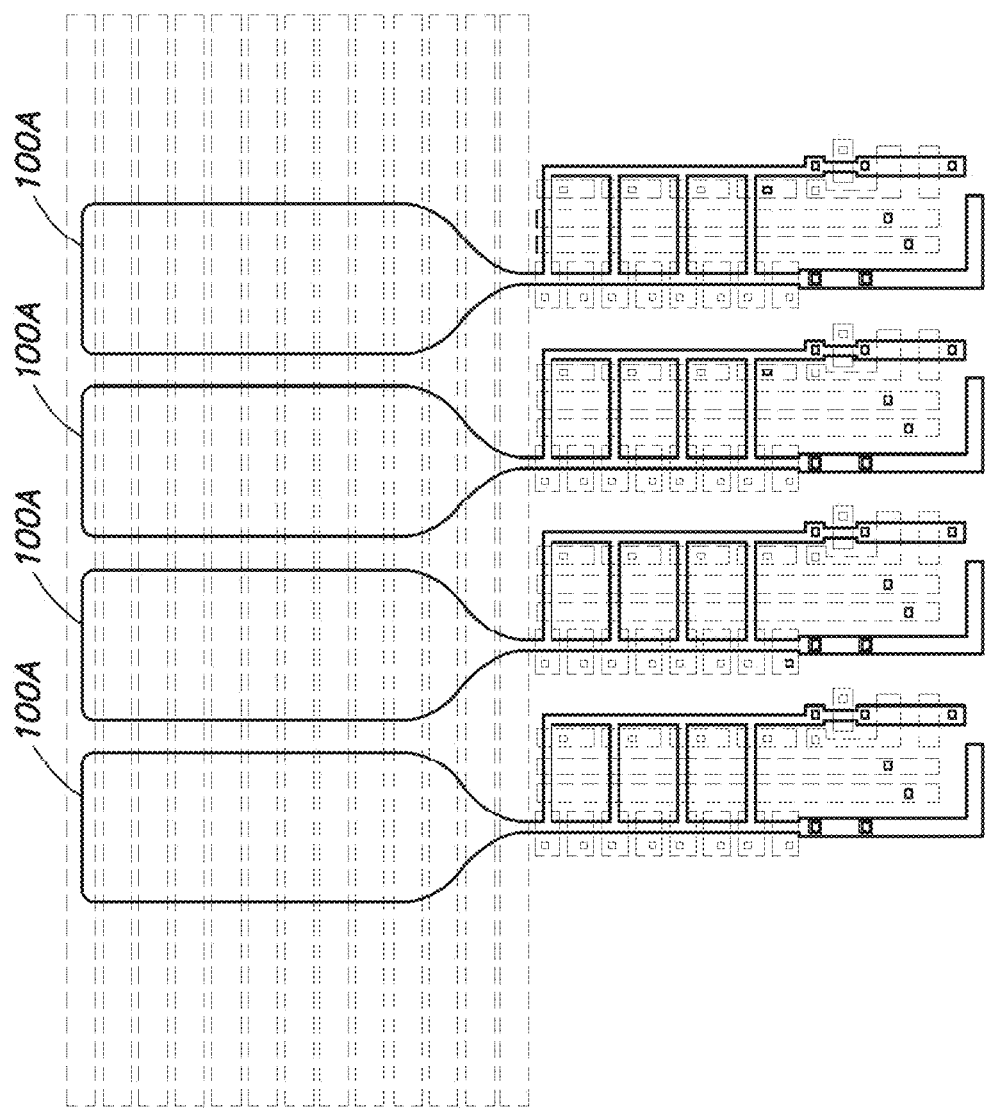
FIG. 12 shows an example of a pixel that includes four sub-pixels.

FIG. 12 shows an example of a pixel 1100 that includes four sub-pixels 100A. In some embodiments, each sub-pixel 100A in pixel 1100 may be configured to receive light of a different wavelength. For example, filters may be formed above sub-pixels 100A that allow photons of different wavelengths to be transmitted to sub-pixels 100A. For example, a first wavelength may be transmitted to a first sub-pixel 100A, a second wavelength may be transmitted to a second sub-pixel 100A, a third wavelength may be transmitted to a third sub-pixel 100A, and a fourth wavelength may be transmitted to a fourth sub-pixel 100A. A pixel 1100 having sub-pixels configured to receive light of different wavelengths may allow both temporal and spectral discrimination of incident light. In the fluorescence lifetime measurement context, providing the capability of both temporal and spectral discrimination may allow discriminating markers having different lifetimes, different spectral characteristics, or markers having both different lifetimes and different spectral characteristics.

Temporal Discrimination

In some embodiments, different sub-pixels 100A may be controlled to sample time bins for different time intervals. For example, a first sub-pixel 100A may be configured to sample a first set of time bins and a second sub-pixel may be configured to sample a second set of time bins. Similar structures in different sub-pixels 100A may sample time bins for different time intervals by controlling the timing of the charge carrier segregation structure to be different in different sub-pixels.

Pixel Array/Chip Architecture

Figure 13:
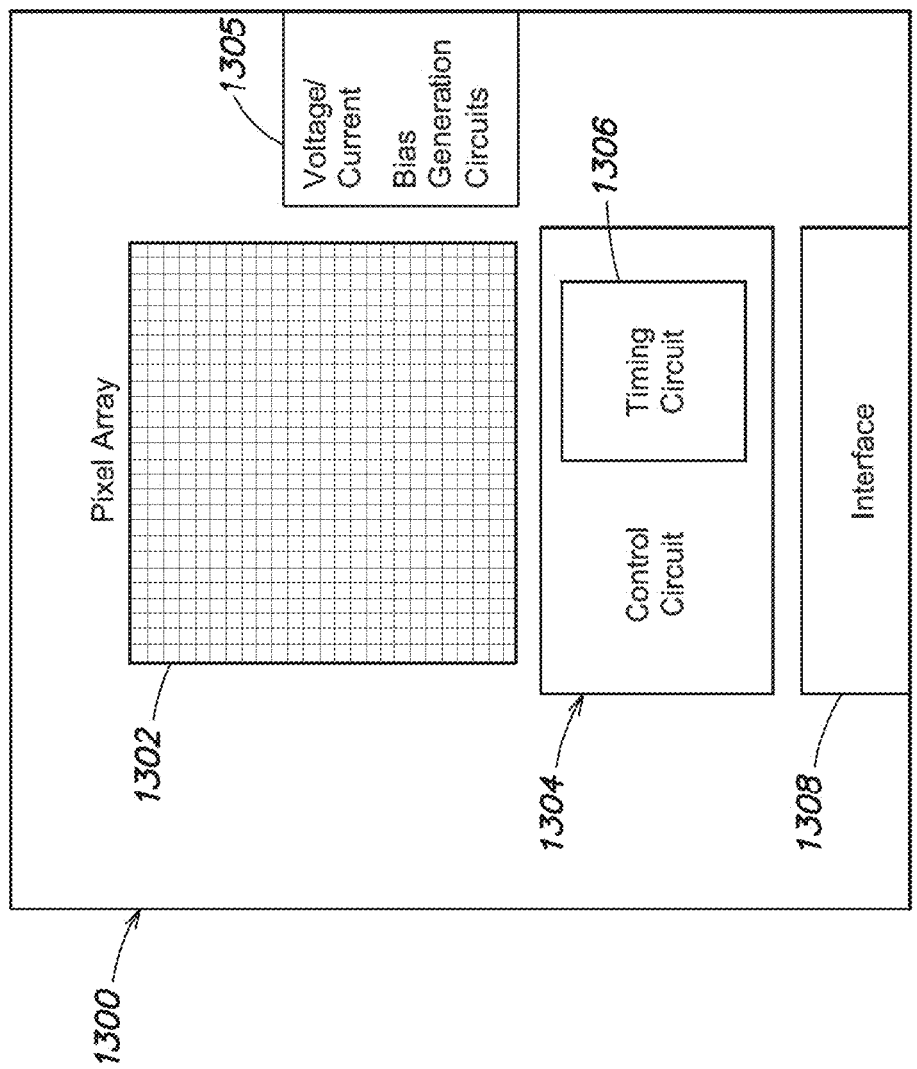
FIG. 13 shows a diagram of a chip architecture, according to some embodiments.

FIG. 13 shows a diagram of the chip architecture, according to some embodiments. As shown in FIG. 13, an integrated circuit or chip 1300 may include a pixel array 1302 including a plurality of pixels 100, a control circuit 1304 that includes a timing circuit 1306, voltage/current bias generation circuits 1305 and an interface 1308.

Pixel array 1302 includes an array of pixels 101 laid out in any suitable pattern, such as a rectangular pattern, for example. The pixel array 1302 may have any suitable number of pixels. In some embodiments, the pixel array may have a 64×64 array of 4096 pixels 101, each including four sub-pixels 101A. However, the techniques described herein are not limited as to the number or arrangement of pixels and sub-pixels included in the pixel array 1302. The pixel array may have row and/or column conductors for reading out rows or columns of the pixel array 1302. Pixels may be read out in parallel, in series, or a combination thereof. For example, in some embodiments a row of pixels may be read out in parallel, and each row of the pixel array may be read out sequentially. However, the techniques described herein are not limited in this respect, as the pixels may be read out in any suitable manner.

The pixel array 1302 is controlled by a control circuit 1304. Control circuit 1304 may be any suitable type of control circuit for controlling operations on the chip 1300, including operations of the pixel array 1302. In some embodiments, control circuit 1304 may include a microprocessor programmed to control operations of the pixel array 1302 and any other operations on the chip 1300. The control circuit may include a computer readable medium (e.g., memory) storing computer readable instructions (e.g., code) for causing the microprocessor performing such operations. For example, the control circuit 1304 may control producing voltages to be applied to electrodes of the charge carrier segregation structure(s) in each pixel. The control circuit 1304 may change the voltages of one or more electrodes, as discussed above, to capture carriers, transfer carriers, and to perform readout of pixels and the array. The control circuit may set the timing of operations of the charge carrier segregation structure based on a stored timing scheme. The stored timing scheme may be fixed, programmable and/or adaptive, as discussed above.

The control circuit 1304 may include a timing circuit 1306 for timing operations of the charge carrier segregation structure(s) of the pixels or other operations of the chip. In some embodiments, timing circuit 1306 may enable producing signals to precisely control the timing of voltage changes in the charge carrier segregation structure(s) to accurately time bin charge carriers. In some embodiments the timing circuit 1306 may include an external reference clock and/or a delay-locked loop (DLL) for precisely setting the timing of the signals provided to the charge carrier segregation structure(s). In some embodiments, two single-ended delay lines may be used, each with half the number of stages aligned 180-degrees out of phase. However, any suitable technique may be used for controlling the timing of signals on the chip.

The chip 1300 may include an interface 1308 for sending signals from the chip 1300, receiving signals at the chip 1300, or both. The interface 1308 may enable reading out the signals sensed by the pixel array 1302. Readout from the chip 1300 may be performed using an analog interface and/or a digital interface. If readout from the chip 1300 is performed using a digital interface, the chip 1300 may have one or more analog to digital converters for converting signals read out from the pixel array 1302 into digital signals. In some embodiments, the readout circuit may include a Programmable Gain Amplifier. One or more control signals may be provided to the chip 1300 from an external source via interface 1308. For example, such control signals may control the type of measurements to be performed, which may include setting the timing of the time bins.

Analysis of signals read out from the pixel array 1302 may be performed by circuitry on-chip or off-chip. For example, in the context of fluorescence lifetime measurement, analysis of the timing of photon arrival may include approximating a fluorescence lifetime of a fluorophore. Any suitable type of analysis may be performed. If analysis of signals read out from the pixel array 1302 is performed on-chip, chip 1300 may have any suitable processing circuitry for performing the analysis. For example, chip 1300 may have a microprocessor for performing analysis that is part of or separate from control circuit 1304. If analysis is performed on-chip, in some embodiments the result of the analysis may be sent to an external device or otherwise provided off-chip through interface 1308. In some embodiments all or a portion of the analysis may be performed off-chip. If analysis is performed off-chip, the signals read out from the pixel array 1302 and/or the result of any analysis performed by the chip 1300, may be provided to an external device through interface 1308.

In some embodiments, the chip 1300 may include one or more of the following:

1) on-chip, digitally controlled, pixel bias generators (DACs).

2) on-chip, digitally programmable gain amplifiers that convert the single-ended pixel output voltage signal to a differential signal and applies gain to the signal 3) digitally-controlled amplifier bias generators that allow scaling the power dissipation with the output rate.

Figure 14A:
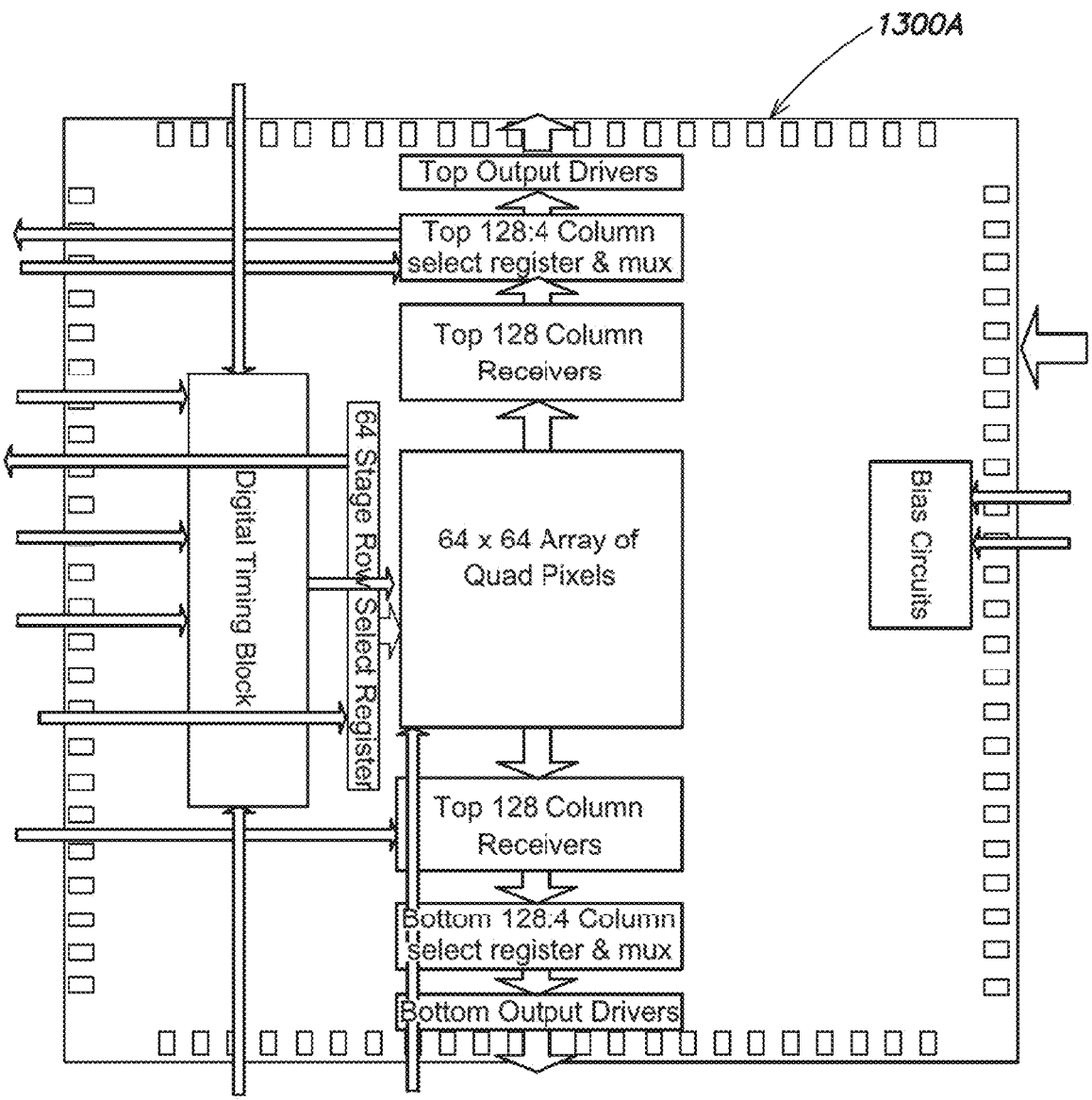
FIG. 14A shows a diagram of an embodiment of a chip having a 64×64 array of quad pixels, according to some embodiments.

FIG. 14A shows a diagram of an embodiment of a chip 1300A, which is an example of chip 1300 having a 64×64 array of quad pixels, according to some embodiments. In the embodiment of FIG. 14A, half of the pixel output signals are provided via the top side of the chip and the other half of the pixel output signals are provided via the bottom side of the chip. Bias circuits are included for setting the voltage of the electrodes of the charge carrier segregation structures.

Figure 14B:
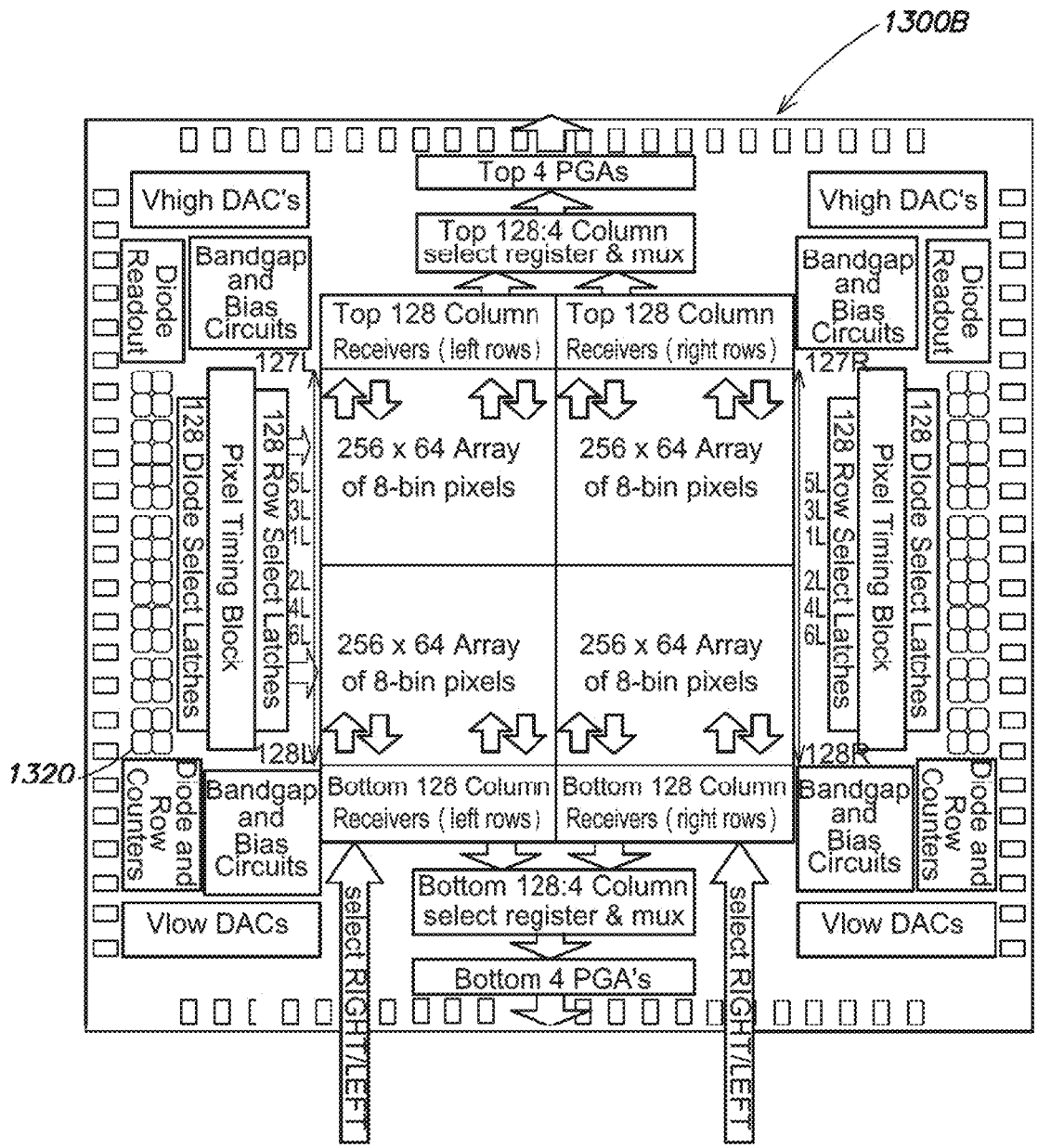
FIG. 14B shows a diagram of an embodiment of a chip that includes 2×2 arrays, with each array having 256×64 octal pixels array of quad pixels, according to some embodiments.

FIG. 14B shows a diagram of an embodiment of a chip 1300B, which is an example of chip 1300 includes 2×2 arrays, with each array having 256×64 octal pixels array of quad pixels, according to some embodiments. Bandgap and bias circuits are included. Digital to analog converts (DACs), including Vhigh DACs and Vlow DACs are included for setting the high and low voltages of the electrodes of the pixel array. FIG. 14B also shows light monitoring sensors 1320. Each light monitoring sensor may include a photodetector, such as a photodiode. In some embodiments, each light monitoring sensor may include a quad array of photodetectors (e.g., photodiodes) for aligning the chip 1300B with a light source. In an embodiment in which the chip 1300B is configured for detection of molecules, the light monitoring sensors may enable alignment of the chip 1300B with a waveguide that receives light from one or more locations in which the molecules are positioned. Diode readout circuits and a diode select register is also shown in FIG. 14B.

Examples of array sizes, dimensions, numbers of bins, and feature sizes are described above and shown in the figures merely by way of illustration, as any suitable of array sizes, dimensions, numbers of bins, and feature sizes may be used.

Example Integrated Circuit Realization and Method of Forming the Integrated Photodetector In some embodiments, the chip 1300 may be formed in a silicon substrate using a standard CMOS (Complementary Metal Oxide Semiconductor) process. However, the techniques described herein are not limited in this respect, as any suitable substrate or fabrication process may be used.

FIGS. 15-22 illustrate a process of forming a chip 1300, according to some embodiments.

Figure 15A:
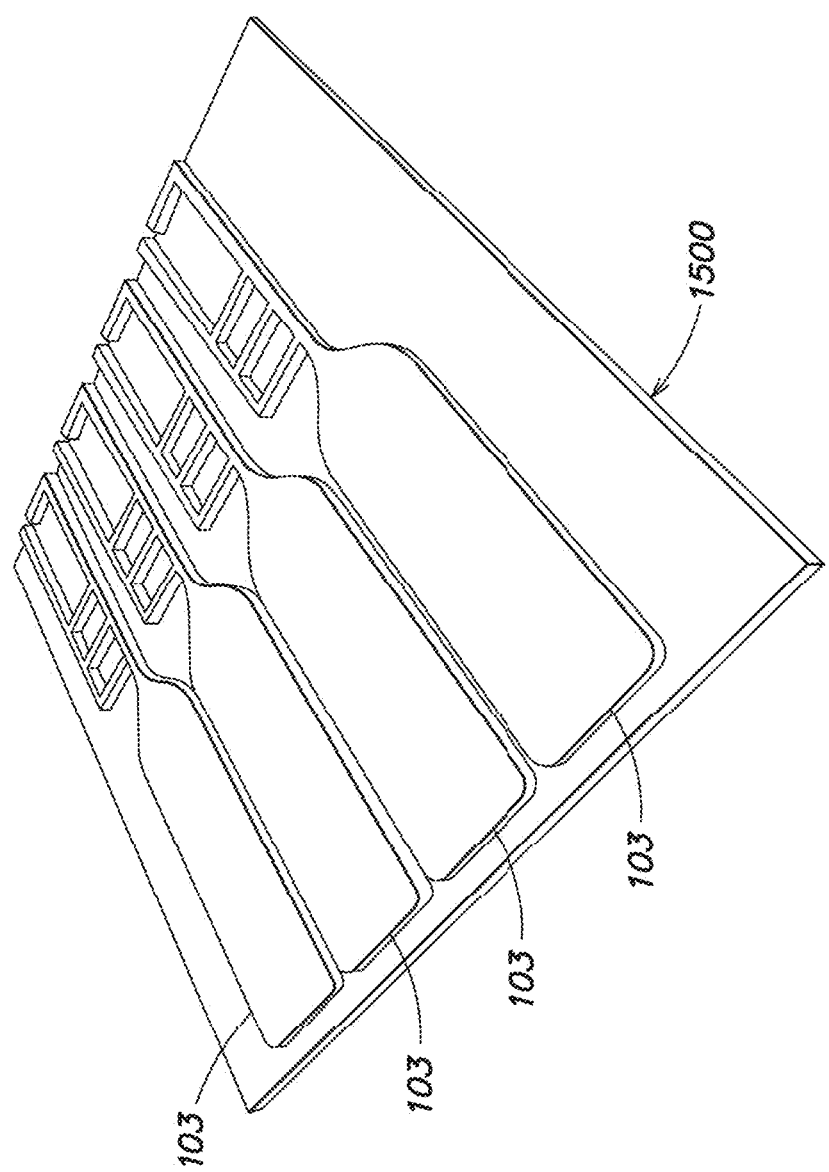
FIG. 15A shows a perspective view of charge confinement regions that may be formed in a semiconductor substrate.
Figure 15B:
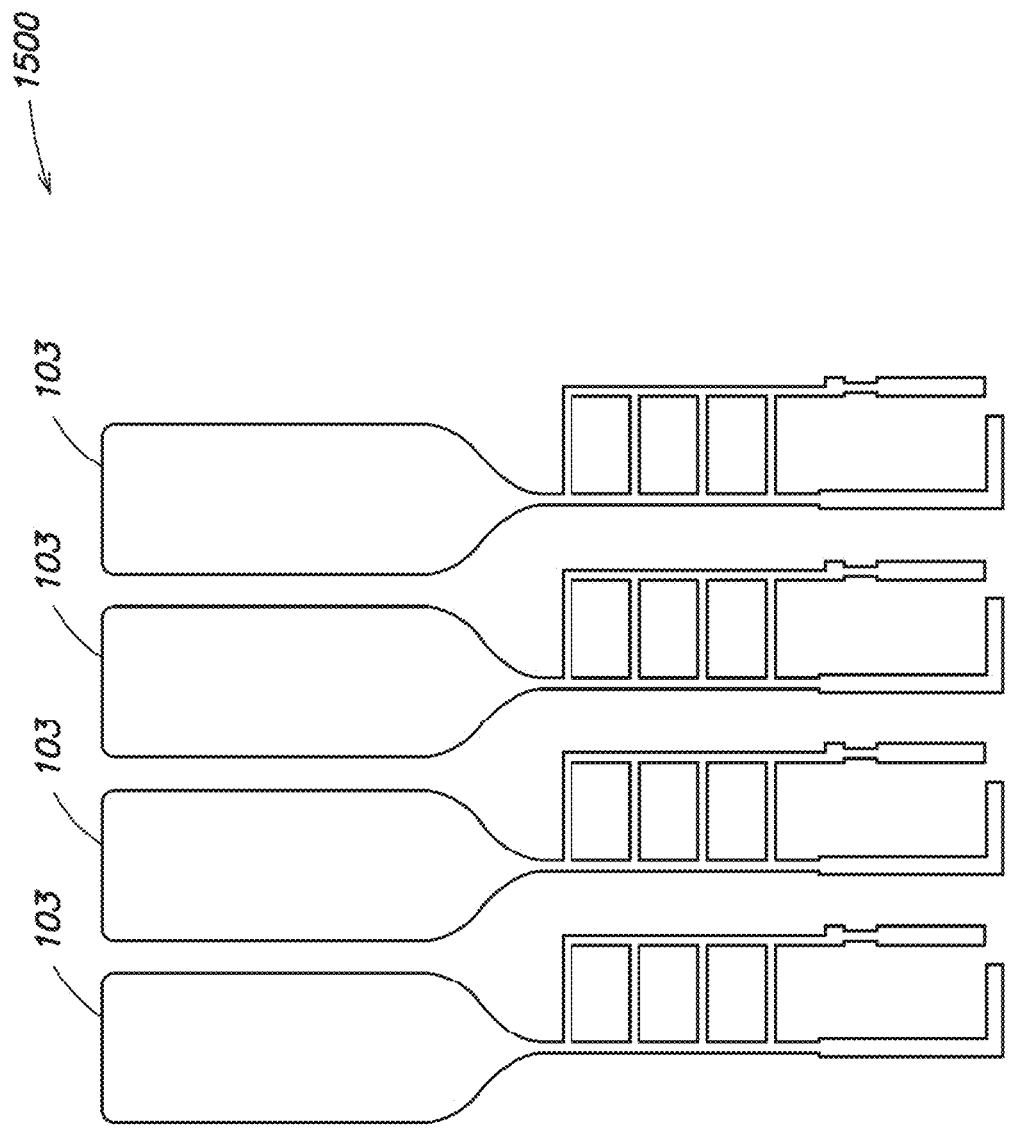
FIG. 15B shows a plan view corresponding to FIG. 15A.

FIG. 15A shows a perspective view of charge confinement regions 103 that may be formed in a semiconductor substrate. FIG. 15B shows a plan view corresponding to FIG. 15A. In some embodiments, charge confinement regions 103 may be formed in a bulk semiconductor substrate 1500. However, the techniques described herein are not limited to use of a bulk semiconductor substrate, as any suitable type of semiconductor substrate may be used. In some embodiments, the substrate 1500 and charge confinement regions 103 may be formed of monocrystalline silicon. However, the techniques described herein are not limited in this respect, as any suitable type of semiconductor material may be used. In some embodiments, using a silicon substrate may enable using a cost-effective industry standard CMOS process. However, any suitable fabrication process may be used. In some embodiments, a bulk silicon substrate having a p-type doping type may be used. However, any suitable doping type may be used, including n-type doping or p-type doping.

As shown in FIG. 15A, the charge confinement regions 103 may be a raised portion of substrate 1500. Charge confinement regions 103 may be formed by etching away regions of the substrate 1500 in the pattern shown in FIGS. 15A and 15B, thereby leaving raised charge confinement regions 103 extending above the substrate. An insulating layer may then be formed over and to the side of the charge confinement regions 103. For example, in some embodiments an insulating layer of silicon oxide may be formed on charge confinement regions 103 by thermal growth. However, any suitable technique may be used to form the insulating layer, and the insulating layer may include any suitable insulating material.

Figure 16:
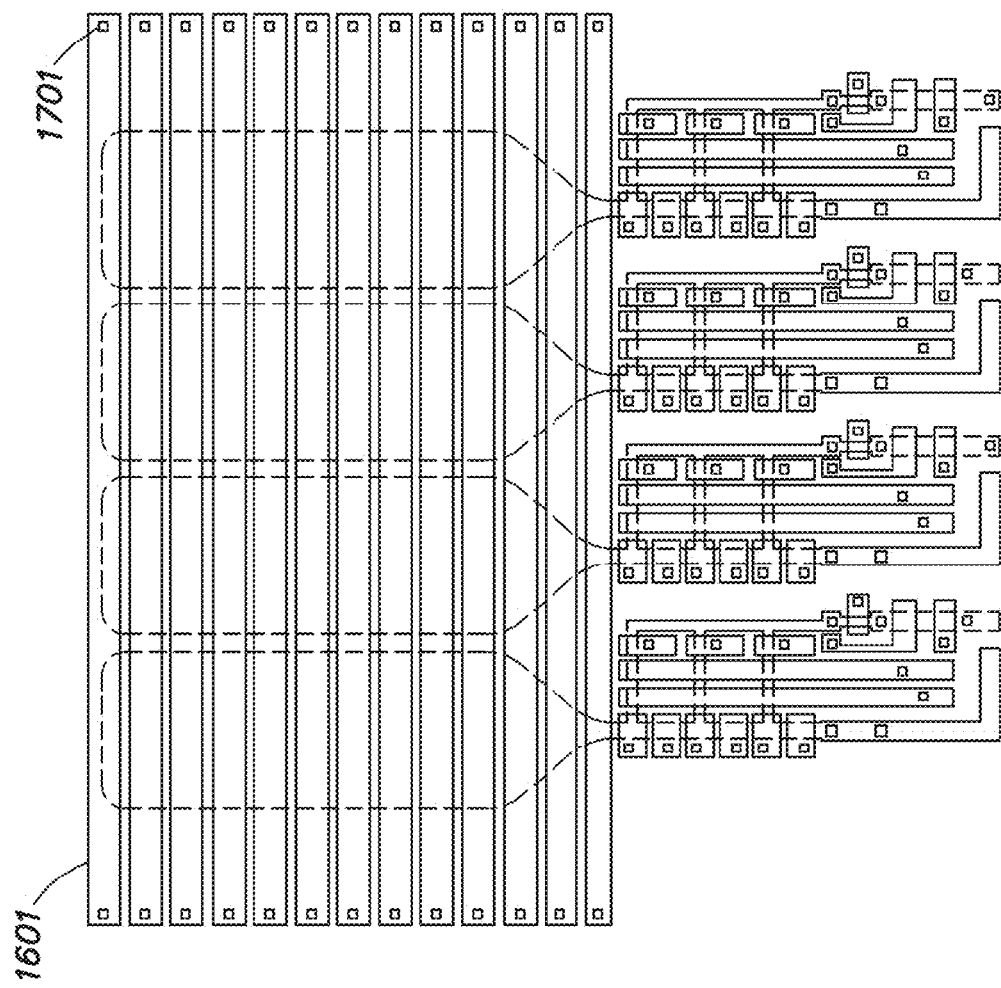
FIG. 16 shows the formation of electrodes over the insulating layer by forming a patterned polysilicon layer.

As shown in FIG. 16, electrodes as illustrated in FIG. 3B may be formed over the insulating layer by forming a patterned polysilicon layer 1601. The electrodes may be spaced apart from one another to allow different electrodes to be at different voltages. The electrodes may be formed of any suitable conductive material. In some embodiments, the electrodes may be formed of doped polysilicon. However, the techniques described herein are not limited to forming the electrodes of polysilicon, as any suitable conductive material may be used to form the electrodes (e.g., a metal). Conductive vias 1701 may be formed over the patterned polysilicon layer 1601 to contact the polysilicon layer 1601 through an insulating layer (not shown) overlying the patterned polysilicon layer 1601. The conductive vias 1701 may be formed of any suitable conductor.

Figure 17:
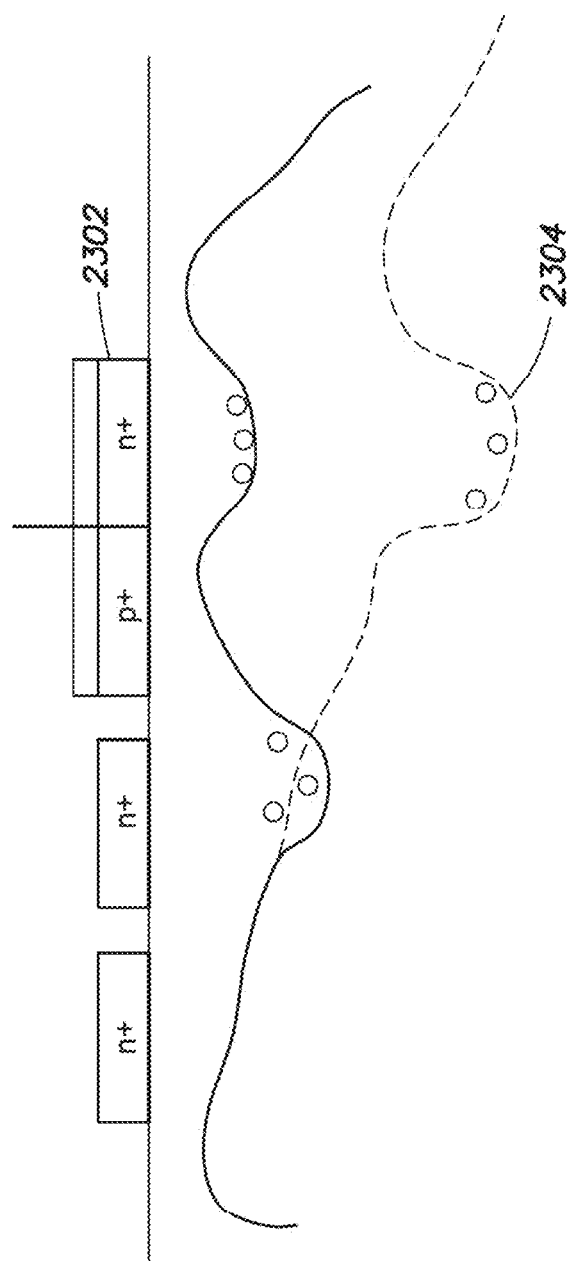
FIG. 17 shows a split-doped electrode having a p+ region and an n+ region.

In some embodiments, one or more electrodes (e.g., of polysilicon layer 1601) may be split-doped electrodes having both p– and n– type dopants. A split-doped electrode may enable forming a potential well to capture a carrier, as illustrated in FIG. 17. FIG. 17 shows a split-doped electrode 2302 having a p+ region and an n+ region. The n+ region and the p+ region produce different potential levels in the underlying semiconductor. As shown in FIG. 17, the n+ region of split-doped electrode 2302 may produce a potential well under the n+ region that can confine charge carriers (e.g., electrons). FIG. 17 illustrates that keeping the voltage of the split-doped electrode 2302 high may produce a potential gradient as shown in dashed lines, which may confine charge carriers (e.g., electrons) in a potential well 2304. Lowering the voltage of split-doped electrode 2302 may raise the electric potential under the split-doped electrode 2302 to enable transferring charge trapped in the potential well 2304 to a charge storage bin, for example.

Dopants may be formed in the semiconductor material to enable forming transistors of the readout circuitry 110. In some embodiments, a mask may be disposed over the charge confinement region 103 to prevent the doping of charge confinement region 103 during the formation of the transistors of readout circuitry 110, as doping charge confinement region 103 may form undesired potential wells in the charge confinement regions 103.

Figure 18:
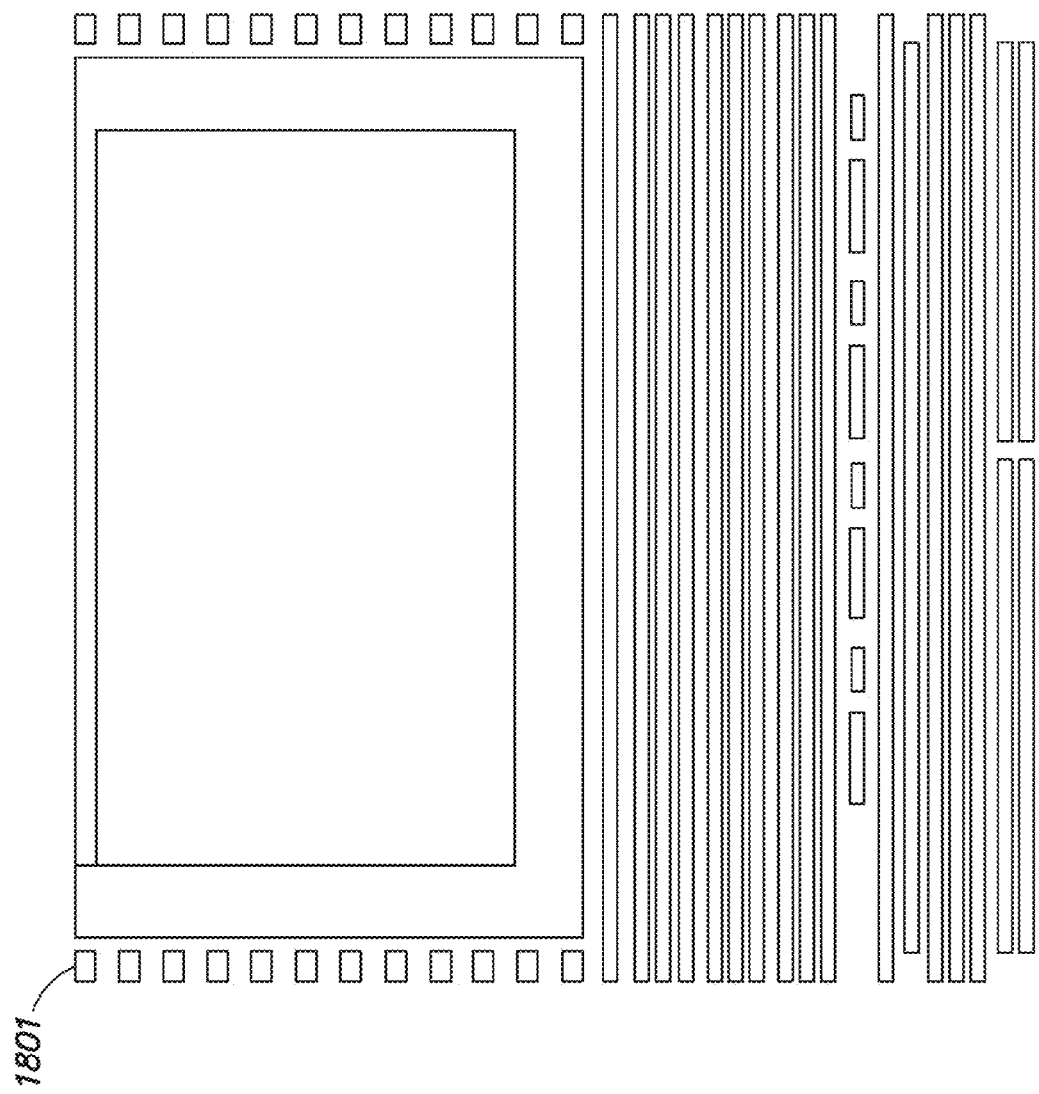
FIG. 18 shows the formation of a metal layer (e.g., metal 1) over the patterned polysilicon layer to connect to the vias.
Figure 19:
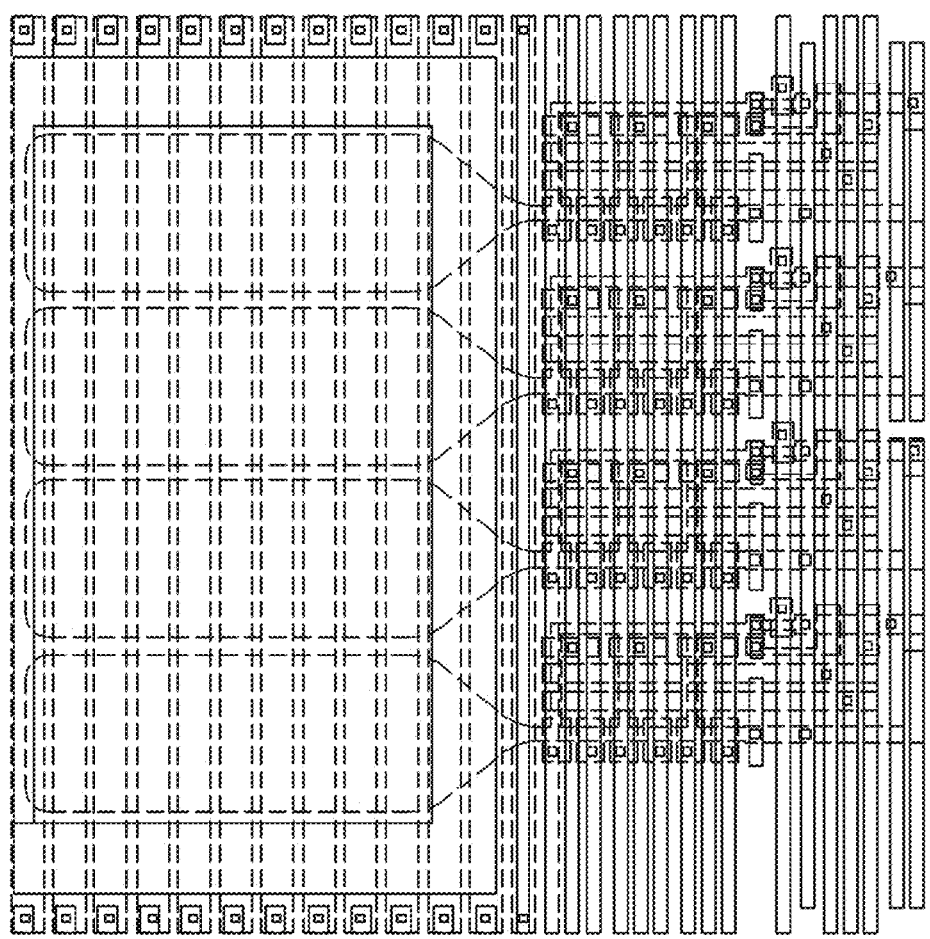
FIG. 19 shows the metal layer overlaid on the polysilicon layer and charge confinement regions.

FIG. 18 shows the formation of a metal layer 1801 (e.g., metal 1) over the patterned polysilicon layer 1601 to connect to the vias 1701. FIG. 19 shows the metal layer 1801 overlaid on the polysilicon layer 1601 and charge confinement regions 103.

Figure 20:
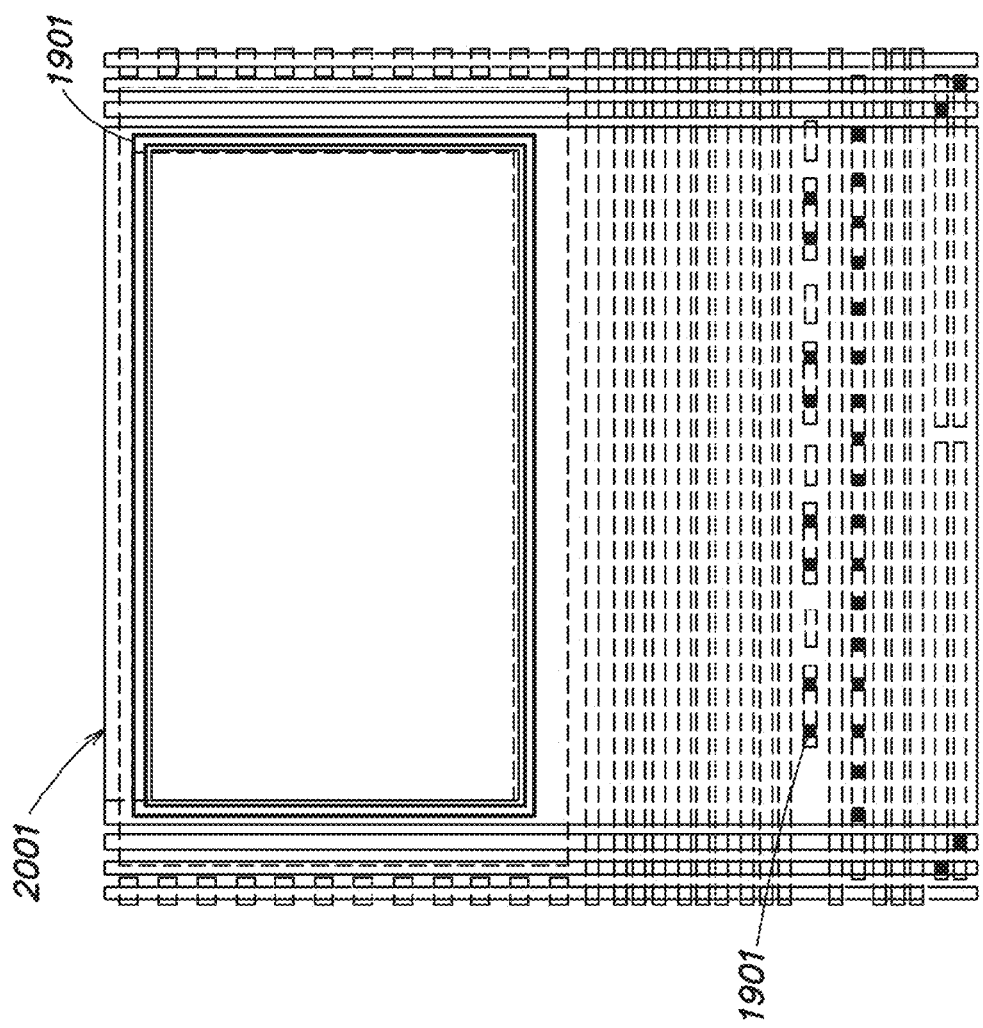
FIG. 20 shows the formation of vias to contact the metal layer.

FIG. 20 shows the formation of vias 1901 to contact the metal layer 1801. Conductive vias 1901 may be formed over the metal layer 1801 to contact the metal layer 1801 through an insulating layer (not shown) overlying the metal layer 1801. FIG. 20 also shows the formation of a second metal layer 2001 (e.g., metal 2) over the metal layer 1801 and vias 1901.

Figure 21:
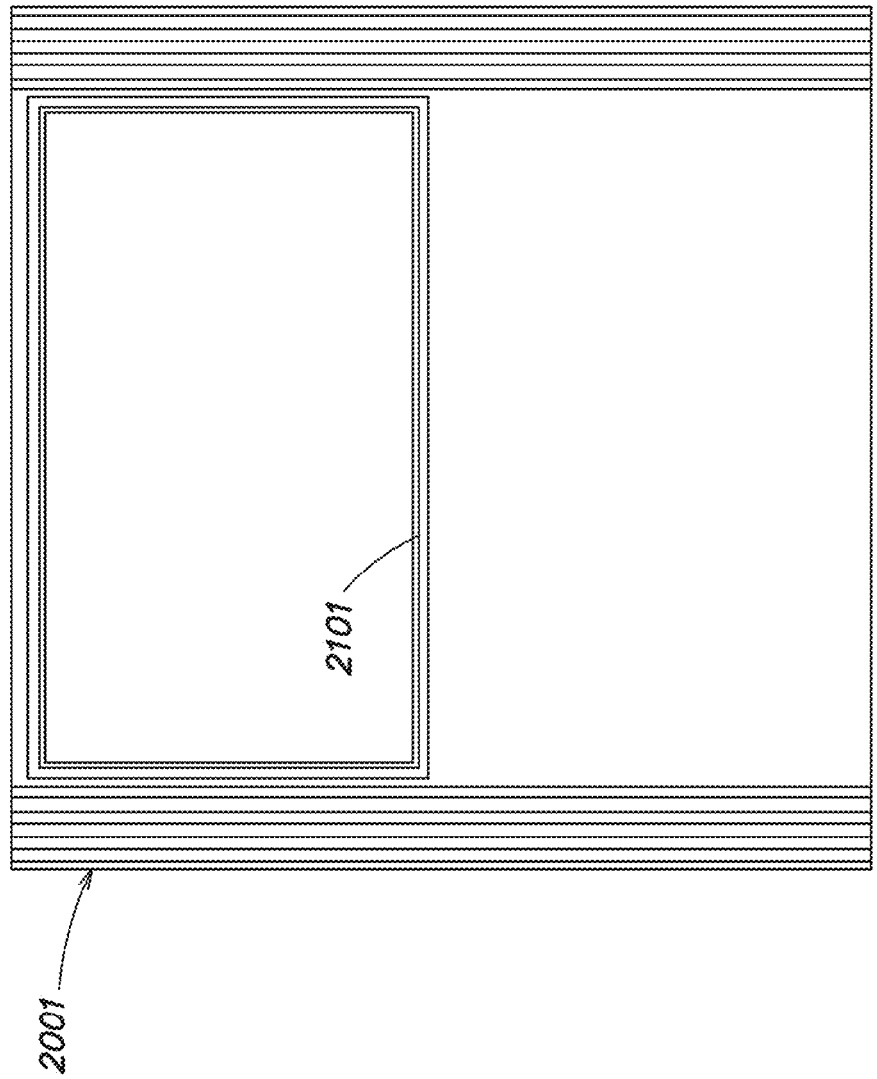
FIG. 21 shows the second metal layer as well as formation of via(s) to contact the second metal layer.

FIG. 21 shows the second metal layer 2001 as well as formation of via(s) 2101 over the metal layer 2001 to contact the metal layer 2001 through an insulating layer (not shown) overlying the metal layer 2001.

Figure 22:
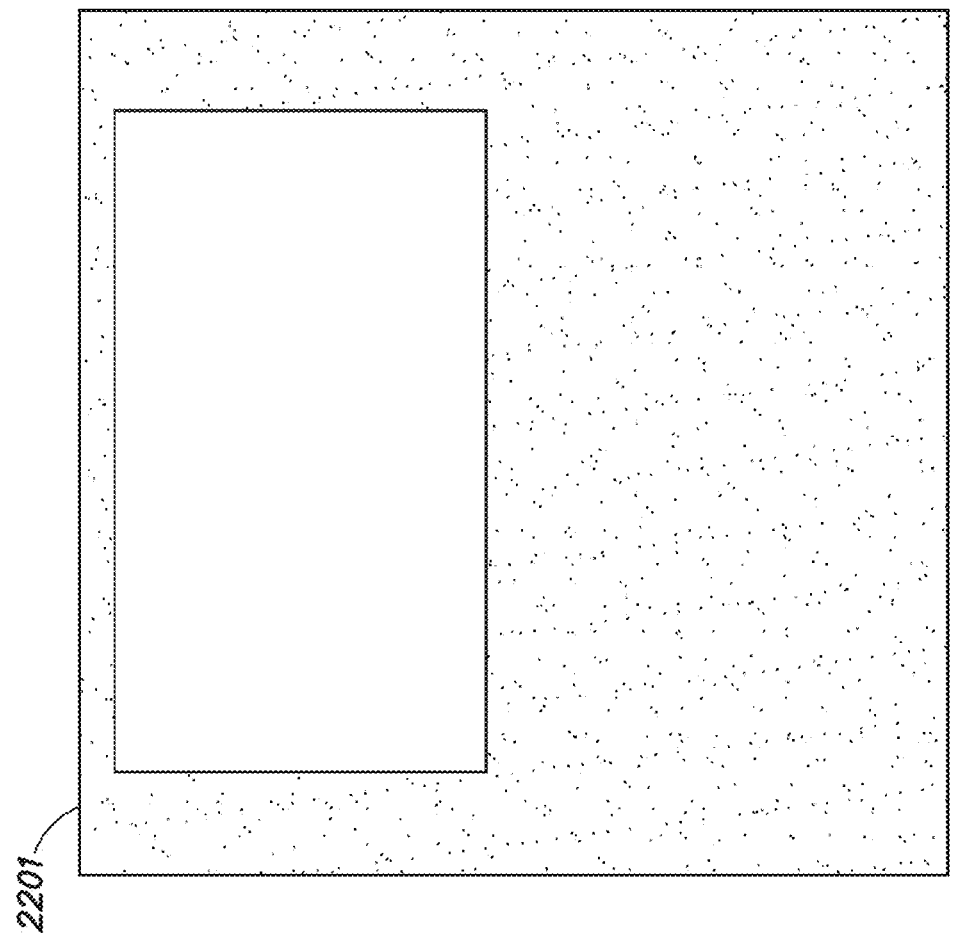
FIG. 22 shows the formation of a third metal layer.

FIG. 22 shows the formation of a third metal layer 2201 (e.g., metal 3) over the metal layer 2001 and the via(s) 2101 to contact the vias 2101.

The foregoing process is described by way of illustration, as the techniques described here are not limited to any particular fabrication process. Further, the techniques described herein are not limited as to the particular layout shown.

Drive Circuitry for the Charge Carrier Segregation Structure

The electrodes of the charge carrier segregation structure that overlie the substrate may have a substantial parasitic capacitance. Changing the voltages on the electrodes necessitates charging or discharging the parasitic capacitance. The speed with which current can be provided to charge or discharge the parasitic capacitance limits the speed at which the voltage of an electrode can be changed. As discussed above, in some embodiments charge carriers may be captured and transferred into time bins with nanosecond or picosecond resolution. The inventors have recognized and appreciated that the timing with which charge carriers may be captured may have a higher precision if the voltage of electrodes b0-bm-1 change more quickly, thereby raising the potential barriers at precise moments in time. However, rate of change of the voltage on electrodes b0-bm-1 is limited due to the parasitic inductance and equivalent series resistance (ESR) of the connection between the voltage supply and the electrodes b0-bm-1.

Further, charging and discharging the parasitic capacitances of the electrodes may consume significant power. The power dissipated by charging and discharging an electrode is $P_{diss}=(\frac{1}{2}) \cdot f \cdot C \cdot V^2$, where C is the capacitance between the electrode and the substrate, V is the voltage difference between the electrode and the substrate, and f is the frequency with which the voltage is switched.

Figure 23:
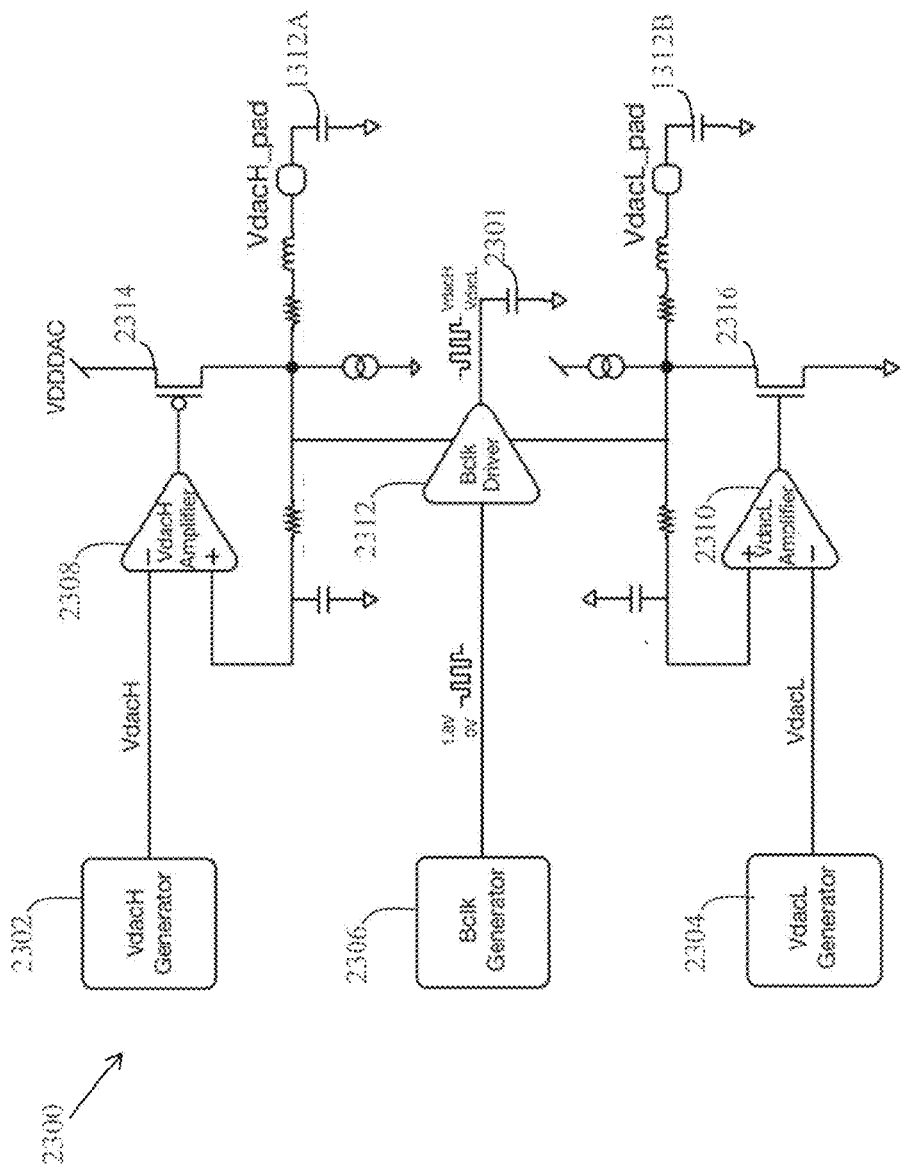
FIG. 23 shows an example of a drive circuit for driving an electrode of the charge carrier segregation structure, according to some embodiments.

FIG. 23 shows an example of a drive circuit 2300 for driving an electrode 2301 of the charge carrier segregation structure, according to some embodiments. Electrode 2301 is illustrated as a capacitor in FIG. 23. As discussed above, the electrode 2301 may be driven to a relatively low voltage $V_{low}$ and a relatively high voltage $V_{high}$ at selected times. The drive circuit 2300 includes a VdacH generator 2302 that produces the high voltage $V_{high}$ and a VdacL generator 2304 that produces the low voltage $V_{low}$. In some embodiments, the difference between $V_{low}$ and $V_{high}$ may be made as small as possible for the electrode to influence charge carriers in the manner designed, thereby reducing or minimizing power dissipation. In some embodiments, VdacH generator 2302 and/or VdacL generator 2304 may be programmable voltage generators that can produce desired voltages $V_{low}$ and/or $V_{high}$, and can allow changing $V_{low}$ and/or $V_{high}$.

The drive circuit 2300 also includes Bclk generator 2306, which can produce a timing signal for timing voltage transitions of the electrode 2301. The Bclk generator 2306 may be programmable, and may allow digitally selecting the times at which the edges of the timing signal occur, based on an input digital word. In some embodiments, the Bclk generator 2306 may be implemented using a delay locked loop (DLL), as discussed above. The timing signal from the Bclk generator 2306 is provided to the input of the Bclk driver 2312 which drives the electrode 2301.

The drive circuit 2300 also includes a VdacH amplifier 2308 and a VdacL amplifier 2310. The VdacH amplifier 2308 receives a signal from the VdacH generator and controls transistor 2314 using feedback to provide the voltage VdacH to the high power supply terminal of the Bclk driver 2312. The VdacH amplifier 2308 also charges capacitor 1312A to the voltage VdacH. The VdacL amplifier 2310 receives a signal from the VdacL generator and controls transistor 2316 using feedback to provide the voltage VdacL to the low power supply terminal of the Bclk driver 2312. The VdacL amplifier 2310 also charges capacitor 1312B to the voltage VdacL.

As discussed above, the electrode 2301 may have substantial capacitance. To supply enough current to charge the electrode 2301 with high speed, decoupling capacitors 1312A and 1312B may be provided to supply current to the to the low power supply terminal of the Bclk driver 2312 or the high power supply terminal of the Bclk driver 2312 during transitions.

The decoupling capacitor(s) may be positioned in close proximity to the electrode to limit the parasitic inductance and equivalent series resistance (ESR) between the electrode and the decoupling capacitor. When the voltage of an electrode is changed to a new voltage, the electrode is connected to the decoupling capacitor at the new voltage to supply current to the electrode through a current path having low parasitic inductance and/or equivalent series resistance (ESR), so that the voltage of the electrode can be changed quickly. In some embodiments, the decoupling capacitor may be positioned close enough to the electrode such that the parasitic inductance between the decoupling capacitor and the electrode is less than 3 nH, less than 2 nH, or less than 1 nH. In some embodiments, the equivalent series resistance (ESR) of the current path between the decoupling capacitor and the electrode is less than 70 ohms, less than 35 ohms, or less than 5 ohms. However, these values are provided merely by way of example, as the techniques described herein are not limited to specific values of inductance or resistance.

In some embodiments, electrodes b0-bm-1 may be connectable to one or more decoupling capacitors. In some embodiments, each electrode b0-bm-1 may have its own decoupling capacitors(s). For example, in some embodiments an electrode may have a single decoupling capacitor coupled between the high and low voltage supplies of the electrode, or two decoupling capacitors respectively coupled to the high voltage supply and the low voltage supply. However, the techniques described herein are not limited in this respect. Any or all of the electrodes of the charge carrier segregation structure may be connected to decoupling capacitors.

The decoupling capacitors may have any suitable capacitance value. In some embodiments, the capacitance value of a decoupling capacitor is ten to one hundred times the capacitance of the electrode to which it is to be connected. In some embodiments, the capacitance of a decoupling capacitor may be at least 150 pF, at least 300 pF, or at least 3 nF or higher. However, these values are provided merely by way of example, as the techniques described herein are not limited to specific values of capacitance.

Figure 24:
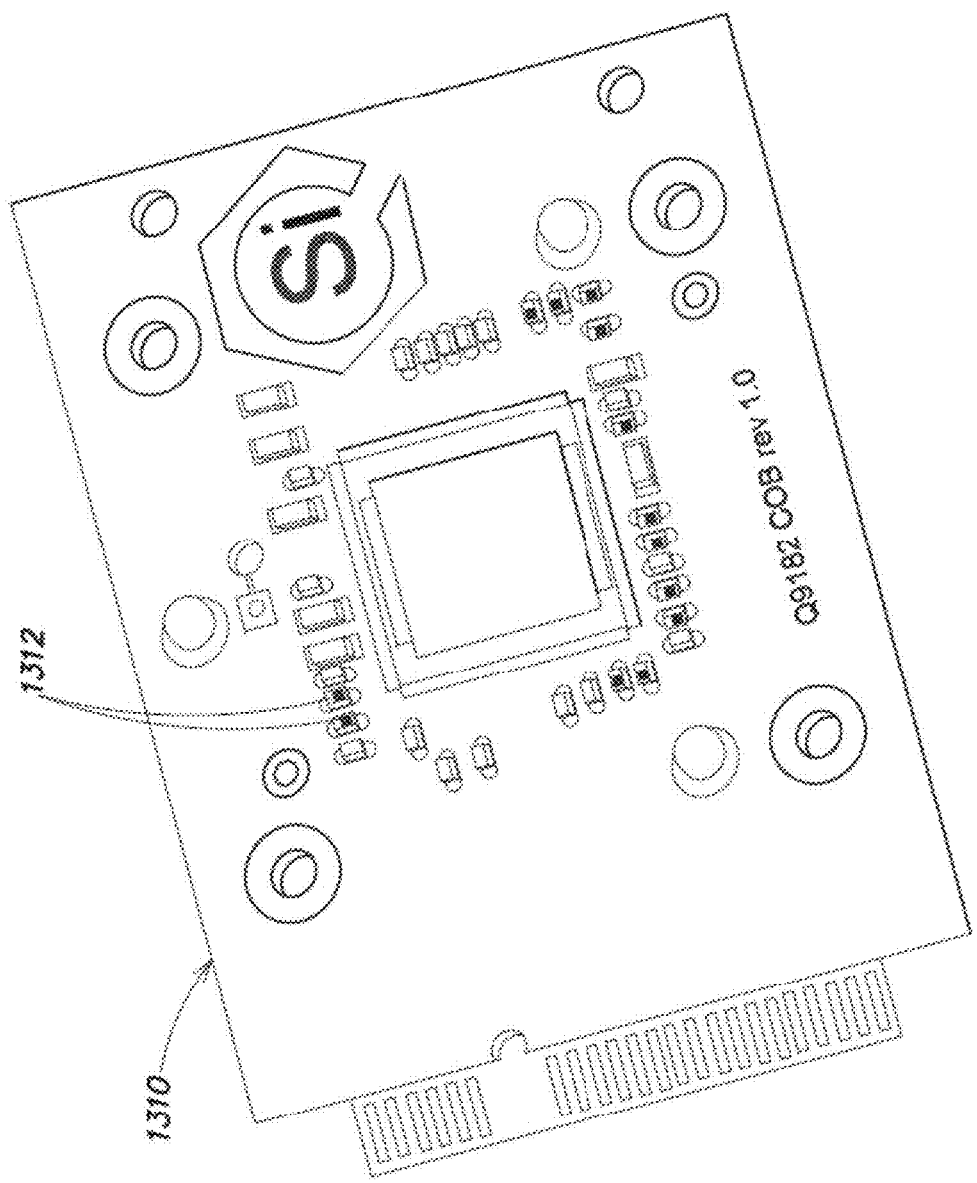
FIG. 24 shows an embodiment in which chip is affixed to a printed circuit board

A decoupling capacitor may be on-chip or off-chip. FIG. 24 shows an embodiment in which chip 1300 is affixed to a printed circuit board 1310, which may be termed a "chip-on-board" or "die-on-board" implementation. Wire bonds may connect the chip 1300 to one or more decoupling capacitors 1312 on the printed circuit board 1310, thereby providing current path having low parasitic inductance and/or equivalent series resistance (ESR) between an electrode of the chip 1300 and a decoupling capacitor 1312. In some embodiments, off-chip decoupling capacitors may be positioned within 1 cm, or within 5 mm of the chip 1300 or less. However the techniques described herein are not limited in this respect. As mentioned above, decoupling capacitor(s) may be formed on the chip 1300.

As discussed above, charging and discharging the electrodes of the charge carrier segregation structure may dissipate significant power. In some embodiments, the one or more rows of pixels of the chip 1300 and their corresponding electrodes may be disabled, which may limit the power consumption of the chip 1300. The chip 1300 may be programmable in this respect, and may allow selecting which rows will be enabled or disabled. The rows that are enabled and disabled may be changed over time.

Figure 25:
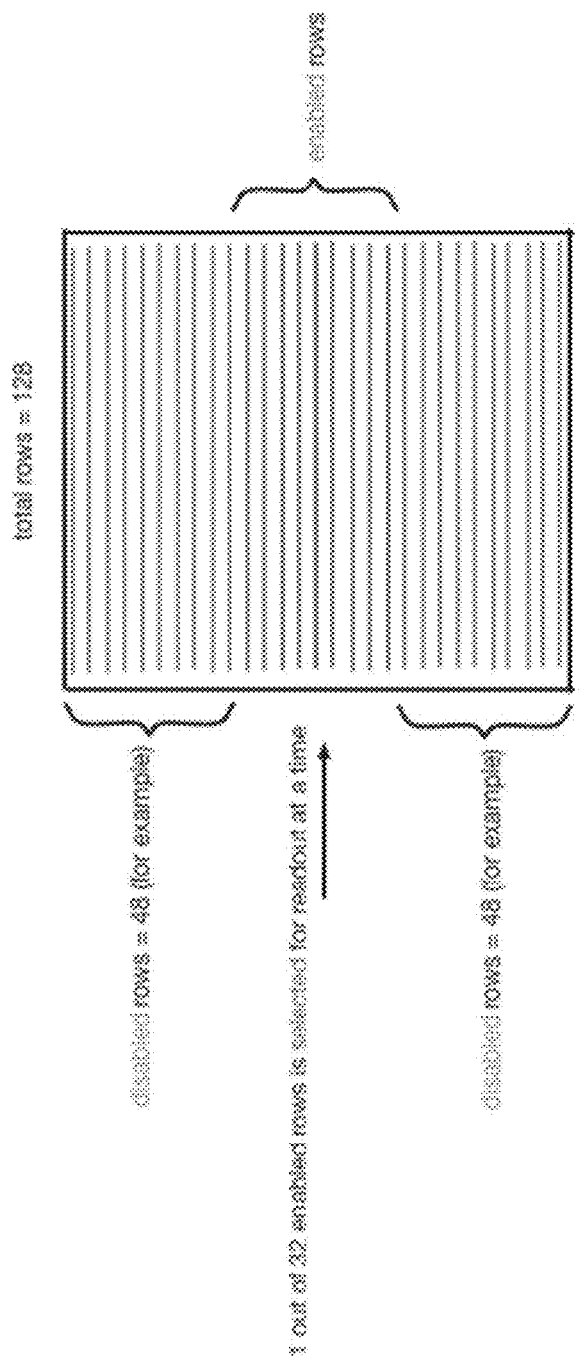
FIG. 25 illustrates enabling 32 rows in a central region of the chip and disabling 48 rows at the edges of the chip.

FIG. 25 illustrates enabling 32 rows in a central region of the chip and disabling 48 rows at the edges of the chip. Disabling one or more rows of the chip may allow reducing power consumption in situations or applications where not all the rows of the chip are needed.

Additional Aspects

In some embodiments, techniques described herein may be carried out using one or more computing devices. Embodiments are not limited to operating with any particular type of computing device.

Figure 26:
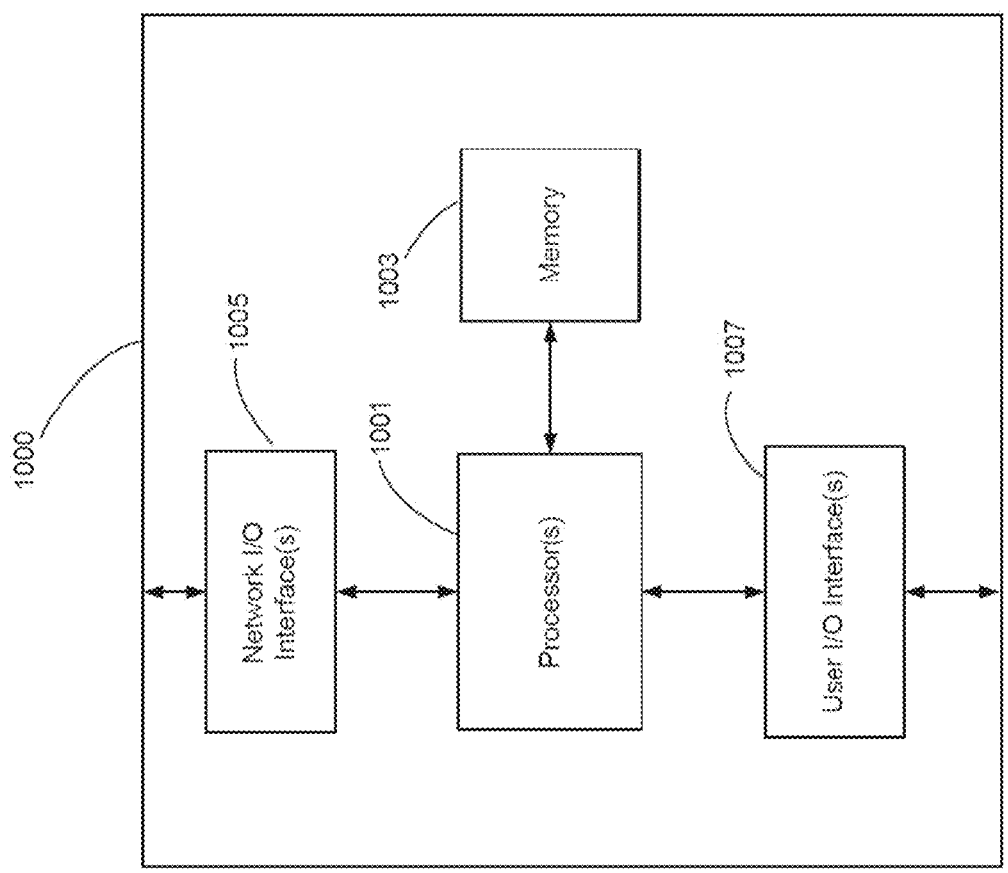
FIG. 26 is a block diagram of an illustrative computing device.

FIG. 26 is a block diagram of an illustrative computing device 1000 that may be used to implement a control circuit for controlling the pixel array or for performing analysis of the data from the pixels. Computing device 1000 may include one or more processors 1001 and one or more tangible, non-transitory computer-readable storage media (e.g., memory 1003). Memory 1003 may store, in a tangible non-transitory computer-recordable medium, computer program instructions that, when executed, implement any of the above-described functionality. Processor(s) 1001 may be coupled to memory 1003 and may execute such computer program instructions to cause the functionality to be realized and performed.

Computing device 1000 may also include a network input/output (I/O) interface 1005 via which the computing device may communicate with other computing devices (e.g., over a network), and may also include one or more user I/O interfaces 1007, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-discussed functions of one or more embodiments. The computer-readable medium may be transportable such that the program stored thereon can be loaded onto any computing device to implement aspects of the techniques discussed herein. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An apparatus, comprising;
   an integrated circuit configured to receive light from a luminescent molecule associated with a sub-unit of a biological molecule following respective excitations of the luminescent molecule, and to detect a timing of the light to identify the sub-unit; and one or more charge carrier storage regions, wherein the integrated circuit aggregates, in the one or more charge carrier storage regions, photogenerated charge carriers produced following the respective excitations of the luminescent molecule, wherein the one or more charge carrier storage regions comprises a plurality of charge carrier storage regions configured to store charge carriers produced at different times following excitation of the luminescent molecule, and the integrated circuit comprises a charge carrier segregation structure configured to selectively direct photogenerated charge carriers into selected charge carrier storage regions of the plurality of charge carrier storage regions based upon the timing of the light.

2. The apparatus of claim 1, wherein the timing of the light is indicative of luminance lifetime.

3. The apparatus of claim 1, wherein the luminescent molecule is excited by pulses of laser light.

4. The apparatus of claim 1, wherein the apparatus is configured to sequence the biological molecule based at least in part upon the timing of the light.

5. The apparatus of claim 4, wherein the apparatus is configured to sequence the biological molecule additionally based upon an intensity of the light and/or a spectral characteristic of the light.

6. The apparatus of claim 1, wherein the integrated circuit is configured to discard photogenerated charge carriers produced during a light excitation pulse for exciting the luminescent molecule.

7. The apparatus of claim 1, wherein the biological molecule is a nucleic acid and the sub-unit is a nucleotide.

8. A method, comprising by an integrated circuit, receiving light from a luminescent molecule associated with a sub-unit of a biological molecule following respective excitations of the luminescent molecule;

selectively directing photogenerated charge carriers into selected charge carrier storage regions of a plurality of charge carrier storage regions of the integrated circuit based upon a timing of the light;

aggregating, in the plurality of charge carrier storage regions, photogenerated charge carriers produced following the respective excitations of the luminescent molecule; and detecting the timing of the light using the aggregated photogenerated charge carriers to identify the sub-unit of a biological molecule.

9. The method of claim 8, wherein the timing of the light is indicative of luminance lifetime.

10. The method of claim 8, wherein the luminescent molecule is excited by pulses of laser light.

11. The method of claim 8, further comprising sequencing the biological molecule based at least in part upon the timing of the light.

12. The method of claim 11, wherein the sequencing is additionally based upon an intensity of the light and/or a spectral characteristic of the light.

13. The method of claim 8, wherein the integrated circuit comprises a charge carrier segregation structure configured to direct photogenerated charge carriers into selected charge carrier storage regions of the plurality of charge carrier storage regions based upon the timing of the light.

14. The method of claim 8, further comprising discarding charge carriers produced during a light excitation pulse for exciting the luminescent molecule.

15. The method of claim 8, wherein the biological molecule is a nucleic acid and the sub-unit is a nucleotide.

* * * * *